US006277609B1

(12) United States Patent
Eddy

(10) Patent No.: US 6,277,609 B1
(45) Date of Patent: Aug. 21, 2001

(54) METHOD TO PRODUCE BIOTIN

(75) Inventor: Christina K. Eddy, Loveland, CO (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/001,063

(22) Filed: Jan. 6, 1993

(51) Int. Cl.[7] .............................. C12P 11/00; C12N 15/31; C12N 15/63; C12N 15/70

(52) U.S. Cl. ................ 435/130; 435/252.3; 435/252.33; 435/320.1; 435/471; 435/476; 536/23.7

(58) Field of Search ................................ 435/240.2, 255, 435/252.3, 252.31, 252.33, 320.1, 172.3, 69.1, 119, 130.47, 476, 23.7; 536/23.2

(56) References Cited

U.S. PATENT DOCUMENTS

| | | | |
|---|---|---|---|
| 3,393,129 | 7/1968 | Shibata et al. | 195/28 |
| 4,563,426 | 1/1986 | Yamada et al. | 435/119 |
| 5,096,823 | 3/1992 | Gloeckler et al. | 435/252.31 |
| 5,110,731 | 5/1992 | Fisher | 435/119 |
| 5,212,058 | * 5/1993 | Baker et al. | 435/252.33 |

FOREIGN PATENT DOCUMENTS

| | | |
|---|---|---|
| 0 240 105 A1 | 10/1987 | (EP) . |
| 0 266 240 A1 | 5/1988 | (EP) . |
| 0 316 229 A1 | 5/1989 | (EP) . |
| 0 375 525 A1 | 6/1990 | (EP) . |
| 0 379 428 A1 | 7/1990 | (EP) . |
| 2 216 530 | 10/1989 | (GB) . |
| 61-149091 | 7/1986 | (JP) . |
| 61-202686 | 9/1986 | (JP) . |
| 62-155081 | 7/1987 | (JP) . |

OTHER PUBLICATIONS

Singer et al. (1991) Gene 106, 1–6.*
Brown et al., "The Production of Biotin by Genetically Modified Micro–organisms", pp. 295–326, 1991 *Biotechnology and Genetic Engineering Reviews*, vol. 9, Dec.
Cleary et al., "Location of Promoter and Operator Sites in the Biotin Gene Cluster of *Escherichia coli*", pp. 2219–2223, 1972, *Proc. Natl. Acad. Sci.*, vol. 69.
Eisenberg, "Biosynthesis of Biotin and Lipoic Acid", pp. 544–550, 1987, in *Escherichia coli and Salmonella typhimurium Cellular and Molecular Biology*, Neidhardt, F.C. et al., eds., American Society of Biology, Washington, D.C.

(List continued on next page.)

*Primary Examiner*—Ponnathapu Achutamurthy
*Assistant Examiner*—William W. Moore
(74) *Attorney, Agent, or Firm*—Whyte Hirschboeck Dudek SC

(57) ABSTRACT

The pesent invention is directed to biotin-producing recombinant cells transformed with an *Escherichia coli* bioE gene or a functional equivalent thereof, either alone or in combination with at least one additional nucleic acid sequence selected from *Bacillus sphaericus* bioA, bioB, bioD, bioF, bioW, bioX, and bioY genes, or a functional equivalent of any of these genes. Preferred recombinant cells are capable of converting essentially all biotin vitamers to true biotin. The present invention also provides a method to produce biotin by culturing such recombinant cells under appropriate conditions in an effective medium, which preferably includes biotin precursor supplements. The present invention is also directed to recombinant cells transformed with an *Escherichia coli* bioH gene, or functional equivalent thereof, either alone or with at least one nucleic acid selected from the group consisting of *Escherichia coli* bioA, bioB, bioC, bioD, bioE, and bioF genes, and functional equivalents thereof, said recombinant cells being capable of producing more biotin than a cell not transformed with an *Escherichia coli* bioH gene, or functional equivalent thereof; and use of such cells to produce biotin.

24 Claims, 23 Drawing Sheets

OTHER PUBLICATIONS

Gloeckler et al., "Cloning and Characterization of the *Bacillus sphaericus* Genes Controlling the Bioconversion of Pimelate into Dethiobiotin", pp. 63–70, 1990, *Gene*, vol. 87.

Guha et al., "Divergent Orientation of Transcription from the Biotin Locus of *Escherichia coli*", pp. 53–62, 1971, *J. Mol. Biol.*, vol. 56.

Izumi et al., from "Microbial Production of Biotin", pp. 242–243, 1989, in *Biotechnology of Vitamins, Pigments, and Growth Factors*, Elsevier Applied Science (E.J. Vandamme, ed.).

Magnuson et al., "Cloning and Nucleotide Sequence of the *fabD* Gene Encoding Malonyl Coenzyme A–acyl Carrier Protein Transacylase of *Escherichia coli*", pp. 262–266, 1992, *FEBS Letters*, vol. 229.

Ogata, "Microbial Synthesis of Dethiobiotin and Biotin", pp. 390–395, 1970, *Methods in Enzymology*, vol. 17a.

Ogata et al., "Studies on Biosynthesis on Biotin by Microorganisms. Part I. Accumulation of Biotin–Vitamers by Various Microorganisms", pp. 889–894, 1965, *Agr. Biol. Chem.*, vol. 29.

Ogata et al., "Studies on Biosynthesis on Biotin by Microorganisms. Part II. Identification of Biotin–Vitamers Accumulated by Various Microorganisms", pp. 895–901, 1965, *Agr. Biol. Chem.*, vol. 29.

Ohsawa et al., "Bioconversion of Pimelic Acid into Biotin by *Bacillus sphaericus bioB* Transformants", pp. 121–124, 1992, *J. Ferment. Bioeng.*, vol. 73.

Ohsawa et al., Cloning of the Biotin Synthetase Gene from *Bacillus sphaericus* and Expression in *Escherichia coli* and *Bacilli*, pp. 39–48, 1989, *Gene*, vol. 80.

O'Regan et al., "Nucleotide Sequence of the *bioH* Gene of *Escherichia coli*", p. 8004, 1989, *Nucleic Acids Research*, vol. 17.

Otsuka et al., "The *Escherichia coli* Biotin Biosynthetic Enzyme Sequences Predicted from the Nucleotide Sequence of the *bio* Operon", pp. 19577–19585, 1988, *J. Biol. Chem.*, vol. 263, Dec.

Ploux et al., "Investigation of the First Step of Biotin Biosynethesis of *Bacillus sphaericus*", pp. 685–690, 1992, *Biochem. J.*, vol. 287.

Sabatie et al., "Biotin formation by recombinant strains of *Escherichia coli*: influence of the host physiology", pp. 29–50, 1991, *J. Biotech.*, vol. 20.

Studier et al., "Use of Bacteriophage T7 RNA Polymerase to Direct Selective High–Level Expression of Cloned Genes", pp. 113–130, 1986, *J. Mol. Biol.*, vol. 189.

\* cited by examiner

FIG. 12
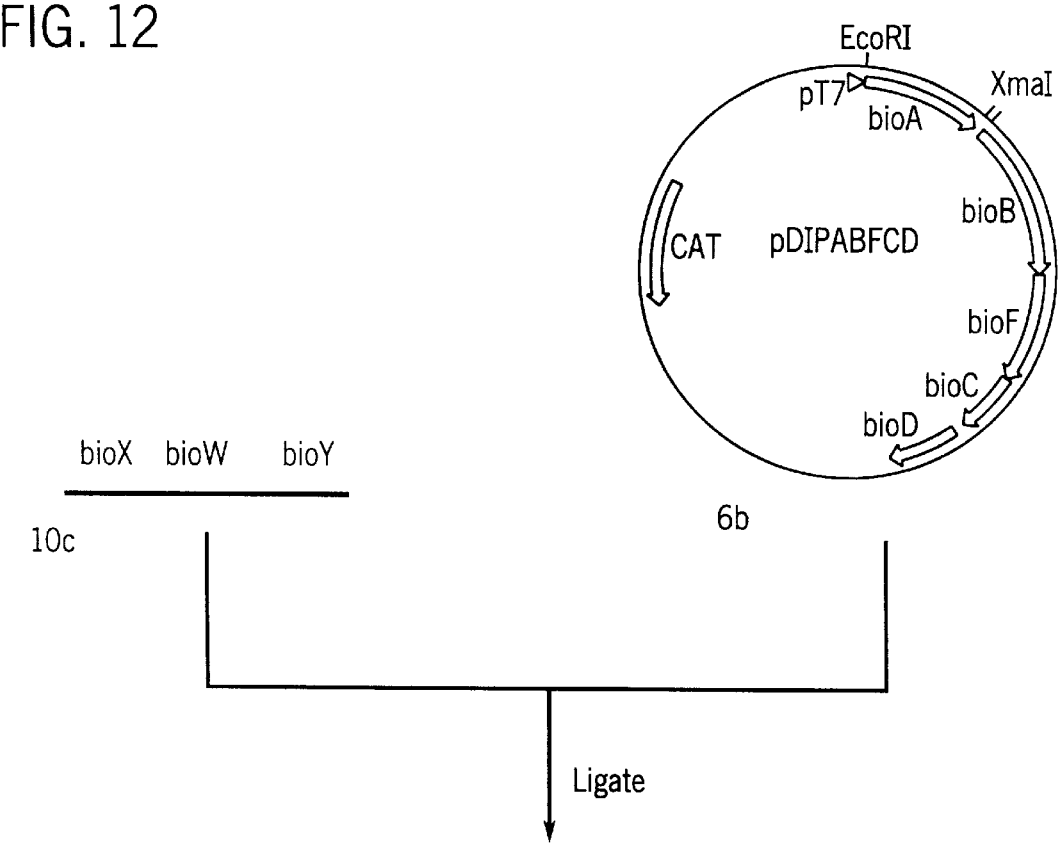
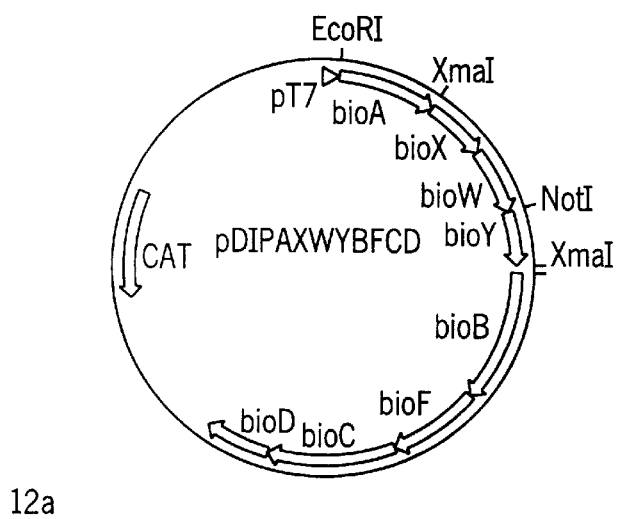

```
                          SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: YES (iv) ANTI-SENSE: NO (vi) ORIGINAL SOURCE:
         (A) ORGANISM: Escherichia coli
         (B) STRAIN: W3110

(vii) IMMEDIATE SOURCE:
         (B) CLONE: Primer #1

(ix) FEATURE:
         (A) NAME/KEY: 5'UTR
         (B) LOCATION: 1..30

(ix) FEATURE:
         (A) NAME/KEY: CDS
         (B) LOCATION: 31..35

(xi) SEQUENCE DESCRIPTION: SEQ ID NO:1:

AATCTTTTGA ATTCGGTTTA GGAGTCGATT ATGAC                                  35

(2) INFORMATION FOR SEQ ID NO:2:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: YES (iv) ANTI-SENSE: NO (vi) ORIGINAL SOURCE:
         (A) ORGANISM: Escherichia coli
         (B) STRAIN: W3110

(vii) IMMEDIATE SOURCE:
         (B) CLONE: Primer #2

(ix) FEATURE:
         (A) NAME/KEY: 3'UTR
         (B) LOCATION: complement (1..19)
```

(ix) FEATURE:
              (A) NAME/KEY: CDS
              (B) LOCATION: complement (20..24)

(xi) SEQUENCE DESCRIPTION: SEQ ID NO:2:

GCGCCACCCG GGAGAGTGAT TAAC                                                24

(2) INFORMATION FOR SEQ ID NO:3:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: YES (iv) ANTI-SENSE: NO (vi) ORIGINAL SOURCE:
              (A) ORGANISM: Escherichia coli
              (B) STRAIN: W3110

(vii) IMMEDIATE SOURCE:
              (B) CLONE: Primer #3

(ix) FEATURE:
              (A) NAME/KEY: 3'UTR
              (B) LOCATION: complement (1..12)

(ix) FEATURE:
              (A) NAME/KEY: CDS
              (B) LOCATION: complement (13..27)

(xi) SEQUENCE DESCRIPTION: SEQ ID NO:3:

GTGTGTGGTA CCTTATTGGC AAAAAAA                                             27

(2) INFORMATION FOR SEQ ID NO:4:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: YES (iv) ANTI-SENSE: NO (vi) ORIGINAL SOURCE:
              (A) ORGANISM: Escherichia coli
              (B) STRAIN: W3110

(vii) IMMEDIATE SOURCE:
              (B) CLONE: Primer #4

(ix) FEATURE:
              (A) NAME/KEY: 5'UTR
              (B) LOCATION: 1..23

(xi) SEQUENCE DESCRIPTION: SEQ ID NO:4:

TAATACGACT CACTATAGGG AGA                                                 23

(2) INFORMATION FOR SEQ ID NO:5:

(i) SEQUENCE CHARACTERISTICS:
              (A) LENGTH: 30 base pairs
              (B) TYPE: nucleic acid
              (C) STRANDEDNESS: single (D) TOPOLOGY: linear (ii) MOLECULE TYPE: DNA (genomic)

(iii) HYPOTHETICAL: YES (iv) ANTI-SENSE: NO (vi) ORIGINAL SOURCE:
        (A) ORGANISM: Escherichia coli
        (B) STRAIN: W3110

(vii) IMMEDIATE SOURCE:
        (B) CLONE: Primer #5

(ix) FEATURE:
        (A) NAME/KEY: 3'UTR
        (B) LOCATION: complement (1..22)

(ix) FEATURE:
        (A) NAME/KEY: CDS
        (B) LOCATION: complement (23..30)

(xi) SEQUENCE DESCRIPTION: SEQ ID NO:5:

CATGATGAAT TCAAGGCAAG GTTTATGTAC                                              30

(2) INFORMATION FOR SEQ ID NO:6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (vi) ORIGINAL SOURCE:
        (A) ORGANISM: Escherichia coli
        (B) STRAIN: W3110

(vii) IMMEDIATE SOURCE:
        (B) CLONE: Primer #6

(ix) FEATURE:
        (A) NAME/KEY: 5'UTR
        (B) LOCATION: 1..29

(ix) FEATURE:
        (A) NAME/KEY: CDS
        (B) LOCATION: 30..32

(xi) SEQUENCE DESCRIPTION: SEQ ID NO:6:

ATATGGGCCC AAACAAGAAA GGAGGGTTCA TG                                           32

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (vi) ORIGINAL SOURCE:
        (A) ORGANISM: Bacillus sphaericus
        (B) STRAIN: ATCC No. 10208

(vii) IMMEDIATE SOURCE:
              (B) CLONE: Primer #7

(ix) FEATURE:
              (A) NAME/KEY: 5'UTR
              (B) LOCATION: 1..25

(xi) SEQUENCE DESCRIPTION: SEQ ID NO:7:

ATATATCCCG GGTTAACTCA AATTG                                              25

(2) INFORMATION FOR SEQ ID NO:8:

(i) SEQUENCE CHARACTERISTICS:
              (A) LENGTH: 31 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: YES (iv) ANTI-SENSE: NO (vi) ORIGINAL SOURCE:
              (A) ORGANISM: Bacillus sphaericus
              (B) STRAIN: ATCC No. 10208

(vii) IMMEDIATE SOURCE:
              (B) CLONE: Primer #8

(ix) FEATURE:
              (A) NAME/KEY: 3'UTR
              (B) LOCATION: complement (1..15)

(ix) FEATURE:
              (A) NAME/KEY: CDS
              (B) LOCATION: complement (16..31)

(xi) SEQUENCE DESCRIPTION: SEQ ID NO:8:

CCCGCGGCCG CTCATTCATT TTAAATCCCC C                                       31

(2) INFORMATION FOR SEQ ID NO:9:

(i) SEQUENCE CHARACTERISTICS:
              (A) LENGTH: 31 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: YES (iv) ANTI-SENSE: NO (vi) ORIGINAL SOURCE:
              (A) ORGANISM: Bacillus sphaericus
              (B) STRAIN: ATCC No. 10208

(vii) IMMEDIATE SOURCE:
              (B) CLONE: Primer #9

(ix) FEATURE:
              (A) NAME/KEY: 5'UTR
              (B) LOCATION: 1..30

(ix) FEATURE:
              (A) NAME/KEY: CDS
              (B) LOCATION: 31

(xi) SEQUENCE DESCRIPTION: SEQ ID NO:9:

TGAATGAGCG GCCGCGGGAG GGATGAGGGC A                                       31

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (vi) ORIGINAL SOURCE:
        (A) ORGANISM: Bacillus sphaericus
        (B) STRAIN: ATCC No. 10208

(vii) IMMEDIATE SOURCE:
        (B) CLONE: Primer #10

(ix) FEATURE:
        (A) NAME/KEY: 3'UTR
        (B) LOCATION: complement (1..15)

(ix) FEATURE:
        (A) NAME/KEY: CDS
        (B) LOCATION: complement (16..27)

(xi) SEQUENCE DESCRIPTION: SEQ ID NO:10:

CTATATCCCG GGAATTCACT AAACATT 27

(2) INFORMATION FOR SEQ ID NO:11:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (iv) ANTI-SENSE: NO (vi) ORIGINAL SOURCE:
(A) ORGANISM: Bacillus sphaericus
(B) STRAIN: ATCC No. 10208

(vii) IMMEDIATE SOURCE:
(B) CLONE: Primer #11

(ix) FEATURE:
(A) NAME/KEY: 3'UTR
(B) LOCATION: complement (1..18)

(ix) FEATURE:
(A) NAME/KEY: CDS
(B) LOCATION: complement (19..29)

(xi) SEQUENCE DESCRIPTION: SEQ ID NO:11:

GATATAAGCT TCAAACAATT ATACAATCC 29

(2) INFORMATION FOR SEQ ID NO:12:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (iv) ANTI-SENSE: NO (vi) ORIGINAL SOURCE:
             (A) ORGANISM: Bacillus sphaericus
             (B) STRAIN: ATCC No. 10208

(vii) IMMEDIATE SOURCE:
             (B) CLONE: Primer #12

(ix) FEATURE:
             (A) NAME/KEY: 5'UTR
             (B) LOCATION: 1..37

(xi) SEQUENCE DESCRIPTION: SEQ ID NO:12:

TTTCCCAAGC TTTGCACACT TCTGTTTCGT ATCCTCA                                      37

(2) INFORMATION FOR SEQ ID NO:13:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (iv) ANTI-SENSE: NO (vi) ORIGINAL SOURCE:
            (A) ORGANISM: Bacillus sphaericus
            (B) STRAIN: ATCC No. 10208

(vii) IMMEDIATE SOURCE:
            (B) CLONE: Primer #13

(ix) FEATURE:
            (A) NAME/KEY: 3'UTR
            (B) LOCATION: complement (1..39)

(xi) SEQUENCE DESCRIPTION: SEQ ID NO:13:

CCTGGGAAGC TTTCATTGAA CATTTTGTGA AAACCATCA                                    39

(2) INFORMATION FOR SEQ ID NO:14:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (iv) ANTI-SENSE: NO (vi) ORIGINAL SOURCE:
            (A) ORGANISM: Escherichia coli
            (B) STRAIN: W3110

(vii) IMMEDIATE SOURCE:
            (B) CLONE: Primer #14

(ix) FEATURE:
            (A) NAME/KEY: 5'UTR
            (B) LOCATION: 1..23

(ix) FEATURE:
            (A) NAME/KEY: CDS
            (B) LOCATION: 24..41

(xi) SEQUENCE DESCRIPTION: SEQ ID NO:14:

GCTCTAGAGC AAGGAGGACA ATAATGAATA ACATCTGGTG G            41

(2) INFORMATION FOR SEQ ID NO:15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (vi) ORIGINAL SOURCE:
        (A) ORGANISM: Escherichia coli
        (B) STRAIN: W3110

(vii) IMMEDIATE SOURCE:
        (B) CLONE: Primer #15

(ix) FEATURE:
        (A) NAME/KEY: 3'UTR
        (B) LOCATION: complement (1..15)

(ix) FEATURE:
        (A) NAME/KEY: CDS
        (B) LOCATION: complement (16..36)

(xi) SEQUENCE DESCRIPTION: SEQ ID NO:15:

CCGGGTTCGA ACATCTGCT TCAACGCCAC CAGCAG            36

(2) INFORMATION FOR SEQ ID NO:16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (vi) ORIGINAL SOURCE:
        (A) ORGANISM: Escherichia coli
        (B) STRAIN: W3110

(vii) IMMEDIATE SOURCE:
        (B) CLONE: Primer #16

(ix) FEATURE:
        (A) NAME/KEY: 5'UTR
        (B) LOCATION: 1..14

(ix) FEATURE:
        (A) NAME/KEY: CDS
        (B) LOCATION: 15..31

(xi) SEQUENCE DESCRIPTION: SEQ ID NO:16:

GAAGGAGGAA AAAATGAAT AACATCTGGT G            31

(2) INFORMATION FOR SEQ ID NO:17:

(i) SEQUENCE CHARACTERISTICS:
        (A) LENGTH: 21 base pairs
        (B) TYPE: nucleic acid

```
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (vi) ORIGINAL SOURCE:
         (A) ORGANISM: Escherichia coli
         (B) STRAIN: W3110

(vii) IMMEDIATE SOURCE:
         (B) CLONE: Primer #17

(ix) FEATURE:
         (A) NAME/KEY: 3'UTR
         (B) LOCATION: complement (1..5)

(ix) FEATURE:
         (A) NAME/KEY: CDS
         (B) LOCATION: complement (6..21)

(xi) SEQUENCE DESCRIPTION: SEQ ID NO:17:

GCCACCTACA CCTGCTTCAA C                                                   21
```

METHOD TO PRODUCE BIOTIN

FIELD OF THE INVENTION

This invention relates to a method for producing biotin using recombinant cells transformed with nucleic acid sequences involved in biotin biosynthesis. In particular, this invention discloses a method to improve the ability of such recombinant cells to convert biotin vitamers to true biotin. The invention also discloses a method for improving overall biotin production.

BACKGROUND OF THE INVENTION

Biotin, or vitamin H, is an indispensable element in intermediary metabolism in many organisms since it is an essential factor of biotin-dependent carboxylases important in fatty acid synthesis, gluconeogenesis, and amino acid metabolism. Biotin is useful as a food supplement, as a cosmetic additive, and as a diagnostic reagent in biotin-avidin-based detection assays.

Most biotin for commercial use is currently produced by a complex chemical synthesis process. Although several investigators are attempting to synthesize biotin in commercial quantities using microbiological methods, the cost thus far has been prohibitive. Wild type microorganisms produce only small amounts of the vitamin apparently because such microorganisms exert tight control over biotin biosynthesis. In an effort to improve microbial biotin production, some investigators have transformed microorganisms with *Escherichia coli* or *Bacillus sphaericus* genes that encode certain proteins involved in the biotin biosynthetic pathway. Although expression of these genes in some cases did increase true biotin and/or biotin vitamer production, the amount of true biotin produced using such methods is substantially lower than that required for a commercially viable process.

The biotin biosynthetic pathway in *Escherichia coli* is thought to include at least 5 enzymatic steps catalyzed by enzymes encoded by *Escherichia coli* bioA, bioB, bioF, bioC, and bioD genes contained on the biotin operon. The *Escherichia coli* bioA, bioB, bioD, and bioF genes are thought to encode enzymes having the following respective activities: 7,8-diaminopelargonic acid aminotransferase (also called 7,8-diaminopelargonic acid synthase), biotin synthetase (also called biotin synthase), desthiobiotin synthetase (also called desthiobiotin synthase), and 7-keto-8-aminopelargonic acid synthetase (also called 7-keto-8-aminopelargonic acid synthase). The protein encoded by the *Escherichia coli* bioC gene is thought to operate at an early step in the biotin biosynthetic pathway, but the protein's actual function is presently unknown. The biotin operon also includes an additional open reading frame, referred to as *Escherichia coli* ORF 1, the function of which, until the present invention, has been unknown (e.g., Otsuka et al., pp. 19577–19585, 1988, *J. Biol. Chem.*, vol. 263; Brown et al., pp. 295–326, 1991, *Biotech. Genet. Engineer. Reviews*, vol. 9; Eisenberg, pp. 544–550, 1987, in *Escherichia coli and Salmonella typhimurium Cellular and Molecular Biology*, Neidhardt, F. C. et al., eds., American Society of Microbiology, Washington, D.C.). In addition, the *Escherichia coli* bioH gene, located at a site distant from the biotin operon, encodes a protein thought to be involved in an early, but as yet unknown, step in the biotin biosynthetic pathway (e.g., O'Regan et al., p. 8004, 1989, *Nucleic Acids Res.*, vol 17; Brown et al., ibid.

Two gene clusters encoding enzymes involved in biotin biosynthesis have been isolated from *Bacillus sphaericus*. The two gene clusters include the linked *Bacillus sphaericus* genes bioD, bioA, bioY, and bioB, also referred to as *Bacillus sphaericus* bioDAYB; and linked *Bacillus sphaericus* genes bioX, bioW, and bioF, also referred to as *Bacillus sphaericus* bioXWF (see, for example, Gloeckler et al., pp. 63–70, 1990, *Gene*, vol. 87; U.S. Pat. No. 5,096,823 by Gloeckler et al., issued Mar. 17, 1992; European Patent Office Publication No. 266,240, by Gloeckler et al., published May 4, 1988; and European Patent Publication No. 240,105, by Ohsawa et al., published Nov. 7, 1987). *Bacillus sphaericus* and *Escherichia coli* bioA, bioB, bioD, and bioF genes are structurally similar and apparently encode functionally equivalent enzymes (e.g., Brown et al., ibid.). *Bacillus sphaericus* bioW, bioX and bioY genes, which apparently are not structurally homologous to known *Escherichia coli* genes, are thought to be involved in the active uptake of pimelic acid by *Bacillus sphaericus* (e.g., Brown et al., ibid.). In contrast, some investigators have hypothesized that uptake of pimelic acid by *Escherichia coli* is by passive diffusion (e.g., Brown et al., ibid.; Ploux et al., pp. 685–690, 1992, *Biochem. J.*, vol. 287).

Several investigators have disclosed systems to attempt to express biotin using the *Escherichia coli* biotin operon. For example, GB Publication No. 2,216,530, by Pearson et al., published Oct. 11, 1989, discloses expression of the *Escherichia coli* biotin operon in *Saccharomyces cerevisiae* but does not report biotin production levels. In another example, Fisher, in U.S. Pat. No. 5,110,731, issued May 5, 1992, discloses that a biotin retention-deficient mutant of *Escherichia coli* transformed with a plasmid containing the *Escherichia coli* biotin operon produced a maximum of 30 milligrams (mg) of biotin per liter of medium.

Several researchers (see, for example, Ogata, pp. 390–394, 1970, *Methods in Enzymology*, vol. 17a; Izumi et al., pp. 231–256, in *Biotechnology of Vitamins, Pigments, and Growth Factors*, Elsevier Applied Science, E. J. Vandamme, ed.; U.S. Pat. No. 3,393,129, by Shibata et al., issued Jul. 16, 1968; and U.S. Pat. No. 4,563,426 by Yamada et al., issued Jan. 7, 1986) have reported that true biotin and biotin vitamer production by fungal and bacterial microorganisms, and in particular by *Bacillus sphaericus*, increases when the microorganisms are grown in the presence of biotin precursors, such as pimelic acid and desthiobiotin. Based upon this observation, attempts have been made to increase biotin production by transforming *Escherichia coli* and *Bacillus sphaericus* microorganisms with either the *Bacillus sphaericus* bioB gene or *Bacillus sphaericus* bioDAYB and bioXWF biotin gene clusters and growing the transformants in the presence of biotin precursors.

European Patent Publication No. 375,525, by Gloeckler et al., published Jun. 27, 1990, discloses the use of *Escherichia coli* host cells transformed with the two clusters of *Bacillus sphaericus* biotin operon genes (i.e., bioDAYB and bioXWF) to produce biotin. When such transformed hosts were grown in medium containing pimelic acid, they produced 144–160 mg of biotin vitamers per liter of medium but only 15–16 mg of true biotin per liter of medium. Thus, the amount of true biotin produced was only about 9 to 10 percent of the amount of total biotin (i.e., true biotin and vitamers) produced, indicating that, despite a high gene copy number, the transformed cells could not completely convert the biotin vitamers to true biotin. In addition, of the total amount of biotin vitamers produced, only 25 percent to 28 percent was desthiobiotin (the direct precursor of biotin), suggesting that about 70 percent of the biotin vitamers produced were compounds that had yet to be converted to desthiobiotin.

Sabatié et al., pp. 29–50, 1991, *Journal of Biotechnology*, vol. 20, also transformed *Escherichia coli* cells with a vector containing the *Bacillus sphaericus* bioDAYB and bioXWF gene clusters. When such transformed cells were grown in the presence of pimelic acid under fed-batch fermentation conditions, the cells produced 300 mg of biotin vitamers per liter of medium, but only 45 mg of true biotin per liter of medium. Thus, the amount of true biotin produced by Sabatié et al. was only 13 percent of the total amount of biotin (i.e., true biotin and vitamers) produced, again indicating inefficient conversion of biotin vitamers to true biotin.

Ohsawa et al., pp. 39–48, 1989, *Gene*, vol. 80, transformed *Escherichia coli*, *Bacillus sphaericus* and *Bacillus subtilis* with vectors containing the *Bacillus sphaericus* bioB gene under the control of suitable promoters. Transformed strains were grown in medium containing desthiobiotin. Biotin production by *Escherichia coli* and *Bacillus subtilis* cells transformed with plasmids containing the *Bacillus sphaericus* bioB gene was about 1500-fold higher than biotin production by cells transformed with plasmids lacking the *Bacillus sphaericus* bioB gene. Biotin production by *Bacillus sphaericus* cells transformed with plasmids containing the *Bacillus sphaericus* bioB gene was about 100-fold higher than biotin production by cells transformed with plasmids lacking the *Bacillus sphaericus* bioB gene.

Ohsawa et al., pp. 121–124, 1992, *J. Ferment. Bioeng.*, vol. 73, also cultured *Bacillus sphaericus* cells transformed with a plasmid containing the *Bacillus sphaericus* bioB gene in medium containing pimelic acid. Cells transformed with a plasmid lacking the *Bacillus sphaericus* bioB gene made less than 0.2 mg of true biotin per liter of medium and about 25 mg of vitamers and true biotin per liter of medium. Cells transformed with a plasmid containing the *Bacillus sphaericus* bioB gene made about 1.2–3.5 mg of true biotin per liter of medium and about 30 mg of vitamers and true biotin per liter of medium. Thus, despite the increased expression of the *Bacillus sphaericus* bioB gene, only 4 percent to 10.4 percent of the total amount of biotin (i.e., biotin vitamers and true biotin) produced was true biotin.

Additional attempts to increase biotin production have included efforts to obtain hosts that are derepressed for biotin synthesis (see, for example, Japanese Patent Publication No. 62,155,081, assigned to Shiseido KK, published Jul. 10, 1987; Japanese Patent Publication No. 61,202,686, assigned to Shiseido KK, published Sep. 8, 1986; Japanese Patent Publication No. 61,149,091, assigned to Nippon Soda KK, published Jul. 7, 1986; and European Patent Publication No. 379,442, by Gloeckler et al., published Jul. 25, 1990), and to obtain low-acetate synthesizing mutants (see, for example, European Patent Publication No. 316,229, by Haze et al., published May 17, 1989). However, none of these techniques has led to the production of commercially significant amounts of true biotin.

Thus there remains both a need to improve overall biotin production by amplifying expression of additional genes in the biotin biosynthetic pathway and to improve production of true biotin by engineering cells to convert biotin vitamers to true biotin.

SUMMARY OF THE INVENTION

The present invention is directed to a method to produce biotin in which biotin vitamers are efficiently converted into true biotin by transforming host cells with nucleic acid sequences encoding enzymes involved in biotin biosynthesis. For example, cells transformed with at least an *Escherichia coli* bioH gene or functional equivalent thereof can produce increased amounts of biotin. Additionally, unprecedented yields of true biotin, particularly due to increased conversion of biotin vitamers to true biotin, can be obtained by culturing, in an effective medium, cells transformed with at least an *Escherichia coli* bioE gene or functional equivalent thereof.

The present invention includes a biotin-producing recombinant cell transformed with an *Escherichia coli* bioE gene or a functional equivalent thereof, either alone or in combination with at least one nucleic acid sequence selected from *Bacillus sphaericus* bioA, bioB, bioD, bioF, bioW, bioX, and bioY genes, or functional equivalents thereof (i.e., a functional equivalent of any of the aforementioned genes or nucleic acid sequences). Preferably, recombinant cells of the present invention are bacterial or yeast cells; preferably of the genus Escherichia, Bacillus, Pseudomonas, Salmonella, Corynebacterium, or Saccharomyces; more preferably of the species *Escherichia coli*, *Bacillus sphaericus*, or *Bacillus subtilis*; and even more preferably of the species *Escherichia coli*. Recombinant cells are preferably produced by transforming recombinant molecules of the present invention into host cells. Recombinant molecules of the present invention are formed by operatively linking nucleic acid sequences of the present invention to expression vectors containing at least one transcription control sequence functional in the respective cell to be transformed. Particularly preferred transcription control sequences include bacteriophage T7 transcription control sequences.

The present invention further relates to a recombinant cell, other than *Escherichia coli*, transformed with an *Escherichia coli* bioE gene or a functional equivalent thereof. Such a recombinant cell, preferably of the genus Bacillus, can also be transformed with at least one nucleic acid sequence selected from the group consisting of *Bacillus sphaericus* bioA, bioB, bioD, bioF, bioW, bioX, and bioY genes, *Escherichia coli* bioA, bioB, bioC, bioD, bioF, and bioH genes, and functional equivalents of any of such genes.

One aspect of the present invention is the use of recombinant cells of the present invention to produce biotin by culturing such cells under appropriate conditions in a medium effective for the production of biotin, and recovering biotin therefrom. Preferably, the effective medium is supplemented with at least one biotin precursor, or derivative thereof, which can be efficiently converted to true biotin by the recombinant cell, thereby increasing the amount of true biotin produced by the recombinant cell. Preferred supplements include dicarboxylic acids, such as pimelic acid and azelaic acid; biotin vitamers; derivatives thereof; and mixtures thereof. A particularly preferred biotin precursor supplement is a compound that is produced by a reaction in the biotin biosynthetic pathway occurring prior to the reactions carried out by enzymes encoded by the genes transformed into the recombinant cell being cultured. For example, a particularly preferred effective medium for a recombinant cell transformed with *Escherichia coli* bioE, and *Bacillus sphaericus* bioB, bioD, bioA, bioF, bioW, bioX, and bioY genes, or functional equivalents thereof, is a medium supplemented with pimelic acid or a derivative thereof. A particularly preferred effective medium for a recombinant cell transformed with *Escherichia coli* bioE, and *Bacillus sphaericus* bioB, bioD, and bioA, or functional equivalents thereof, is a medium supplemented with 2-keto-8-aminopelargonic acid or a derivative thereof. A particularly preferred effective medium for a recombinant cell transformed with *Escherichia coli* bioE, and *Bacillus sphaericus* bioB, and bioD, or functional equivalents thereof, is a medium supplemented with 7,8-diaminopelargonic acid or a derivative thereof.

Recombinant cells of the present invention are especially useful for their ability to efficiently convert biotin vitamers to true biotin. When cultured in an effective medium, such cells are capable of producing biotin such that at least about 25 percent of the total biotin (i.e., true biotin and biotin vitamers) produced is true biotin. Preferably at least about 50 percent, more preferably at least about 75 percent, and even more preferably at least about 90 percent, of the total biotin produced using such cells is true biotin. Particularly preferred recombinant cells produce essentially about 100 percent true biotin.

Another aspect of the present invention is a recombinant cell transformed with an *Escherichia coli* bioH gene, or functional equivalent thereof, such a recombinant cell being capable of producing more biotin than a cell not transformed with an *Escherichia coli* bioH gene, or functional equivalent thereof. The recombinant cell can also be transformed with at least one nucleic acid sequence selected from the group consisting of *Escherichia coli* bioA, bioB, bioC, bioD, bioE, and bioF genes, and functional equivalents thereof.

The present invention also includes recombinant molecules containing an *Escherichia coli* bioH gene, or functional equivalent thereof, either alone or with at least one of the aforementioned nucleic acid sequences; a method to produce such a recombinant cell; and use of such a cell to produce biotin by culturing the cell in an effective medium and recovering biotin produced thereby.

BRIEF DESCRIPTION OF FIGURES

FIGS. 10 through 15 contain schematic drawings of methods to produce certain nucleic acid sequences containing *Bacillus sphaericus* genes and certain recombinant molecules containing *Escherichia coli* and *Bacillus sphaericus* genes encoding enzymes involved in biotin production.

DETAILED DESCRIPTION OF THE INVENTION

Figure 1:
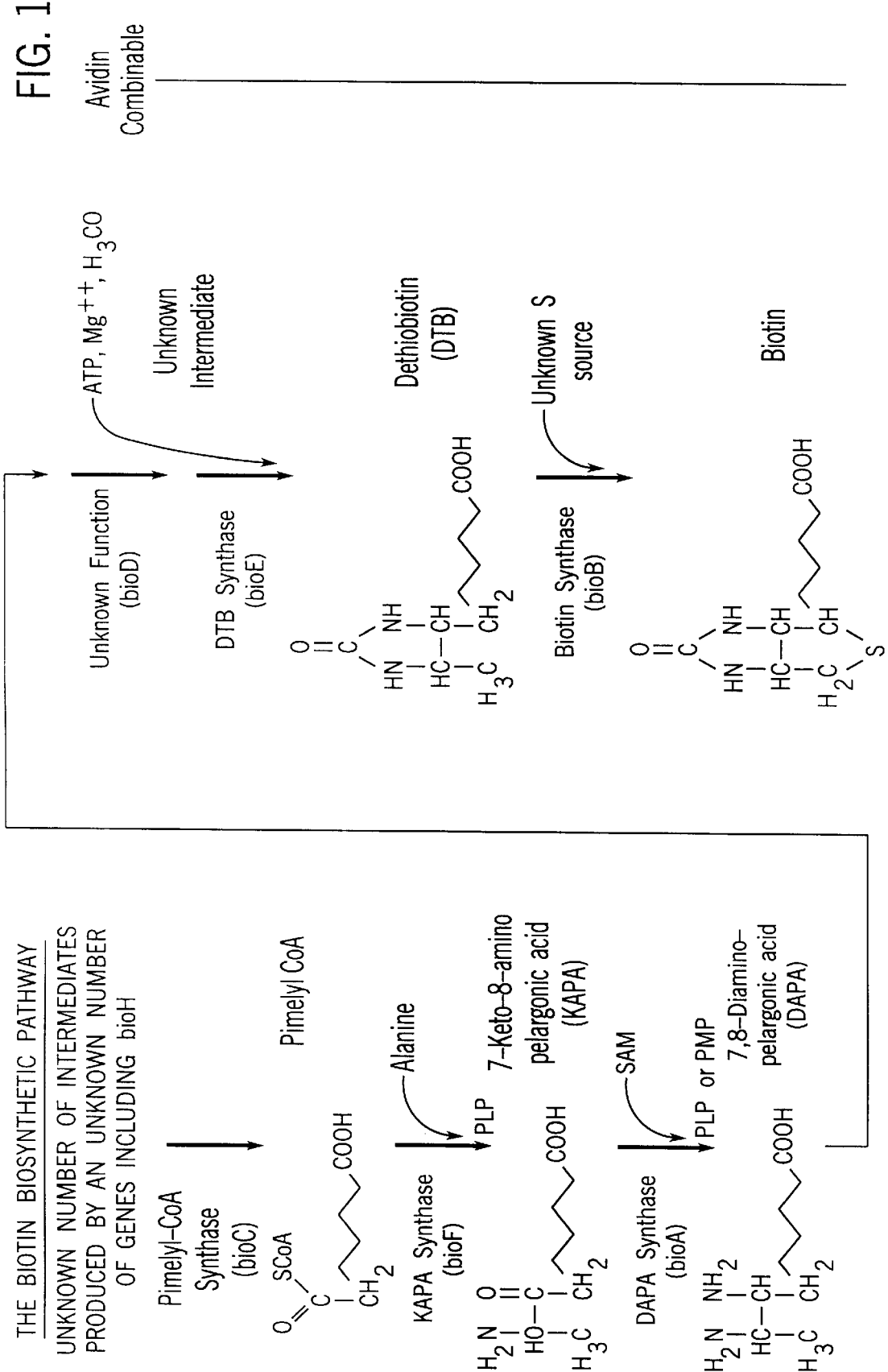
FIG. 1 is a schematic illustration of the enzymatic steps believed to be involved in the *Escherichia coli* biotin biosynthetic pathway.

One aspect of the present invention is directed to a method to efficiently convert biotin vitamers to true biotin by introducing into a cell a gene that, until now, had not been recognized for its importance in biotin biosynthesis. Use of such a gene is particularly applicable to microorganisms which tend to accumulate biotin vitamers, such as but not limited to 7-keto-8-aminopelargonic acid and 7,8-diaminopelargonic acid. As used herein, the terms "biotin" and "total biotin" include the entire spectrum of biotin and biotin vitamer molecules that can be utilized by *Saccharomyces cerevisiae* (see, for example, Ogata et al., pp. 889–894, 1965, *Agr. Biol. Chem.,* vol. 29). As such, "biotin" and "total biotin" include both biotin vitamers and true biotin. As used herein, the term "true biotin" refers to a compound having the chemical structure of vitamin H, as well as any compound that shares substantial functional attributes and characteristics thereof. True biotin molecules are capable of supporting the growth of *Lactobacillus arabinosus* (see, for example, Ogata et al., ibid). As used herein, the term "biotin vitamers" include those vitamers that are utilized by *Saccharomyces cerevisiae* but that do not support the growth of *Lactobacillus arabinosus*.

One embodiment of the present invention is the identification of ORF 1 of the *Escherichia coli* biotin operon as a gene encoding a key enzyme in the biotin biosynthetic pathway. This gene, referred to in the present application as the *Escherichia coli* bioE gene, encodes desthiobiotin synthetase activity, an enzyme previously thought to be encoded by the bioD gene. The present invention shows, for example, that cells transformed with *Escherichia coli* bioA, bioB, bioF, bioC, and bioD genes, or with *Bacillus sphaericus* bioB, bioD, bioA, bioF, bioW, bioX, and bioY genes, produce primarily biotin vitamers unless such cells are also transformed with an *Escherichia coli* bioE gene, or a functional equivalent thereof. Thus, the *Escherichia coli* bioE gene, or a functional equivalent thereof, can be used to improve biotin production, and particularly the conversion of biotin vitamers to true biotin, in a number of microorganisms as disclosed hereinafter. The inventors believe that, even though a large amount of research has been conducted on the various genes and enzymes of the biotin biosynthetic pathway, the function of the *Escherichia coli* bioE gene has remained unappreciated.

As used herein, reference to a "gene" means the natural gene itself as well as any functionally equivalent nucleic acid sequences thereof, including, but not limited to, insertions, substitutions, deletions and/or inversions of nucleotides which have substantially no effect on the primary functional characteristics of the product encoded by the gene. A functional equivalent of the *Escherichia coli* bioE gene, therefore, is any gene which encodes an enzyme having an essentially similar activity as the enzyme encoded by the *Escherichia coli* bioE gene (i.e., any gene which encodes an active desthiobiotin synthetase). A functional equivalent of the *Escherichia coli* bioE gene can be isolated from any biotin-producing organism, such as, but not limited to, *Bacillus sphaericus, Bacillus subtilis,* other bacteria, and yeast. A functional equivalent of the *Escherichia coli* bioE gene also includes nucleic acid sequences containing, for example, nucleotide deletions, additions, substitutions, and/or inversions that do not substantially interfere with the nucleic acid sequence's ability to encode an enzyme capable of desthiobiotin synthetase activity.

Use of an *Escherichia coli* bioE gene or a functional equivalent thereof is particularly effective when the gene is co-expressed with the *Bacillus sphaericus* biotin operon gene clusters bioDAYB and bioXWF, since overexpression of the *Bacillus sphaericus* gene clusters in either *Bacillus sphaericus* or *Escherichia coli* without the bioE gene leads predominantly to the production of biotin vitamers rather than of true biotin. According to the present invention, high levels of expression of the bioE gene concomitant with high levels of expression of the *Bacillus sphaericus* biotin gene clusters or functional equivalents thereof, increases conversion of biotin vitamers to true biotin, thereby improving true biotin production.

The function of the protein encoded by the *Escherichia coli* bioE gene, as identified by the inventors, can be determined using a number of different methods. Such methods include genetic manipulation of genes encoding enzymes involved in biotin biosynthesis and phenotypic complementation assays.

One aspect of the present invention is the isolation and manipulation of DNA fragments containing either the entire *Escherichia coli* biotin operon or portions thereof in order to determine the function of the protein encoded by the *Escherichia coli* bioE gene. The *Escherichia coli* biotin operon can be isolated using standard techniques described in detail by Sambrook et al., *Molecular Cloning: A Laboratory Manual*, Cold Spring Harbor Labs Press, 1989, which is incorporated herein by reference in its entirety. Expression vectors are constructed that contain the *Escherichia coli* biotin operon genes bioA, bioB, bioF, bioC, and bioD, with or without the bioE gene. These constructs are referred to, respectively, as pAEBFCD and pABFCD. For example, in one embodiment of the present invention, the biotin operon genes comprising pAEBFCD and pABFCD are placed in pDIP18 expression vectors to form pDIPAEBFCD and pDIPABFCD, respectively, in which expression of the genes is controlled by the bacteriophage T7 promoter. In another embodiment, the biotin operon genes comprising pAEBFCD and pABFCD are placed in pUC18 expression vectors to form pUCAEBFCD and pUCABFCD, respectively.

The function of the protein encoded by the *Escherichia coli* bioE gene can be analyzed by transforming *Escherichia coli* cells with either pAEBFCD or pABFCD and culturing the resultant transformed cells in a medium effective to promote biotin production (e.g., LB broth). Following culturing, total biotin, true biotin, and biotin vitamer production levels can be measured in a variety of ways known to one skilled in the art including, but not limited to, microbiological, chromatographic, and chemical assays. Cells transformed with pABFCD produce mostly biotin vitamers, whereas cells transformed with pAEBFCD produce mostly true biotin. Thus, the *Escherichia coli* bioE gene appears to encode a protein that is important in the conversion of biotin vitamers to true biotin.

The function of the protein encoded by the *Escherichia coli* bioE gene can also be determined using phenotypic complementation assays. For example, cross-feeding studies can be used to determine if the *Escherichia coli* bioE gene can restore biotin production in individual biotin auxotrophs. Separate plates containing biotin-free nutrient agar (e.g., M9 minimal medium containing vitamin-free amino acids, thiamine, and agar) are streaked with either *Escherichia coli* bioD$^-$ or *Escherichia coli* bioB$^-$ cells. The plates are then cross-streaked with the following *Escherichia coli* strains: bioD$^-$ cells, bioB$^-$ cells, bioC$^-$ cells, bioF$^-$ cells, bioA$^-$ cells, cells lacking the biotin operon (e.g., *Escherichia coli* SA291 cells) that have been transformed with pAEBFCD (e.g., *Escherichia coli* SA291-pUCAEBFCD cells); or cells lacking the biotin operon (e.g., *Escherichia coli* SA291 cells) that have been transformed with pABFCD (e.g., *Escherichia coli* SA291-pUCABFCD cells). The ability of *Escherichia coli* bioD$^-$ or bioB$^-$ cells to cross-feed each strain is determined by visual inspection. *Escherichia coli* bioD$^-$ cells were found to be incapable of cross-feeding *Escherichia coli* bioB$^-$ cells or *Escherichia coli* SA291-pABFCD cells. *Escherichia coli* bioB$^-$ cells, however, were capable of cross-feeding SA291-pABFCD cells and bioD$^-$ cells. Both *Escherichia coli* bioD$^-$ and bioB$^-$ cells were able to cross-feed bioC$^-$, bioF$^-$, and bioA$^-$ cells. Thus, referring to FIG. 1, it is apparent that the *Escherichia coli* bioE gene encodes an enzyme active in the biotin biosynthesis pathway prior to the activity of the enzyme encoded by the *Escherichia coli* bioB gene and following the activity of the enzyme encoded by the *Escherichia coli* bioD gene.

That the enzyme encoded by the *Escherichia coli* bioE gene has desthiobiotin synthetase activity is supported by the finding that the *Escherichia coli* bioE gene encodes an enzyme that catalyzes the production of a compound that has properties characteristic of desthiobiotin, such as stability and ability to combine with avidin. In contrast, the compound produced in a reaction catalyzed by the *Escherichia coli* bioD gene product is labile and is not capable of binding to avidin.

One embodiment of the present invention is a recombinant cell transformed with an *Escherichia coli* bioE gene, or a functional equivalent thereof, alone or in combination with at least one nucleic acid selected from the group consisting of *Bacillus sphaericus* bioA, bioB, bioD, bioF, bioW, bioX, and bioY genes, and functional equivalents thereof. Preferably, the recombinant cell is cultured in an effective medium so as to produce biotin such that at least about 25 percent of the aggregate production of true biotin and biotin vitamers by the cell is true biotin. As used herein, a "functional equivalent" of a particular nucleic acid sequence (e.g., a gene) is a nucleic acid sequence that encodes a protein having substantially the same biological function as the protein encoded by the particular nucleic acid sequence. It is within the scope of the present invention to isolate and use a functionally equivalent nucleic acid sequence obtained or derived from any biotin-producing microorganism. For example, functional equivalents of a *Bacillus sphaericus* bioB gene include nucleic acid sequences isolated from any biotin-producing microorganism that encode an enzyme with biotin synthetase activity. Thus, a functional equivalent of the *Bacillus sphaericus* bioB gene can be an *Escherichia coli* bioB gene.

In addition, functionally equivalent nucleic acid sequences can include nucleic acid sequences containing modifications, such as nucleotide deletions, additions, substitutions, and/or inversions that do not substantially interfere with the nucleic acid sequence's ability to encode a biologically active enzyme. That is, functionally equivalent nucleic acid sequences of the present invention encode enzymes having a biological activity similar to their natural counterparts. Functionally equivalent eukaryotic nucleic acid sequences can also include intervening and/or untranslated sequences surrounding and/or within the coding regions of the nucleic acid sequences.

A functionally equivalent nucleic acid sequence can be obtained using methods known to those skilled in the art (see, for example, Sambrook et al., ibid.). For example, nucleic acid sequences can be modified using a variety of techniques including, but not limited to, classic mutagenesis techniques and recombinant DNA techniques, such as site-directed mutagenesis, chemical treatment of a nucleic acid to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid sequences, and combinations thereof. Functionally equivalent nucleic acids can be selected from a mixture of modified nucleic acid sequences by screening for the function of the protein encoded by the nucleic acid sequence. A number of screening techniques are known to those skilled in the art including, but not limited to, complementation assays, binding assays, and enzyme assays. In one embodiment, a nucleic acid sequence that is functionally equivalent to the *Escherichia coli* bioE gene can be selected by its ability to complement an *Escherichia coli* strain that lacks a functional bioE gene. For example, a nucleic acid sequence functionally equivalent to the *Escherichia coli* bioE gene from a bacterial or yeast strain can be selected by transforming a microorganism (preferably *Escherichia coli*) that lacks a functional bioE gene with a genomic library prepared from that strain and isolating nucleic acid sequences that enable such a microorganism to grow in the absence of biotin.

Nucleic acid sequences of the present invention can be from any biotin-producing cell, such as but not limited to any bacterial, yeast, other fungal, insect, animal, or plant cell that produces biotin. Bacterial and yeast cells are preferred sources of nucleic acid sequences. More preferred sources are Escherichia, Bacillus, Pseudomonas, Salmonella, Corynebacterium, or Saccharomyces, with *Escherichia coli*, *Bacillus sphaericus,* and *Bacillus subtilis,* being more preferred. Particularly preferred nucleic acid sequences of the present invention are the bioA, bioB, bioC, bioD, bioE, bioF, and bioH genes of *Escherichia coli* and the bioA, bioB, bioD, bioF, bioW, bioX, and bioY genes of *Bacillus sphaericus*.

A preferred recombinant cell of the present invention is a cell transformed with an *Escherichia coli* bioE gene, or a functional equivalent thereof, alone or in combination with at least one nucleic acid selected from the group consisting of *Bacillus sphaericus* bioA, bioB, bioD, bioF, bioW, bioX, and bioY genes, and functional equivalents thereof, such that at least one of the nucleic acid sequences is a *Bacillus sphaericus* nucleic acid sequence (i.e., it has the nucleic acid sequence of a *Bacillus sphaericus* nucleic acid sequence). Preferably, such a recombinant cell is not transformed with a nucleic acid sequence containing the entire *Escherichia coli* biotin operon (e.g., the HindIII/EcoRI restriction fragment found in lambda bio-transducing phage bioT124; Guha et al., pp. 53–62, 1971, *J. Mol. Biol.,* Vol. 56), especially if the cell is cultured in an effective medium supplemented with pimelic acid, or a derivative thereof, to produce biotin.

Preferred combinations of nucleic acid sequences with which to transform a host cell include the *Escherichia coli* bioE gene or a functional equivalent thereof (denoted E herein) in combination with at least one of the following nucleic acid sequences: (a) a *Bacillus sphaericus* bioB gene or a functional equivalent thereof (denoted B herein); (b) a *Bacillus sphaericus* bioD gene or a functional equivalent thereof (denoted D herein); (c) a *Bacillus sphaericus* bioA gene or a functional equivalent thereof (denoted A herein); (d) a *Bacillus sphaericus* bioF gene or a functional equivalent thereof (denoted F herein); (e) a *Bacillus sphaericus* bioW gene or a functional equivalent thereof (denoted W herein); (f) a *Bacillus sphaericus* bioX gene or a functional equivalent thereof (denoted X herein); and (g) a *Bacillus sphaericus* bioY gene or a functional equivalent thereof (denoted Y herein). These nucleic acid sequences can be transformed into the host cell on one or more recombinant molecules, as described further hereinafter.

Another embodiment of the present invention is a recombinant cell transformed with an *Escherichia coli* bioH gene or functional equivalent thereof (denoted H herein) alone or in combination with at least one of the following nucleic acid sequences: (a) an *Escherichia coli* bioB gene or a functional equivalent thereof (denoted B, as above, since *Escherichia coli* bioB and *Bacillus sphaericus* bioB genes are functional equivalents); (b) an *Escherichia coli* bioE gene or a functional equivalent thereof (denoted E herein); (c) an *Escherichia coli* bioD gene or a functional equivalent thereof (denoted D herein); (d) an *Escherichia coli* bioA gene or a functional equivalent thereof (denoted A herein); (e) an *Escherichia coli* bioF gene or a functional equivalent thereof (denoted F herein); and (f) an *Escherichia coli* bioC gene or a functional equivalent thereof (denoted C herein). These nucleic acid sequences can be transformed into the host cell on one or more recombinant molecules, as described further hereinafter. Preferably, a recombinant cell transformed with an *Escherichia coli* bioH gene, or functional equivalent thereof, is capable of producing more biotin than a cell not transformed with an *Escherichia coli* bioH gene, or functional equivalent thereof.

Preferred nucleic acid sequence combinations using genes and nucleic acid sequences with the aforementioned notations include, but are not limited to, E, EB, EBD, EBDA, EBDAF, EBDAFWXY, H, BH, EH, BEH, BEDH, BEDAH, BEDAFH, and BEDAFCH. Note that the order of the denoted genes/nucleic acid sequences as presented is not limited to that order but can be any permutation thereof. In addition, the genes/nucleic acid sequences can be introduced into cells on one or more recombinant molecules. While it is critical that the genes and nucleic acid sequences of the present invention be expressed into functional proteins, the method and sequence by which the genes/nucleic acid sequences are introduced into a cell are not critical. Furthermore, each of the denoted genes/nucleic acid sequences can be isolated from any biotin-producing microorganism. In one preferred embodiment of the present invention, E, C, and H genes are isolated from *Escherichia coli* and B, D, A, F, W, X, and Y genes are isolated from *Bacillus sphaericus.* In a second preferred embodiment, E, B, D, A, F, C, and H genes are isolated from *Escherichia coli* and W, X, and Y genes are isolated from *Bacillus sphaericus.*

Particularly preferred combinations of *Escherichia coli* and *Bacillus sphaericus* nucleic acid sequences with which to transform cells in order to improve biotin production, and particularly true biotin production are summarized in Table 1. Table 1 uses the aforementioned notations in that the capital letters E, B, D, A, F, C, H, W, X, and Y denote bioE, bioB, bioD, bioA, bioF, bioC, bioH, bioW, bioX, and bioY genes, respectively (e.g., E represents bioE). The term "$^{col}$" indicates nucleic acid sequences that are isolated from *Escherichia coli* cells (e.g., $E^{col}$ is a bioE gene from *Escherichia coli*) and "$^{sph}$" indicates nucleic acid sequences isolated from *Bacillus sphaericus* cells. The order of the genes is illustrative and can be any permutation thereof. It will also be understood that while Table 1 specifically denotes the genus and species from which particular genes are derived, the present invention encompasses all functional equivalents of such genes and combinations thereof.

TABLE 1

Preferred Combinations of Nucleic Acid Sequences with which to Transform Cells $E^{col}$
$E^{col}B^{sph}$
$E^{col}B^{sph}D^{sph}$
$E^{col}B^{sph}D^{sph}A^{sph}$
$E^{col}B^{sph}D^{sph}A^{sph}F^{sph}$
$E^{col}B^{sph}D^{sph}A^{sph}F^{sph}W^{sph}X^{sph}Y^{sph}$
$E^{col}B^{col}$
$E^{col}B^{col}D^{col}$
$E^{col}B^{col}D^{col}A^{col}$
$E^{col}B^{col}D^{col}A^{col}F^{col}$
$E^{col}B^{col}D^{col}A^{col}F^{col}W^{sph}X^{sph}Y^{sph}$ TABLE 1-continued Preferred Combinations of Nucleic Acid Sequences
with which to Transform Cells $E^{col}B^{col}D^{col}A^{col}F^{col}C^{col}W^{sph}X^{sph}Y^{sph}$
$E^{col}B^{col}D^{col}A^{col}F^{col}H^{col}W^{sph}X^{sph}Y^{sph}$
$E^{col}B^{col}D^{col}A^{col}F^{col}C^{col}H^{sph}W^{sph}X^{sph}Y^{sph}$
$H^{col}$
$B^{col}H^{col}$
$E^{col}H^{col}$
$E^{col}B^{col}H^{col}$
$E^{col}B^{col}D^{col}H^{col}$
$E^{col}B^{col}D^{col}A^{col}H^{col}$
$E^{col}B^{col}D^{col}A^{col}F^{col}H^{col}$
$E^{col}B^{col}D^{col}A^{col}F^{col}C^{col}H^{col}$ The present invention includes recombinant molecules containing the *Escherichia coli* bioE gene, or a functional equivalent thereof, operatively linked to an expression vector comprising one or more transcription control sequences. Recombinant molecules of the present invention can also include at least one nucleic acid sequence selected from *Bacillus sphaericus* bioA, bioB, bioD, bioF, bioW, bioX, and bioY genes, or a functional equivalent of any of these genes, operatively linked to one or more transcription control sequences.

Another embodiment includes recombinant molecules containing the *Escherichia coli* bioH gene, or a functional equivalent thereof, operatively linked to an expression vector comprising one or more transcription control sequences. Such recombinant molecules can also include at least one nucleic acid sequence selected from *Escherichia coli* bioA, bioB, bioC, bioD, bioE, and bioF genes, or a functional equivalent of any of these genes, operatively linked to one or more transcription control sequences.

Recombinant molecules of the present invention can contain one or more nucleic acid sequences of the present invention. For example, to transform a cell with the nucleic acid sequence combination $E^{col}D^{sph}A^{sph}Y^{sph}B^{sph}X^{sph}W^{sph}F^{sph}$, one can transform the cell with: a single recombinant molecule containing $E^{col}D^{sph}A^{sph}Y^{sph}B^{sph}X^{sph}W^{sph}F^{sph}$; with two recombinant molecules in which the first recombinant molecule contains a nucleic acid sequence $E^{col}D^{sph}A^{sph}Y^{sph}B^{sph}$ and the second recombinant molecule contains a nucleic acid sequence $X^{sph}W^{sph}F^{sph}$; or with multiple recombinant molecules containing other combinations of the nucleic acid sequences.

As used herein, the phrase "operatively linked" refers to insertion of a nucleic acid sequence into an expression vector in a manner such that the sequence is able to be expressed when transformed into a host cell. As used herein, an expression vector is a DNA or RNA vector that is capable of transforming a host cell, of replicating within the host cell, and of effecting expression of a specified nucleic acid sequence. Expression vectors can be either prokaryotic or eukaryotic, and are typically viruses or plasmids. Preferred expression vectors of the present invention can include, but are not limited to, any vectors that direct gene expression in bacterial and/or yeast host cells. More preferred expression vectors can direct gene expression in cells of the genus Escherichia, Bacillus, Pseudomonas, Salmonella, Corynebacterium, and/or Saccharomyces. Even more preferred expression vectors direct gene expression in cells of the species *Escherichia coli, Bacillus sphaericus,* and/or *Bacillus subtilis.* Particularly preferred expression vectors are those that function (e.g., direct gene expression) in *Escherichia coli,* such as pDIP18, pUC18, and pCKR101 expression vectors.

Nucleic acid sequences of the present invention can be operatively linked to expression vectors containing regulatory sequences such as promoters, operators, repressors, enhancers, termination sequences, origins of replication, and other regulatory sequences that are compatible with the host cell and that control the expression of the nucleic acid sequences. In particular, expression vectors of the present invention include transcription control sequences. Transcription control sequences are sequences which control the initiation, elongation, and termination of transcription. Particularly important transcription control sequences are those which control transcription initiation, such as, but not limited to, promoter, enhancer, operator and repressor sequences. Preferred transcription control sequences include, but are not limited to, any transcription control sequences that are able to control transcription in bacteria and/or yeast. More preferred transcription control sequences include those which function in Escherichia, Bacillus, Pseudomonas, Salmonella, Corynebacterium, and/or Saccharomyces. Even more preferred transcription control sequences include, but are not limited to, tac, lac, trp, trc, oxy-pro, lambda, bacteriophage T7, bacteriophage T3, bacteriophage SP6, bacteriophage SP01, metallothionein (e.g., CUP1), alpha mating factor, and Pichia alcohol oxidase transcription control sequences. Even more preferred transcription control sequences are bacteriophage T7, tac, and lac transcription control sequences. One preferred expression vector is pCKR101 (Magnuson et al., pp. 262–266, 1992, *FEBS Letters,* vol. 299) contains a tac transcription control sequence. Another preferred expression vector, pUC18 (available from GIBCO BRL, Gaithersburg, Md.), contains a lac transcription control sequence. Both tac and lac transcription control sequences contain an operator sequence that is regulated by the lac repressor. Thus, expression from any of these expression vectors can be induced by, for example, isopropyl-β-D-thiogalactoside (IPTG). Yet another preferred expression vector is pDIP18 (obtained from Dr. L. Gold, University of Colorado, Boulder, Colo.). pDIP18 contains a bacteriophage T7 promoter, which is recognized essentially only by bacteriophage T7 RNA polymerase.

It is within the scope of the present invention that transcription control sequences can include both nucleic acid sequences, such as promoters, operators, and enhancers, as well as genes encoding RNA polymerases that recognize and initiate transcription from such signals, and genes encoding repressors that interact with the operators. For example, a bacteriophage T7 promoter and a gene encoding a bacteriophage T7 polymerase may be contained either on a plasmid or integrated into the host genome. As an illustrative example, pDIP18, which contains a bacteriophage T7 promoter, can be transformed into a cell in which a gene encoding a bacteriophage T7 RNA polymerase operatively linked to an IPTG-inducible transcription control sequence has been integrated into the cell's chromosomal DNA.

Transcription control sequences of the present invention can include naturally occurring transcription control sequences previously associated with a nucleic acid sequence prior to isolation. For example, such transcription control sequences can include sequences associated with genes encoding enzymes involved in biotin biosynthesis. Since such transcription control sequences are usually subject to biotin regulation, such sequences are preferably used in cells in which biotin biosynthesis is deregulated (e.g., cells in which biotin production is no longer repressed by high concentrations of biotin, or by precursors or analogs thereof).

According to the present invention, nucleic acid sequences encoding one or more enzymes involved in biotin biosynthesis can be linked (a) individually, (b) as a group, or (c) as a combination thereof to transcription control sequences. The transcription control sequences can be identical or different for the different genes/nucleic acid sequences of the present invention. For example, all desired genes can be linked to a single transcription control sequence or some of the genes can be linked to one transcription control sequence and other genes to a second transcription control sequence.

A recombinant molecule of the present invention can be any nucleic acid sequence combination heretofore described operatively linked to any transcription control sequence capable of effectively regulating expression of the nucleic acid sequence in the cell to be transformed. Preferred recombinant molecules contain the nucleic acid sequence combinations E, EB, EBD, EBDA, EBDAF, EBDAFWXY, H, BH, EH, BEH, BEDH, BEDAH, BEDAFH, and BEDAFCH operatively linked to at least one transcription control sequence, and preferably to at least one bacteriophage T7, tac, and/or lac transcription control sequence. In all cases, the order of the genes is illustrative and can be any permutation thereof. More preferred recombinant molecules contain the nucleic acid sequence combinations described in Table 1 operatively linked to one or more transcription control sequences. Such nucleic acid sequences preferably are operatively linked to an expression vector containing a tac transcription control sequence (e.g., pCKR101), to an expression vector containing a lac transcription control sequence (e.g., pUC18), or, more preferably, to an expression vector containing a bacteriophage T7 transcription control sequence (e.g., pDIP18) for expression in Escherichia coli cells, and to a bacteriophage SP01 transcription control sequence for expression in Bacillus cells. Even more preferred combinations of recombinant molecules contain the nucleic acid sequences $E^{col}$, $E^{col}B^{sph}$, $E^{col}B^{sph}D^{sph}$, $E^{col}B^{sph}D^{sph}A^{sph}$, $E^{col}B^{sph}D^{sph}A^{sph}F^{sph}$, $E^{col}B^{sph}D^{sph}A^{sph}F^{sph}W^{sph}X^{sph}Y^{sph}$, $E^{col}B^{col}D^{col}A^{col}F^{col}W^{sph}X^{sph}Y^{sph}$, $H^{col}$, or $E^{col}B^{col}D^{col}A^{col}F^{col}C^{col}H^{col}$ operatively linked to a bacteriophage T7, tac, or lac transcription control sequence, and preferably to a bacteriophage T7 transcription control sequence. Even more preferred recombinant molecules contain the nucleic acid sequences $E^{col}B^{sph}D^{sph}A^{sph}F^{sph}W^{sph}X^{sph}Y^{sph}$, $E^{col}B^{col}D^{col}A^{col}F^{col}W^{sph}X^{sph}Y^{sph}$, or $E^{col}B^{col}D^{col}A^{col}F^{col}C^{col}H^{col}$ operatively linked to at least one transcription control sequence. In all cases, the order of the genes is illustrative and can be any permutation thereof. Particularly preferred recombinant molecules include $pDIPE^{col}$, $pUCA^{col}E^{col}B^{col}F^{col}C^{col}D^{col}$, $pDIPA^{col}E^{col}B^{col}F^{col}C^{col}D^{col}$, $pDIPA^{col}E^{col}X^{sph}W^{sph}Y^{sph}B^{col}F^{col}C^{col}D^{col}$, $pDIPE^{col}X^{sph}W^{sph}F^{sph}D^{sph}A^{sph}Y^{sph}B^{sph}$, $pCKRH^{col}$, $pCKRH'^{col}$, $pDIPH^{col}A^{col}E^{col}B^{col}F^{col}C^{col}D^{col}$, and $pDIPH'^{col}A^{col}E^{col}B^{col}F^{col}C^{col}D^{col}$.

It is within the scope of the present invention that a cell can be transformed with a combination of recombinant molecules that together include all the genes necessary to improve biotin production. For example, a preferred combination of recombinant molecules are the nucleic acid sequences $E^{col}D^{sph}A^{sph}Y^{sph}B^{sph}$ and $X^{sph}W^{sph}F^{sph}$ each operatively linked to a bacteriophage T7, tac, and/or lac transcription control sequence. A second preferred combination of recombinant molecules are the nucleic acid sequences $D^{sph}A^{sph}Y^{sph}B^{sph}$ and $E^{col}X^{sph}W^{sph}F^{sph}$ each operatively linked to a bacteriophage T7, tac, and/or lac transcription control sequence.

According to one embodiment of the present invention, a recombinant cell is formed by transforming a host cell with an Escherichia coli bioE gene, or a functional equivalent thereof, alone or in combination with at least one nucleic acid sequence selected from Bacillus sphaericus genes bioA, bioB, bioD, bioF, bioW, bioX, and bioY genes, or a functional equivalent of any of these genes. According to another embodiment, a recombinant cell is formed by transforming a host cell with an Escherichia coli bioH gene, or a functional equivalent thereof, alone or in combination with at least one nucleic acid sequence selected from Escherichia coli bioA, bioB, bioC, bioD, bioE, and bioF genes, or a functional equivalent of any of these genes.

A host cell of the present invention can be either an untransformed cell or a cell that has been previously transformed with a nucleic acid sequence. Thus, the present invention can include transformation of the Escherichia coli bioE gene into strains of microorganisms previously transformed with at least one other nucleic acid sequence encoding an enzyme involved in biotin biosynthesis. Host cells of the present invention can either be indigenously (i.e., naturally) capable of biotin production or can be capable of producing biotin after being transformed with at least one nucleic acid sequence of the present invention.

A preferred host cell of the present invention is a cell in which the indigenous (i.e., intrinsic, natural) production of biotin is deregulated. As used herein, a cell's indigenous production of biotin refers to biotin production by the host cell prior to being transformed by nucleic acid sequences of the present invention. A cell's indigenous production of biotin can be deregulated in a variety of ways including, but not limited to, alleviating the controls a cell normally exerts on the synthesis of enzymes of the biotin biosynthetic pathway (e.g., repression), modifying enzymes of the biotin biosynthetic pathway to have higher specific activities (including reduction of feedback inhibition), and increasing the gene copy number of genes encoding enzymes of the biotin biosynthetic pathway (including by transformation). A cell that is no longer susceptible to repression by high biotin concentrations because, for example, the biotin repressor is no longer functional, is a particularly preferred host for recombinant molecules containing genes operatively linked to their indigenous transcription control sequences (i.e., to sequences that are subject to regulation by biotin).

Cells in which the synthesis and/or activity of particular enzymes of the biotin biosynthetic pathway are deregulated are particularly useful as host cells into which to introduce particular nucleic acid sequences. For example, a Bacillus sphaericus cell in which the enzymes encoded by the gene clusters bioXWF and bioDAYB are deregulated would be a preferred host to be transformed by a recombinant molecule containing an Escherichia coli bioE gene or functional equivalent thereof.

Preferred host cells of the present invention include, but are not limited to, bacteria and yeast. More preferred host cells include those of the genera Escherichia, Bacillus, Pseudomonas, Salmonella, Corynebacterium, and Saccharomyces. Preferred species of host cells include Escherichia coli, Bacillus sphaericus, and Bacillus subtilis, with Escherichia coli being more preferred.

A recombinant cell of the present invention is a host cell that is transformed with at least one nucleic acid of the present invention. Recombinant cells transformed with an Escherichia coli bioE gene or functional equivalent thereof, alone or in combination with at least one nucleic acid sequence selected from Bacillus sphaericus bioA, bioB, bioD, bioF, bioW, bioX, or bioY genes, or a functional equivalent of any of these genes, are capable of producing at least about 25 percent of their total biotin production as true biotin. Recombinant cells transformed with an *Escherichia coli* bioH gene or functional equivalent thereof alone or in combination with at least one nucleic acid sequence selected from *Escherichia coli* bioA, bioB, bioC, bioD, bioE, and bioF genes, or a functional equivalent of any of these genes, are capable of producing more biotin than a cell not transformed with an *Escherichia coli* bioH gene, or functional equivalent thereof.

Preferably, a recombinant cell is produced by transforming a host cell with one or more recombinant molecules containing one or more nucleic acid sequences of the present invention. As such, host cells can be transformed with single recombinant molecules containing any desired nucleic acid sequences to improve biotin production. Alternatively, host cells can be transformed with multiple recombinant molecules, each containing a subset of the desired combination of nucleic acid sequences such that in total, all desired nucleic acid sequences are transformed into the host cell.

Transformation can be accomplished using any process by which nucleic acid sequences are inserted into a cell. Transformation techniques include, but are not limited to, transfection, electroporation, microinjection, lipofection, adsorption, and protoplast fusion. A recombinant cell may remain unicellular or may grow into a tissue or a multicellular organism. Transformed nucleic acid sequences of the present invention can remain extrachromosomal or can integrate into one or more sites within a chromosome of a host cell in such a manner that their ability to be expressed is retained. Integrated nucleic acid sequences often are more stable than extrachromosomal sequences. As such, it is within the scope of the present invention that expression of nucleic acid sequences encoding enzymes involved in biotin biosynthesis may be due to expression of plasmid sequences or to sequences integrated into the host genome.

Preferred recombinant cells of the present invention include cells transformed with nucleic acid sequence combinations E, EB, EBD, EBDA, EBDAF, EBDAFWXY, H, BH, EH, BEH, BEDH, BEDAH, BEDAFH, and BEDAFCH. Preferably such nucleic acid sequence combinations are operatively linked to at least one transcription control sequence, and preferably to at least one bacteriophage T7, tac and/or lac transcription control sequence. Particularly preferred recombinant cells include cells transformed with one or more nucleic acid sequence combinations described in Table 1. Such sequences are preferably operatively linked to a yeast or bacterial transcription control sequence, and more preferably to at least one bacteriophage T7, tac and/or lac transcription control sequence when expressed in *Escherichia coli* cells, and to a bacteriophage SP01 transcription control sequence when expressed in Bacillus cells. Preferred recombinant cells are transformed with combinations of recombinant molecules that contain the nucleic acid sequences $E^{col}$, $E^{col}B^{sph}$, $E^{col}B^{sph}D^{sph}$, $E^{col}B^{sph}D^{sph}A^{sph}$, $E^{col}B^{sph}D^{sph}A^{sph}F^{sph}$, $E^{col}B^{sph}D^{sph}A^{sph}F^{sph}W^{sph}X^{sph}Y^{sph}$, $E^{col}B^{col}D^{col}A^{col}F^{col}W^{sph}X^{sph}Y^{sph}$, $H^{col}$, or $E^{col}B^{col}D^{col}A^{col}F^{col}C^{col}H^{col}$ operatively linked to a bacteriophage T7, tac, or lac transcription control sequence, and preferably to a T7 transcription control sequence. Preferred recombinant molecules contain the nucleic acid sequences $E^{col}B^{sph}D^{sph}A^{sph}F^{sph}W^{sph}X^{sph}Y^{sph}$, $E^{col}B^{col}D^{col}A^{col}F^{col}W^{sph}X^{sph}Y^{sph}$, or $E^{col}B^{col}D^{col}A^{col}F^{col}C^{col}H^{col}$ operatively linked to at least one transcription control sequence. In all cases, the order of the genes is illustrative and can be any permutation thereof. Particularly preferred recombinant molecules include pDIPE$^{col}$, pUCA$^{col}E^{col}B^{col}F^{col}C^{col}D^{col}$, pDIPA$^{col}E^{col}B^{col}F^{col}C^{col}D^{col}$, pDIPA$^{col}E^{col}X^{sph}W^{sph}Y^{sph}B^{col}F^{col}C^{col}D^{col}$, pDIPE$^{col}X^{sph}W^{sph}F^{sph}D^{sph}A^{sph}Y^{sph}B^{sph}$, pCKRH$^{col}$, pCKRH$^{1col}$, pDIPH$^{col}A^{col}E^{col}B^{col}F^{col}C^{col}D^{col}$, and pDIPH$^{1col}A^{col}E^{col}B^{col}F^{col}C^{col}D^{col}$. Recombinant cells that are particularly preferred include *Escherichia coli* BL21/DE3-pDIPA$^{col}E^{col}X^{sph}W^{sph}Y^{sph}B^{col}F^{col}C^{col}D^{col}$, *Escherichia coli* BL21/DE3-pDIPE$^{col}X^{sph}W^{sph}F^{sph}D^{sph}A^{sph}Y^{sph}B^{sph}$, *Escherichia coli* BL21/DE3-pCKRH$^{col}$+pDIPA$^{col}E^{col}B^{col}F^{col}C^{col}D^{col}$, *Escherichia coli* BL21/DE3-pCKRH$^{1col}$+pDIPA$^{col}E^{col}B^{col}F^{col}C^{col}D^{col}$, *Escherichia coli* BL21/DE3-pDIPH$^{col}A^{col}E^{col}B^{col}F^{col}C^{col}D^{col}$, and *Escherichia coli* BL21/DE3-pDIPH$^{1col}A^{col}E^{col}B^{col}F^{col}C^{col}D^{col}$.

Another embodiment of the present invention is a recombinant cell that is produced by transforming a host other than *Escherichia coli* with a recombinant molecule comprising an *Escherichia coli* bioE gene. Such a recombinant cell can also include one or more additional genes involved in biotin biosynthesis such as *Escherichia coli* bioA, bioB, bioC, bioD, bioF, and bioH genes, and/or *Bacillus sphaericus* bioA, bioB, bioD, bioF, bioW, bioX, and bioY genes, or functional equivalents of any of those genes. Preferred recombinant cells are bacterial and yeast cells. More preferred recombinant cells are of the genus Bacillus, preferably of the species *Bacillus sphaericus*.

It may be appreciated by one skilled in the art that use of recombinant DNA technologies can improve expression of transformed nucleic acid sequences by manipulating, for example, the number of copies of the nucleic acid sequences within a host cell, the efficiency with which those nucleic acid sequences are transcribed, the efficiency with which the resultant transcripts are translated, and the efficiency of post-translational modifications. Recombinant techniques useful for increasing the expression of nucleic acid sequences encoding enzymes involved in biotin synthesis include, but are not limited to, operatively linking nucleic acid sequences to high-copy number plasmids, integration of the nucleic acid sequences into one or more host cell chromosomes, addition of vector stability sequences to plasmids, substitutions or modifications of transcription control signals (e.g., promoters, operators, enhancers), substitutions or modifications of translational control signals (e.g., ribosome binding sites, shine-Delgarno sequences), modification of the nucleic acid sequences encoding enzymes involved in biotin biosynthesis to correspond to the codon usage of the host cell, deletion of sequences that destabilize transcripts, and use of control signals that temporally separate recombinant cell growth from recombinant enzyme production during fermentation. The activity of an expressed recombinant enzyme of the present invention may be improved by fragmenting, modifying, or derivatizing nucleic acid sequences encoding enzymes involved in biotin biosynthesis.

According to the present invention, a recombinant cell transformed with an *Escherichia coli* bioE gene, or a functional equivalent thereof, either alone or in combination with at least one additional nucleic acid sequence selected from the group consisting of *Bacillus sphaericus* bioA, bioB, bioD, bioF, bioX, bioW, and bioY genes, or functional equivalents of any of these genes, is particularly useful in that such a cell is capable of efficiently converting biotin vitamers to true biotin when cultured in an effective medium, such that at least about 25 percent of the biotin produced by the cell is true biotin. The present invention includes all recombinant cells produced as described above that are capable of producing a percentage amount of true biotin in excess of that produced by cells transformed with *Bacillus sphaericus* biotin gene clusters that have been described in the literature. In preferred recombinant cells, at least about 50 percent, more preferably at least about 75 percent, and even more preferably at least about 90 percent of the biotin produced is true biotin. It is within the scope of the present invention that a recombinant cell of the present invention can produce essentially about 100 percent true biotin (i.e., that substantially all of the total biotin produced is true biotin).

It should be noted that the ability of recombinant cells of the present invention to efficiently convert biotin vitamers to true biotin does not depend on the total amount of biotin produced. That is, regardless of the amount of biotin a recombinant cell can inherently produce, the present invention teaches a method of biotin production such that at least about 25 percent, preferably at least about 50 percent, more preferably at least about 75 percent, even more preferably at least about 90%, and even more preferably essentially about 100 percent of the biotin produced by the cell comprises true biotin.

Another embodiment of the present invention is the use of a cell transformed with an *Escherichia coli* bioH gene or functional equivalent thereof alone or in combination with at least one nucleic acid sequence selected from *Escherichia coli* bioA, bioB, bioC, bioD, bioE, and bioF genes, or a functional equivalent of any of these genes, to produce biotin. When cultured in an effective medium, such recombinant cells are capable of producing more biotin than a cell not transformed with an *Escherichia coli* bioH gene, or functional equivalent thereof. As used herein, "more biotin" is any measurable difference of biotin production between the two strains. Preferably, recombinant cells transformed with an *Escherichia coli* bioH gene, or functional equivalent thereof, produce at least about 50 percent more, more preferably at least about 2 times more, and even more preferably at least about 4 times more biotin than a cell not transformed with an *Escherichia coli* bioH gene, or functional equivalent thereof.

As used herein, an "effective medium" refers to any medium in which a recombinant cell, when cultured, is capable of producing biotin in desired amounts. An effective medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium. Recombinant cells of the present invention can be cultured in conventional fermentation bioreactors, which include, but are not limited to, batch, fed-batch, cell recycle, and continuous fermentors. Culturing is carried out at a temperature, pH and oxygen content appropriate for the recombinant cell. Such culturing conditions are well within the expertise of one of ordinary skill in the art.

In a preferred embodiment, the effective medium is supplemented with an effective amount of a compound that promotes biotin production. Such compounds include biotin precursors or derivatives thereof that, when fed to the cells, enable the cells to produce increased amounts of biotin. An effective amount of such a compound is an amount such that the particular step of the biotin synthetic pathway being supplemented is no longer rate limiting. Biotin precursors that can be added to the media include, but are not limited to, at least one dicarboxylic acid or derivative thereof, at least one biotin vitamer or derivative thereof, and mixtures thereof. Preferred dicarboxylic acids include pimelic acid, azelaic acid, and derivatives of either, with pimelic acids and derivatives thereof being more preferred. As used herein, "derivatives thereof" are compounds with similar functional characteristics to the compounds. For example, pimelyl-CoA is considered to be a derivative of pimelic acid. Pelargonic acids and their derivatives are preferred biotin vitamer supplements. Preferred pelargonic acid supplements include 7-keto-8-aminopelargonic acid, 7,8-diaminopelargonic acid, and derivatives of either.

According to one aspect of the present invention, recombinant cells are cultured in an effective medium supplemented by a biotin precursor to increase the amount of biotin produced by a cell. Preferably, the nature of the biotin precursor used is dependent upon the genetic make-up of the recombinant cell. In a preferred embodiment, a desirable biotin precursor supplement is a compound that is produced by a reaction in the biotin biosynthetic pathway that is essentially immediately upstream of (i.e., just prior to) the reactions carried out by enzymes encoded by the genes transformed into the recombinant cell being cultured. For example, a recombinant cell transformed with an *Escherichia coli* bioE gene or a functional equivalent thereof, and with *Bacillus sphaericus* bioB, bioD, bioA, bioF, and bioW (with or without bioX and bioY) genes, or functional equivalents thereof, (e.g., a recombinant cell transformed with the nucleic acid sequence combination $E^{col}B^{sph}D^{sph}A^{sph}F^{sph}W^{sph}X^{sph}Y^{sph}$ or $E^{col}B^{col}D^{col}A^{col}F^{col}W^{sph}X^{sph}Y^{sph}$) is cultured in an effective medium supplemented with a dicarboxylic acid, such as pimelic acid or azelaic acid, or a derivative thereof. One or more biotin vitamers can also be added to the medium. However, for such recombinant cells, a preferred supplement is pimelic acid or a derivative thereof since the enzymes encoded by the genes transformed into the cells should be capable of converting essentially all of the pimelic acid to true biotin rather than to biotin vitamers.

In an analogous fashion, the effective medium of a recombinant cell transformed with the *Escherichia coli* bioE gene, or a functional equivalent thereof, and with *Bacillus sphaericus* bioA, bioB, and bioD genes, or functional equivalents thereof, is preferably supplemented with 7-keto-8-aminopelargonic acid. Similarly, the effective medium of a recombinant cell transformed with the *Escherichia coli* bioE gene, or a functional equivalent thereof, and with *Bacillus sphaericus* bioB and bioD genes, or functional equivalents thereof, is peferably supplemented with 7,8-diaminopelargonic acid.

In a preferred embodiment of the present invention using a recombinant cell transformed by an *Escherichia coli* bioE gene to enhance conversion of biotin vitamers to true biotin, biotin is produced by a method including: (a) operatively linking a first nucleic acid sequence containing *Escherichia coli* bioA, bioE, bioB, bioF, bioC, and bioD genes to a transcription control sequence functional in *Escherichia coli* to form a first recombinant molecule denoted pAEBFCD in which expression of all six genes is under the control of the transcription control sequence; (b) ligating a second nucleic acid sequence containing *Bacillus sphaericus* bioX, bioW, and bioY genes into the first recombinant molecule between the *Escherichia coli* bioE and *Escherichia coli* bioB genes to form a second recombinant molecule denoted pAEXW-YBFCD in which expression of all nine genes is under the control of the transcription control sequence; (c) transforming the second recombinant molecule into an *Escherichia coli* host cell to form a recombinant cell; (d) culturing the recombinant cell in an effective medium supplemented with pimelic acid or a derivative thereof in order to produce biotin such that at least about 25 percent of the biotin produced is true biotin; and (e) recovering biotin therefrom. Preferably at least about 50 percent, more preferably at least about 75 percent, and even more preferably at least about 90 percent of the total biotin produced is true biotin. Preferred transcription control sequences include those of bacteriophage T7 and/or tac.

In another preferred embodiment of the present invention using a recombinant cell transformed with an *Escherichia coli* bioE gene, biotin is produced by a method including: (a) ligating a first nucleic acid sequence containing the *Escherichia coli* bioE gene to a second nucleic acid sequence containing the *Bacillus sphaericus* gene cluster bioDAYB to form a third nucleic acid sequence; (b) operatively linking the third nucleic acid sequence to a first transcription control sequence functional in *Escherichia coli* to form a first recombinant molecule denoted pbioEDAYB in which expression of all five genes is under the control of the first transcription control sequence; (c) operatively linking a fourth nucleic acid sequence containing the *Bacillus sphaericus* gene cluster bioXWF to a second *Escherichia coli* transcription control sequence functional in *Escherichia coli* to form a second recombinant molecule denoted pbioXWF in which expression of the three genes is under the control of the second transcription control sequence; (d) forming a third recombinant molecule by combining pbioEDAYB and pbioXWF in such a way that expression of *Escherichia coli* bioE and the *Bacillus sphaericus* bioDAYB gene cluster is under the control of the first transcription control sequence and expression of the *Bacillus sphaericus* bioXWF gene cluster is under the control of the second transcription control sequence; (e) transforming the third recombinant molecule into an *Escherichia coli* host cell to form a recombinant cell; (f) culturing the recombinant cell in an effective medium supplemented with pimelic acid or a derivative thereof in order to produce biotin such that at least about 25 percent of the biotin produced is true biotin; and (g) recovering biotin therefrom. Preferably at least about 50 percent, more preferably at least about 75 percent, and even more preferably at least about 90 percent of the total biotin produced is true biotin. Preferred transcription control sequences include those of bacteriophage T7 and/or tac. Note that the first and second transcription control sequences can comprise identical transcription control sequences; for example, both transcription control sequences can be bacteriophage T7 transcription control sequences. In an alternative embodiment of this biotin production process, the second nucleic acid sequence contains the *Bacillus sphaericus* bioXWF gene cluster and the third nucleic acid sequence contains the *Bacillus sphaericus* bioDAYB gene cluster, thereby leading to co-expression of *Escherichia coli* bioE and the *Bacillus sphaericus* bioXWF gene cluster under the control of the first transcription control sequence and expression of the *Bacillus sphaericus* bioDAYB gene cluster under the control of the second transcription control sequence.

In a preferred embodiment of the present invention using a recombinant cell transformed with an *Escherichia coli* bioH gene to enhance biotin production, biotin is produced by a method including: (a) operatively linking a first nucleic acid sequence containing *Escherichia coli* bioA, bioE, bioB, bioF, bioC, and bioD genes to a transcription control sequence functional in *Escherichia coli* to form a first recombinant molecule denoted pAEBFCD in which expression of all six genes is under the control of the transcription control sequence; (b) ligating a second nucleic acid sequence containing an *Escherichia coli* bioH gene to the first recombinant molecule between the transcription control sequence and the *Escherichia coli* bioA gene to form a second recombinant molecule denoted pHAEBFCD in which expression of all seven genes is under the control of the transcription control sequence; (c) transforming an *Escherichia coli* cell with the second recombinant molecule to obtain a recombinant cell; (d) culturing the recombinant cell in an effective medium to produce biotin such that the recombinant cell produces more biotin than does a recombinant cell not transformed with the *Escherichia coli* bioH gene; and (e) recovering biotin therefrom. Preferred transcription control sequences include those of bacteriophage T7.

In another preferred embodiment of the present invention using a recombinant cell transformed with an *Escherichia coli* bioH gene, biotin is produced by a method including (a) operatively linking a first nucleic acid sequence containing an *Escherichia coli* bioH gene to a first transcription control sequence functional in *Escherichia coli* to form a first recombinant molecule denoted pH; (b) operatively linking a second nucleic acid sequence containing *Escherichia coli* bioA, bioE, bioB, bioF, bioC, and bioD genes to a second transcription control sequence functional in *Escherichia coli* to form a second recombinant molecule denoted pAEBFCD in which expression of all six genes is under the control of the transcription control sequence; (c) co-transforming an *Escherichia coli* cell with the first and second recombinant molecules to obtain a recombinant cell; (d) culturing the recombinant cell in an effective medium to produce biotin such that the recombinant cell produces more biotin than does a recombinant cell not transformed with the first recombinant molecule; and (e) recovering biotin therefrom. Preferred transcription control sequences include those of bacteriophage T7 and/or tac. Note that the first and second transcription control sequences can be identical as long as together they do not direct a level of expression that would deleteriously affect the cell.

As used herein, the term "recovering biotin" simply refers to collecting the whole fermentation medium comprising biotin and need not imply additional steps of separation or purification. Biotin can be further separated and/or purified from the fermentation medium using a variety of techniques known in the art. A simplified biotin purification method which results in high yields of essentially pure biotin is described in co-pending U.S. patent application Ser. No. 07/822,449, by Cheung, filed Jan. 17, 1992. Briefly, following fermentation, cells are separated from the biotin-containing supernatant by centrifugation of filtration. The supernatant is passed over an ion-exchange column from which the biotin is eluted using formic acid. This step effectively separates true biotin from biotin vitamers. Eluted fractions containing true biotin are acidified in order to precipitate the biotin, preferably by adjusting the pH of the eluent to a pH of from about pH 1 to about pH 4. The precipitated true biotin is subsequently dissolved and submitted to at least one step of crystallization.

The following examples are provided for the purposes of illustration and are not intended to limit the scope of the invention.

EXAMPLES

In the following examples, all recombinant molecules were analyzed by restriction digests to confirm that the correct nucleic acid sequences were inserted in the proper orientation for transcription.

Example 1

Production of nucleic acid sequences and recombinant molecules containing coding regions of genes involved in the *Escherichia coli* biotin biosynthetic pathway A. pCB107

This example describes the production of a plasmid containing the Escherichia coli biotin operon including the bioE, bioA, bioB, bioF, bioC, and bioD genes.

Figure 2:
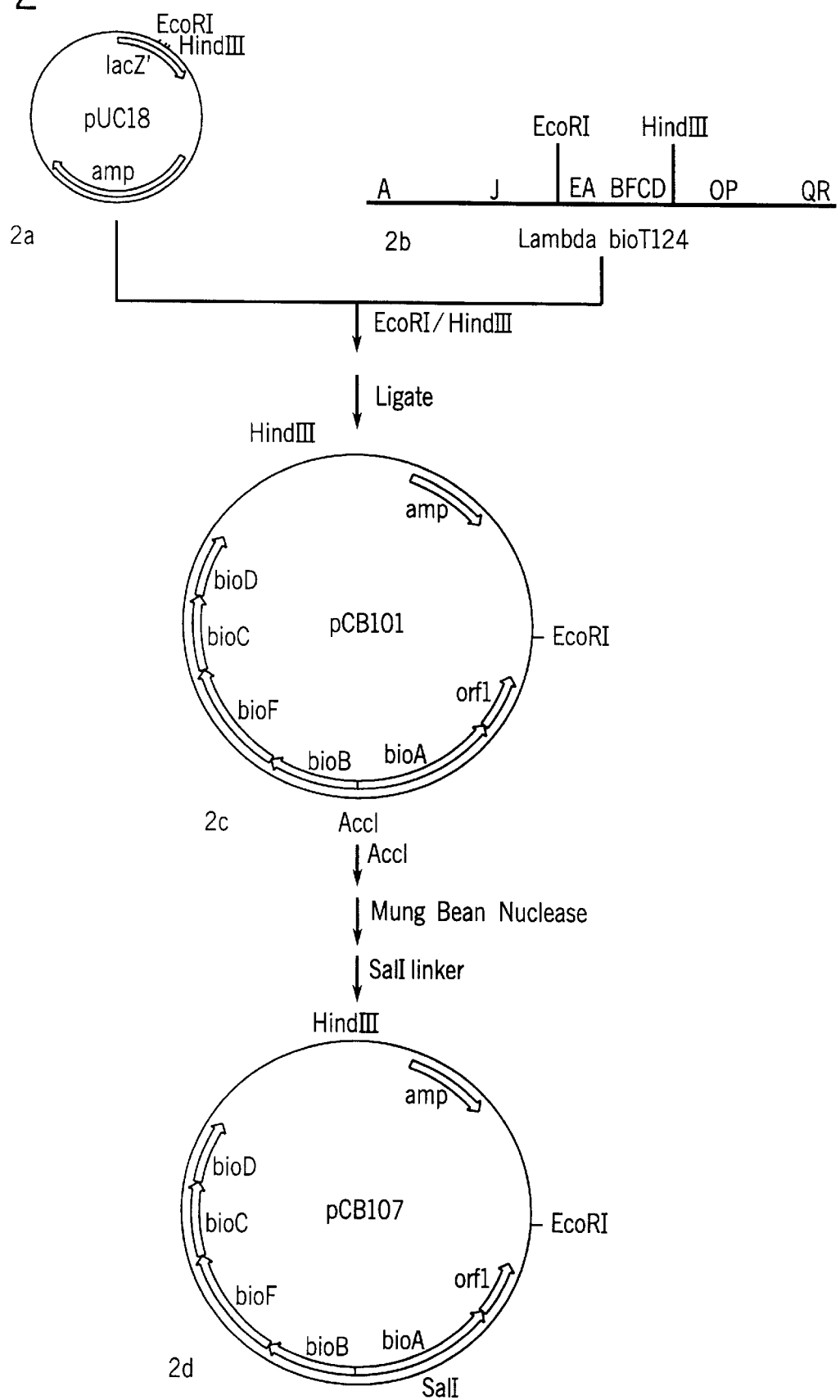
FIG. 2 contains a schematic drawing of the process of constructing plasmids containing genes of the *Escherichia coli* biotin operon.

Referring to FIG. 2b, lambda bio-transducing phage bioT124 (Guha et al., pp.53–62, 1971, *J. Mol. Bol.*, Vol. 56) was digested with restriction enzymes EcoRI and HindIII to produce a 6 kilobase (kb) fragment, denoted EABFCD, which contains the Escherichia coli bioE, bioA, bioB, bioF, bioC, and bioD genes. Using standard protocols (see Sambrook et al., ibid.), DNA fragment EABFCD was ligated into the pUC18 plasmid (available from GIBCO BRL, Gaithersburg, Md., and shown in FIG. 2a) that had been digested with EcoRI and HindIII. The resulting plasmid, depicted in FIG. 2c, is referred to as PCB101.

To convert the AccI site in the operator region of the Escherichia coli biotin operon to a SalI site, pCB101 was digested with AccI, followed by Mung Bean Nuclease. SalI linkers were ligated to the digested plasmid, and the plasmid self-ligated, using standard techniques. The resulting plasmid, denoted pCB107 and shown in FIG. 2d, contains the Escherichia coli bioE, bioA, bioB, bioF, bioC, and bioD genes with a SalI site located between the bioA and bioB coding regions. The restriction site conversion resulted in the insertion of 8 base pairs (bp) into the operator site of the biotin operon.

B. pDIPB$^{col}$F$^{col}$C$^{col}$D$^{col}$

This example describes the production of a recombinant molecule containing the Escherichia coli bioB, bioF, bioC, and bioD genes, operatively linked to a bacteriophage T7 transcription control sequence.

Figure 3:
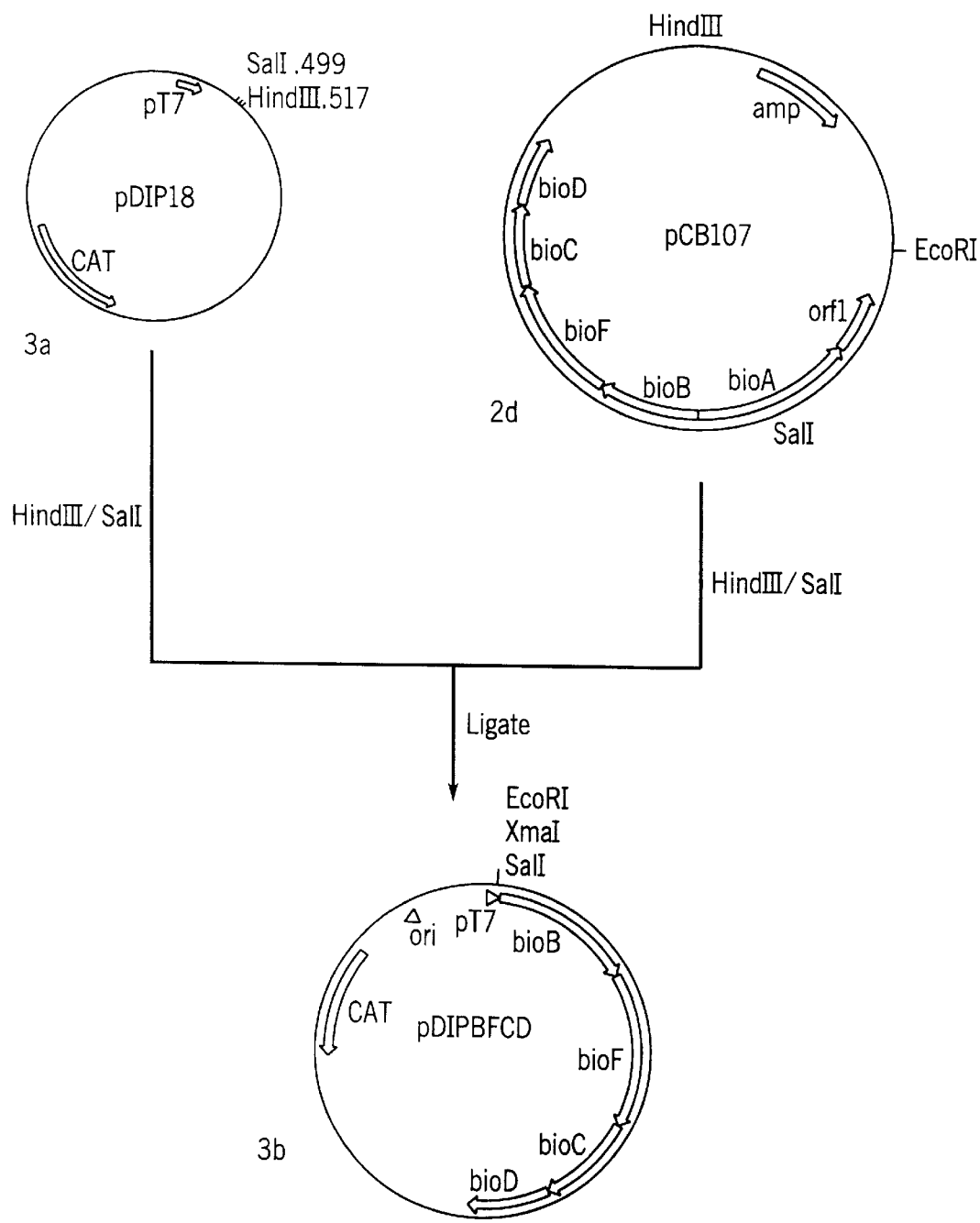
FIGS. 3 through 9 contain schematic drawings of methods to produce certain nucleic acid sequences and recombinant molecules containing *Escherichia coli* genes encoding enzymes involved in biotin production.

Referring to FIG. 3, a 3.8 kb DNA fragment containing the coding regions, but lacking the indigenous (i.e., biotin) transcription control sequences, of the Escherichia coli bioB, bioF, bioC, and bioD genes and denoted B$^{col}$F$^{col}$C$^{col}$D$^{col}$, was produced by digesting pCB107 (produced as described in Example 1A and shown in FIG. 2d) with HindIII and SalI. The DNA fragment was ligated into the expression vector pDIP18 (obtained from Dr. L. Gold, University of Colorado, Boulder, Colo. and shown in FIG. 3a), that had been restricted with HindIII and SalI, in such a manner as to operatively link B$^{col}$F$^{col}$C$^{col}$D$^{col}$ to the bacteriophage T7 transcription control sequence.

The resulting recombinant molecule, pDIPB$^{col}$F$^{col}$C$^{col}$D$^{col}$, also referred to as pDIPBFCD, is shown in FIG. 3b.

C. pDIPA$^{col}$E$^{col}$

This example describes the production of a recombinant molecule containing the Escherichia coli bioA and bioE genes operatively linked to a bacteriophage T7 transcription control sequence.

Figure 4:
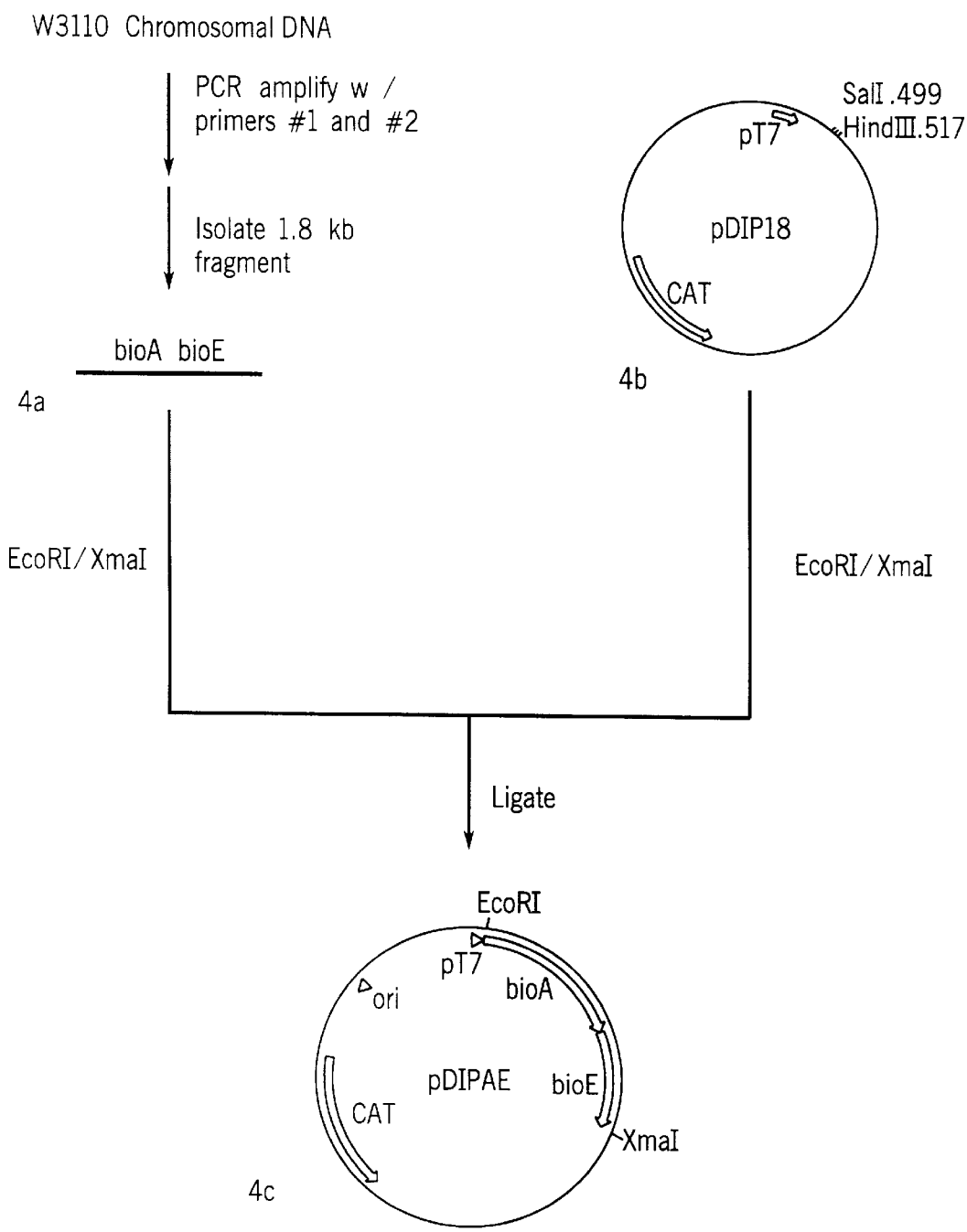

A 1.8 kb fragment containing the coding regions, but lacking the indigenous transcription control sequences, of the Escherichia coli bioA and bioE genes and denoted A$^{col}$E$^{col}$ or bioAbioE, was produced by polymerase chain reaction (PCR) amplification of a portion of W3110 Escherichia coli genomic DNA (Escherichia coli W3110 is available from the Escherichia coli Genetic Stock Center, New Haven, Conn.) using primers #1 and #2 (SEQ ID NO:1 and SEQ ID NO:2, respectively) (see FIG. 4a). Primers #1 and #2 (SEQ ID NO:1 and SEQ ID NO:2, respectively) contain the restriction sites EcoRI and XmaI, respectively, and are shown below.

```
Primer #1 (SEQ ID NO:1)
5' AATCTTTTGA ATTCGGTTTA GGAGTCGATT ATG AC 3'
            EcoRI                    Translation
                                     Initiation
                                     site Primer #2 (SEQ ID NO:2)
5' GCGCCACCCG GGAGAGTGA TTA AC 3'
         XmaI           Translation
                        Stop site
```

Primer #1 (SEQ ID NO:1) is complementary to (i.e., can hybridize with) a nucleic acid sequence immediately upstream from and containing the translation initiation site of the Escherichia coli bioA gene. The 5' end of primer #1 (SEQ ID NO:1) is about 5 bp downstream from (i.e., 3' of) the transcription initiation site of the Escherichia coli bioA gene. As such, resulting PCR fragment A$^{col}$E$^{col}$ does not include an indigenous transcription control sequences and, therefore, can be operatively linked to a transcription control sequence not normally associated with the Escherichia coli bioA gene. Primer #2 (SEQ ID NO:2) is complementary to a nucleic acid sequence including and immediately downstream from the stop codon (UAA) of the Escherichia coli bioE gene.

Following amplification, PCR fragment A$^{col}$E$^{col}$ was digested with EcoRI and XmaI and ligated to expression vector pDIP18 (see FIG. 4b) that had been restricted with EcoRI and XmaI. As such, the Escherichia coli bioA and bioE genes were operatively linked to the bacteriophage T7 transcription control sequence to form recombinant molecule pDIPA$^{col}$E$^{col}$, also referred to as pDIPAE (see FIG. 4c).

D. pDIPA$^{col}$E$^{col}$B$^{col}$F$^{col}$C$^{col}$D$^{col}$

This example describes the production of a recombinant molecule containing the entire biotin operon including the Escherichia coli bioA, bioE, bioB, bioF, bioC, and bioD genes, operatively linked to a bacteriophage T7 transcription control sequence.

Figure 5:
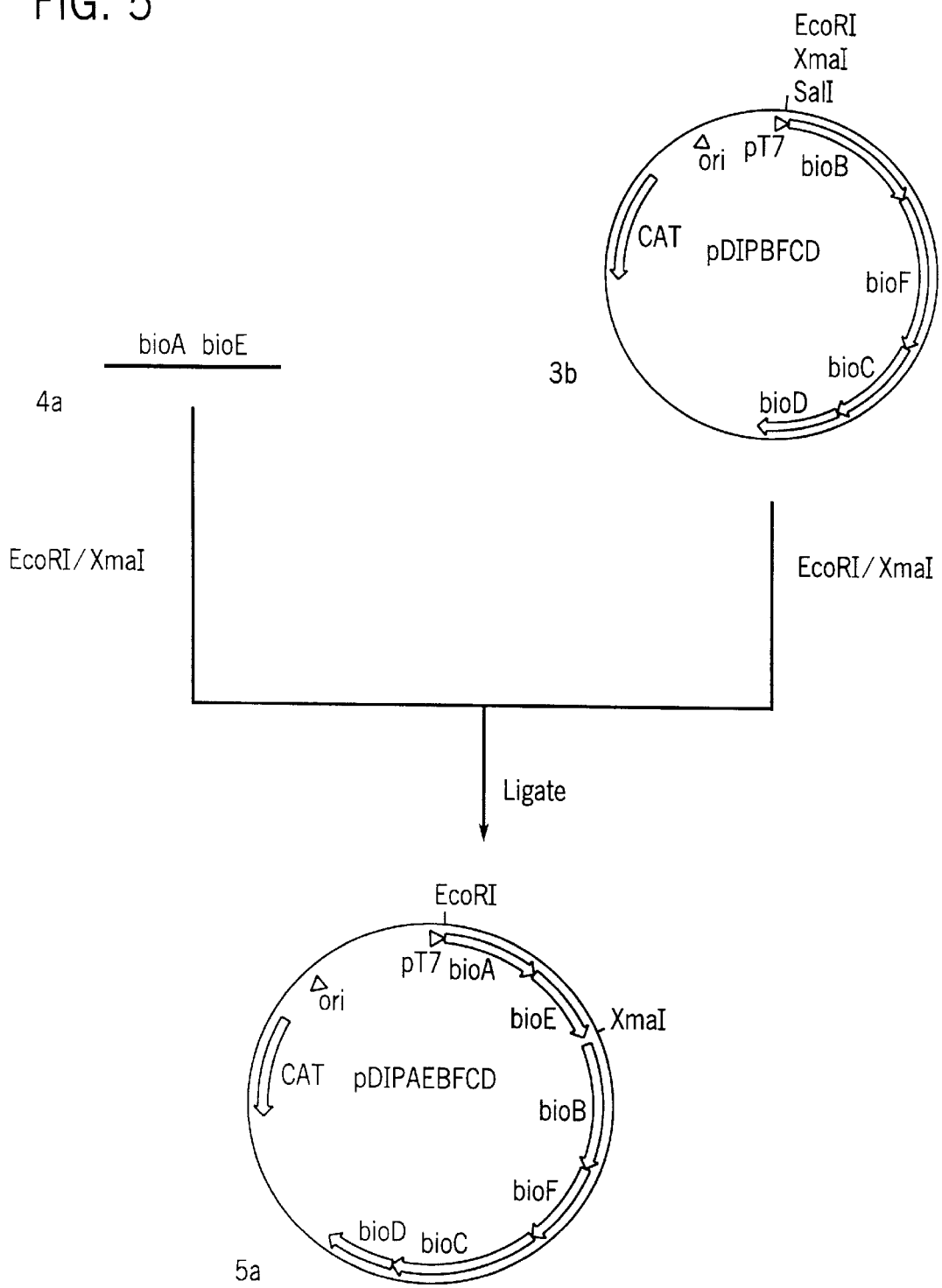

PCR fragment A$^{col}$E$^{col}$, produced as described in Example 1C and depicted in FIG. 4a as bioAbioE, was digested with EcoRI and XmaI and ligated, as shown in FIG. 5, to the recombinant molecule pDIPB$^{col}$F$^{col}$C$^{col}$D$^{col}$ (produced as described in Example 1B and depicted in FIG. 3b) that had been restricted with XmaI and EcoRI. As such, the Escherichia coli bioA and bioE genes, in addition to the bioB, bioF, bioC, and bioD genes, were operatively linked to the bacteriophage T7 transcription control sequence to form recombinant molecule pDIPA$^{col}$E$^{col}$B$^{col}$F$^{col}$C$^{col}$D$^{col}$, also referred to as pDIPAEBFCD (see FIG. 5a).

E. pDIPA$^{col}$B$^{col}$F$^{col}$C$^{col}$D$^{col}$

This example describes the production of a recombinant molecule containing the entire Escherichia coli biotin operon, except for the Escherichia coli bioE gene, (i.e., containing Escherichia coli bioA, bioB, bioF, bioC, and bioD genes) operatively linked to a bacteriophage T7 transcription control sequence.

A 1.2 kb fragment containing the coding region, but lacking the indigenous transcription control sequence, of the Escherichia coli bioA gene and denoted A$^{col}$ or bioA, was produced by PCR amplification of a portion of W3110 Escherichia coli genomic DNA using primers #1 and #3 SEQ ID NO:1 and SEQ ID NO:3, respectively). See FIG. 6a. Primer #3 (SEQ ID NO:3) contains the restriction site KpnI and is shown below.

```
Primer #3 (SEQ ID NO:3)
5' GTGTGTGGTA CC TTA TTG GCA AAA AAA 3'
        KpnI   Translation
               Stop site
```

Figure 6:
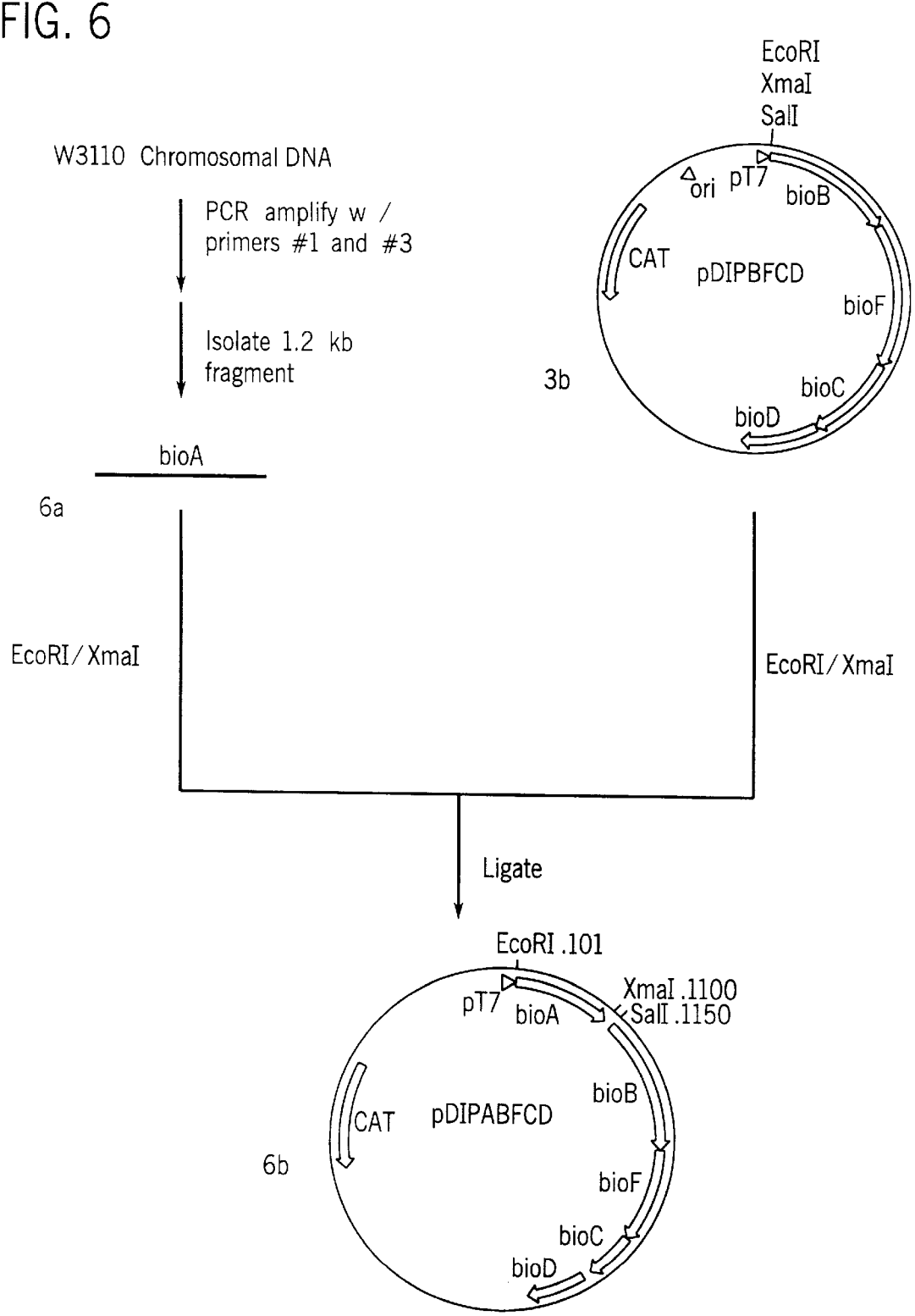

Primer #3 (SEQ ID NO:3) is complementary to a nucleic acid sequence including and immediately downstream from the stop codon (UAA) of the *Escherichia coli* bioA gene. Following amplification, PCR fragment $A^{col}$ was digested with EcoRI and KpnI and ligated, as shown in FIG. 6, to the recombinant molecule pDIPB$^{col}$F$^{col}$C$^{col}$D$^{col}$ (produced as described in Example 1B and depicted in FIG. 3b) that had been restricted with EcoRI and KpnI. As such, the *Escherichia coli* bioA gene, in addition to the bioB, bioF, bioC, and bioD genes, was operatively linked to the bacteriophage T7 transcription control sequence to form recombinant molecule pDIPA$^{col}$B$^{col}$F$^{col}$C$^{col}$D$^{col}$, also referred to as pDIPABFCD (see FIG. 6b).

F. pUCA$^{col}$E$^{col}$B$^{col}$F$^{col}$C$^{col}$D$^{col}$

This example describes production of a recombinant molecule in which the entire *Escherichia coli* biotin operon (i.e., *Escherichia coli* bioA, bioE, bioB, bioF, bioC, and bioD genes) are operatively linked to a lac transcription control sequence.

A 6 kb fragment containing the T7 promoter operatively linked to the *Escherichia coli* bioA, bioE, bioB, bioF, bioC, and bioD genes was produced by PCR amplification from purified pDIPA$^{col}$E$^{col}$B$^{col}$F$^{col}$C$^{col}$D$^{col}$ DNA (produced as described in Example 1D and depicted in FIG. 5a as pDIPAEBFCD), using primers #4 and #5 (SEQ ID NO:4 and SEQ ID NO:5, respectively). See FIG. 7a. The primer sequences are shown below.

```
Primer #4 (SEQ ID NO:4)
5'TAATACGACT CACTATAGGG AGA 3'

Primer #5 (SEQ ID NO:5)
5'CATGATGAAT TCAAGGCAAG GT TTA TGT AC
        EcoRI              Translation
                           Stop site
```

Primer #4 (SEQ ID NO:4) is complementary to the nucleic acid sequence of the T7 promoter which is about 22 bp 5' of the EcoRI site of pDIPA$^{col}$E$^{col}$B$^{col}$F$^{col}$C$^{col}$D$^{col}$. Primer #5 (SEQ ID NO:5) is complementary to the nucleic acid sequence including and immediately downstream of the stop codon (UAA) of the *Escherichia coli* bioD gene.

Figure 7:
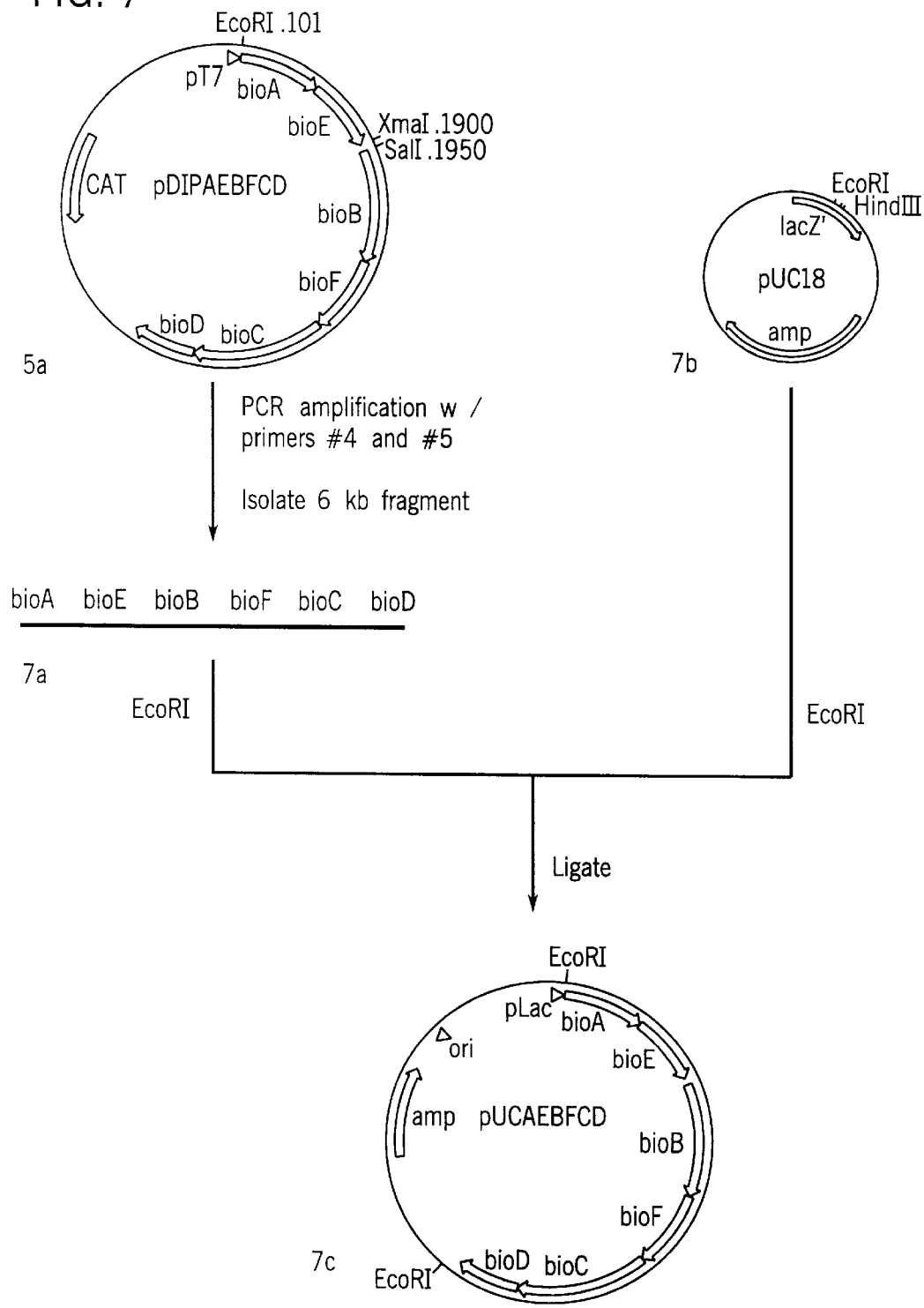

Following PCR amplification, the 6 kb PCR fragment was digested with EcoRI and ligated to pUC18 (see FIG. 7b) that had been restricted with EcoRI. This results in removal of the T7 promoter sequences as indicated in FIG. 7. This recombinant molecule is pUCA$^{col}$E$^{col}$B$^{col}$F$^{col}$C$^{col}$D$^{col}$, also referred to as pUCAEBFCD (see FIG. 7c).

G. pUCA$^{col}$B$^{col}$F$^{col}$C$^{col}$D$^{col}$

This example describes production of a recombinant molecule containing the entire *Escherichia coli* biotin operon except for the *Escherichia coli* bioE gene (i.e., containing *Escherichia coli* bioA, bioB, bioF, bioC, and bioD genes) operatively linked to a lac transcription control sequence.

A 5 kb fragment containing the T7 promoter operatively linked to the *Escherichia coli* bioA, bioB, bioF, bioC, and bioD genes was produced by PCR amplification from purified pDIPA$^{col}$B$^{col}$F$^{col}$C$^{col}$D$^{col}$ DNA (produced as described in Example 1E and depicted in FIG. 6b), using primers #4 and #5 (SEQ ID NO:4 and SEQ ID NO:5, respectively) of Example 1F. See FIG. 8a.

Figure 8:
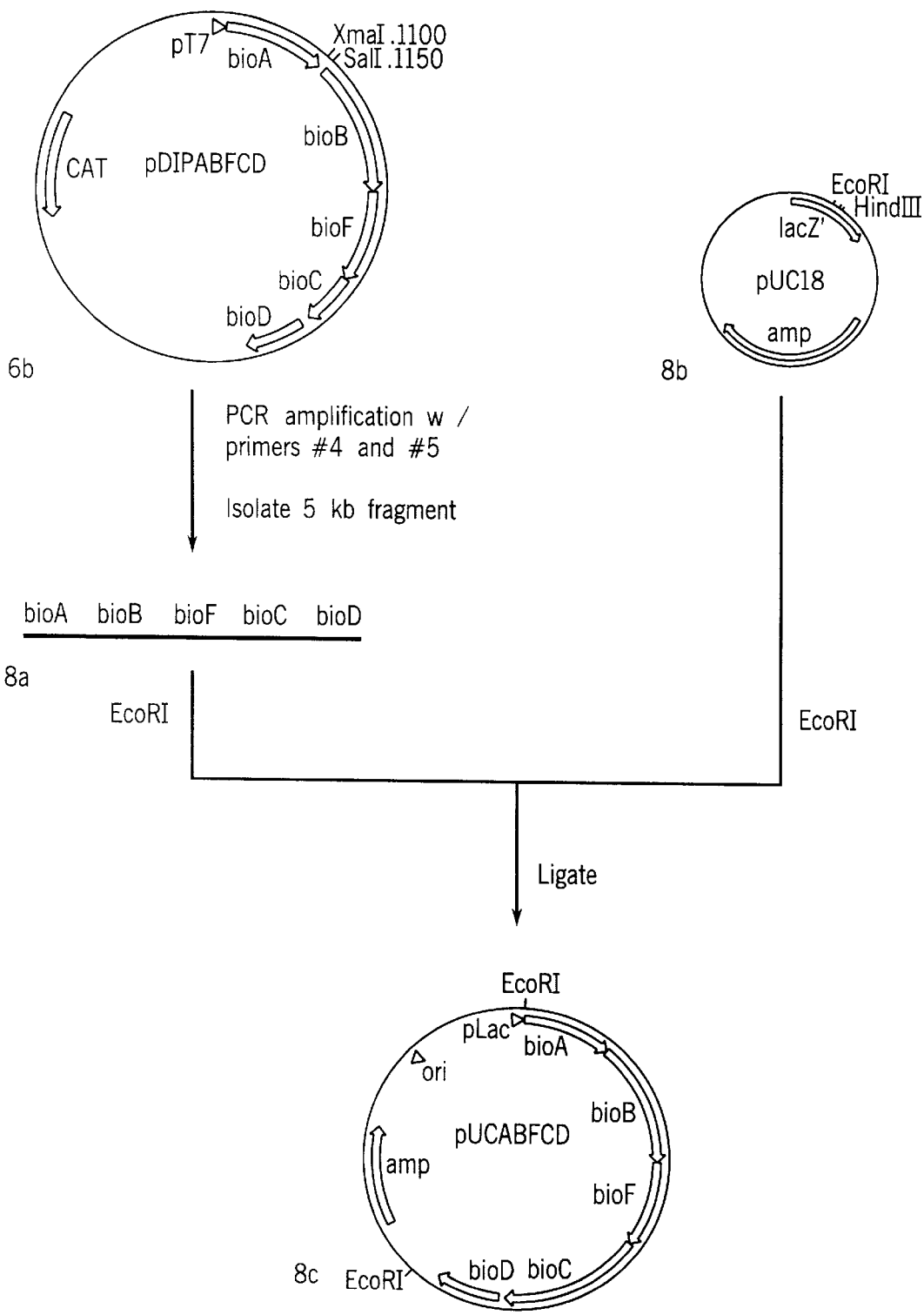

Following PCR amplification, the 5 kb PCR fragment was digested with EcoRI and ligated to pUC18 (see FIG. 8b) that had been restricted with EcoRI. This results in removal of the T7 promoter sequences as indicated in FIG. 8. This recombinant molecule is pUCA$^{col}$B$^{col}$F$^{col}$C$^{col}$D$^{col}$, also referred to as pUCABFCD (see FIG. 8c).

H. E$^{col}$

This example describes the production of a nucleic acid fragment containing the *Escherichia coli* bioE gene.

Figure 9:
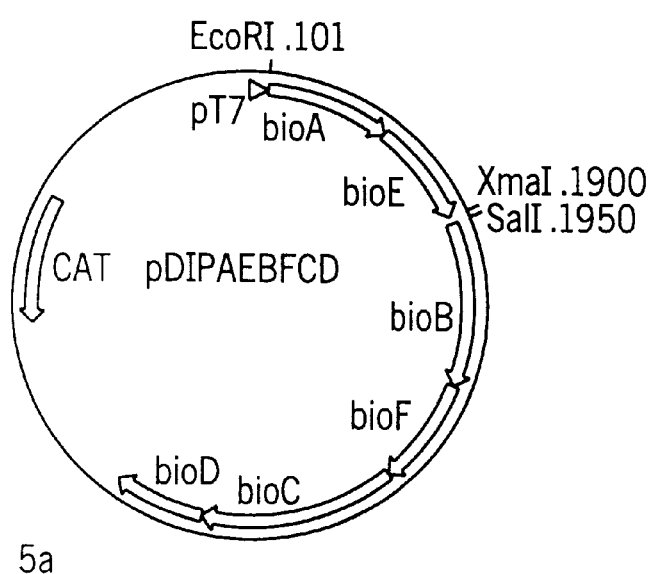

An approximately 600 bp fragment, called E$^{col}$ or bioE, containing the bioE coding sequence was isolated by PCR amplification of pDIPA$^{col}$E$^{col}$B$^{col}$F$^{col}$C$^{col}$D$^{col}$ (described in Example 1D and depicted in FIG. 5a) using primers #6 and #2 (SEQ ID NO:2 and SEQ ID NO:6, respectively). See FIG. 9a. The sequence of primer #6 (SEQ ID NO:6) is shown below. Primer #2 (SEQ ID NO:2) was described in Example 1C.

```
Primer #6 (SEQ ID NO:6)
ATATGGGCCC AAACAAGAAA GGAGGGTTC ATG
     XmaI                     Translation
                              Start site
```

Primer #6 (SEQ ID NO:6) is complementary to a nucleic acid sequence immediately upstream from and containing the translation initiation site of the *Escherichia coli* bioE gene. Primer #2 (SEQ ID NO:2) is complementary to a nucleic acid sequence including and immediately downstream from the stop codon (UAA) of the *Escherichia coli* bioE gene.

Example 2

Production of nucleic acid sequences containing coding regions of genes involved in the *Bacillus sphaericus* biotin biosynthetic pathway A. $X^{sph}W^{sph}Y^{sph}$ This example describes the production of a nucleic acid sequence containing *Bacillus sphaericus* bioX, bioW, and bioY genes.

Referring to FIG. 10, two DNA fragments containing the coding regions of *Bacillus sphaericus* bioX and bioW genes and of the *Bacillus sphaericus* bioY gene, respectively, were amplified from *Bacillus sphaericus* strain ATCC No. 10208 using PCR amplification. Ligation of the two original fragments resulted in a DNA fragment containing a bioXWY gene cluster. Details of the production of such nucleic acid sequences follow.

A 1.1 kb PCR fragment called $X^{sph}W^{sph}$ or bioXbioW, which includes the coding regions of *Bacillus sphaericus* bioX and bioW genes but lacks indigenous transcription control sequences, was synthesized using primers #7 and #8 (SEQ ID NO:7 and SEQ ID NO:8, respectively). See FIG. 10*a*. The primers contain the restriction sites XmaI and NotI, respectively, and are shown below.

```
Primer #7 (SEQ ID NO:7)
5' ATATATCCCG GGTTAACTCA AATTG 3'
          XmaI

Primer #8 (SEQ ID NO:8)
5' CCCGCGGCCG CTCAT TCA TTT TAA ATC CCC C 3'
      NotI          Translation
                    Stop site
```

Primer #7 (SEQ ID NO:7) is complementary to a nucleic acid sequence, the 3' end of which is about 28 bp upstream from the translation start site of the *Bacillus sphaericus* bioX gene. Primer #8 (SEQ ID NO:8) is complementary to a nucleic acid sequence including and immediately downstream from stop codon (UGA) of the *Bacillus sphaericus* bioW gene.

A 0.6 kb PCR fragment called $Y^{sph}$, or bioY, which includes the coding regions of the *Bacillus sphaericus* bioY gene but lacks indigenous transcription control sequences, was synthesized using primers #9 and #10 (SEQ ID NO:9 and SEQ ID NO:10, respectively). See FIG. 10*b*. The primers contain the restriction sites NotI and XmaI, respectively, and are shown below.

```
Primer #9 (SEQ ID NO:9)
5'TGAATGAGCG GCCGCGGGAG GGATGAGGGC A  3'
         NotI                      Translation
                                   Initiation
site Primer #10 (SEQ ID NO:10)
5'CTATATCCCG GAAT TCA CTA AAC ATT  3'
       XmaI      Translation
                 Stop site
```

Primer #9 (SEQ ID NO:9) is complementary to a nucleic acid sequence immediately upstream from and containing the translation initiation site of the *Bacillus sphaericus* bioY gene. Primer #10 (SEQ ID NO:10) is complementary to a nucleic acid sequence including and immediately downstream from the stop codon (UGA) of the *Bacillus sphaericus* bioY gene.

Figure 10:
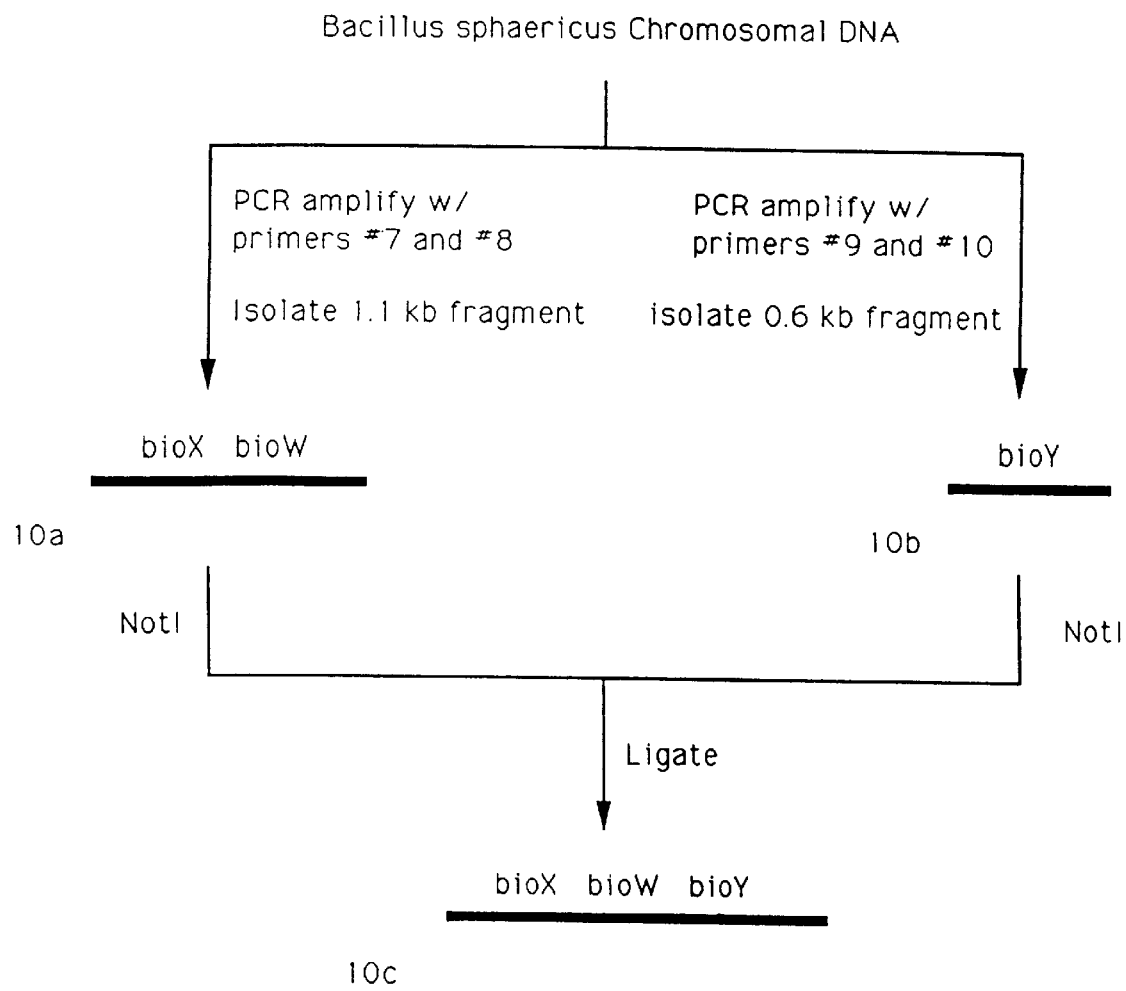

Following PCR amplification, PCR fragments $X^{sph}W^{sph}$ and $Y^{sph}$ were digested with NotI and ligated to each other and amplified by PCR to form a 1.7 kb PCR fragment referred to as $X^{sph}W^{sph}Y^{sph}$, also referred to as bioXbioWbioY (see FIG. 10*c*).

B. $X^{sph}W^{sph}F^{sph}$

Figure 11:
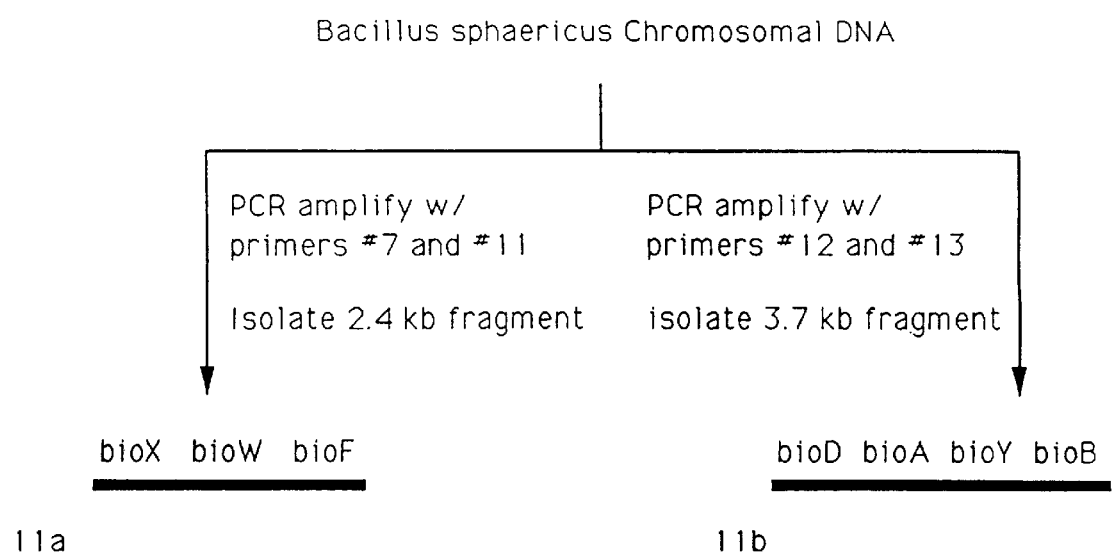

A 2.4 kb PCR fragment, called $X^{sph}W^{sph}F^{sph}$, of bioXbioWbioF, which includes the coding regions of the *Bacillus sphaericus* bioXWF gene cluster is synthesized using primers #7 and #11 (SEQ ID NO:7 and SEQ ID NO:11, respectively). See FIG. 11*a*. The primers contain the restriction sites XmaI and HindIII, respectively. Primer #7 (SEQ ID NO:7) has been described previously in Example 2A. Primer #11 (SEQ ID NO:11) is shown below.

```
Primer #11 (SEQ ID NO:11)
5' GATATAAG CTTCAAACAA TTA TAC AAT CC 3'
        HindIII        Translational
                       Stop site
```

Primer #7 (SEQ ID NO:7) is complementary to a nucleic acid sequence the 3' end of which is about 28 bp upstream from the translation start site of the *Bacillus sphaericus* bioX gene. Primer #11 (SEQ ID NO:11) is complementary to a nucleic acid sequence which includes the translational stop site of the *Bacillus sphaericus* bioF gene.

C. $D^{sph}A^{sph}Y^{sph}B^{sph}$

A 3.7 kb PCR fragment, called $D^{sph}A^{sph}Y^{sph}B^{sph}$ or bioDbioAbioYbioB, which includes the coding regions of the *Bacillus sphaericus* bioDAYB gene cluster is synthesized using primers #12 and #13 (SEQ ID NO:12 and SEQ ID NO:13, respectively). See FIG. 11*b*. The primers each contain the restriction site HindIII, and are shown below.

```
Primer #12 (SEQ ID NO:12)
5' TTTCCCAAGC TTTGCACACT TCTGTTTCGT ATCCTCA 3'
         HindIII Primer #13 (SEQ ID NO:13)
5' CCTGGGAAGC TTTCATTGAA CATTTTGTGA AAACCATCA 3'
         HindIII
```

The 3' end of Primer #12 (SEQ ID NO:12) is complementary to a nucleic acid sequence about 456 bp 5' of the translational start of the *Bacillus sphaericus* bioD gene. The 3' end of Primer #13 (SEQ ID NO:13) is complementary to a nucleic acid sequence about 54 bp 3' of the translational stop codon of the *Bacillus sphaericus* bioB gene.

Example 3

Production of recombinant molecules containing nucleic acid sequences involved in the *Bacillus sphaericus* and *Escherichia coli* biotin biosynthetic pathways A. $pDIPA^{col}X^{sph}W^{sph}Y^{sph}B^{col}F^{col}C^{col}D^{col}$ This example describes the production of a recombinant molecule containing the *Bacillus sphaericus* $X^{sph}W^{sph}Y^{sph}$ gene cluster and the entire *Escherichia coli* biotin operon, except for the *Escherichia coli* bioE gene, operatively linked to a bacteriophage T7 transcription control sequence.

Referring to FIG. 12, PCR fragment $X^{sph}W^{sph}Y^{sph}$ (produced as described in Example 2A and depicted in FIG. 10*c* as bioXbioWbioY) was digested with XmaI and ligated into recombinant molecule $pDIPA^{col}B^{col}F^{col}C^{col}D^{col}$ (prepared as described in Example 1E and depicted in FIG. 6*b*) that had been digested with XmaI. The resulting recombinant molecule is referred to as $pDIPA^{col}X^{sph}W^{sph}Y^{sph}B^{col}F^{col}C^{col}D^{col}$, or pDIPAXW-YBFCD (see FIG. 12*a*).

B. $pDIPA^{col}E^{col}X^{sph}W^{sph}Y^{sph}B^{col}F^{col}C^{col}D^{col}$

This example describes the production of a recombinant molecule containing the entire biotin operon, including the *Escherichia coli* bioE gene, and the *Bacillus sphaericus* $X^{sph}W^{sph}Y^{sph}$ gene cluster operatively linked to a bacteriophage T7 transcription control sequence.

Figure 13:
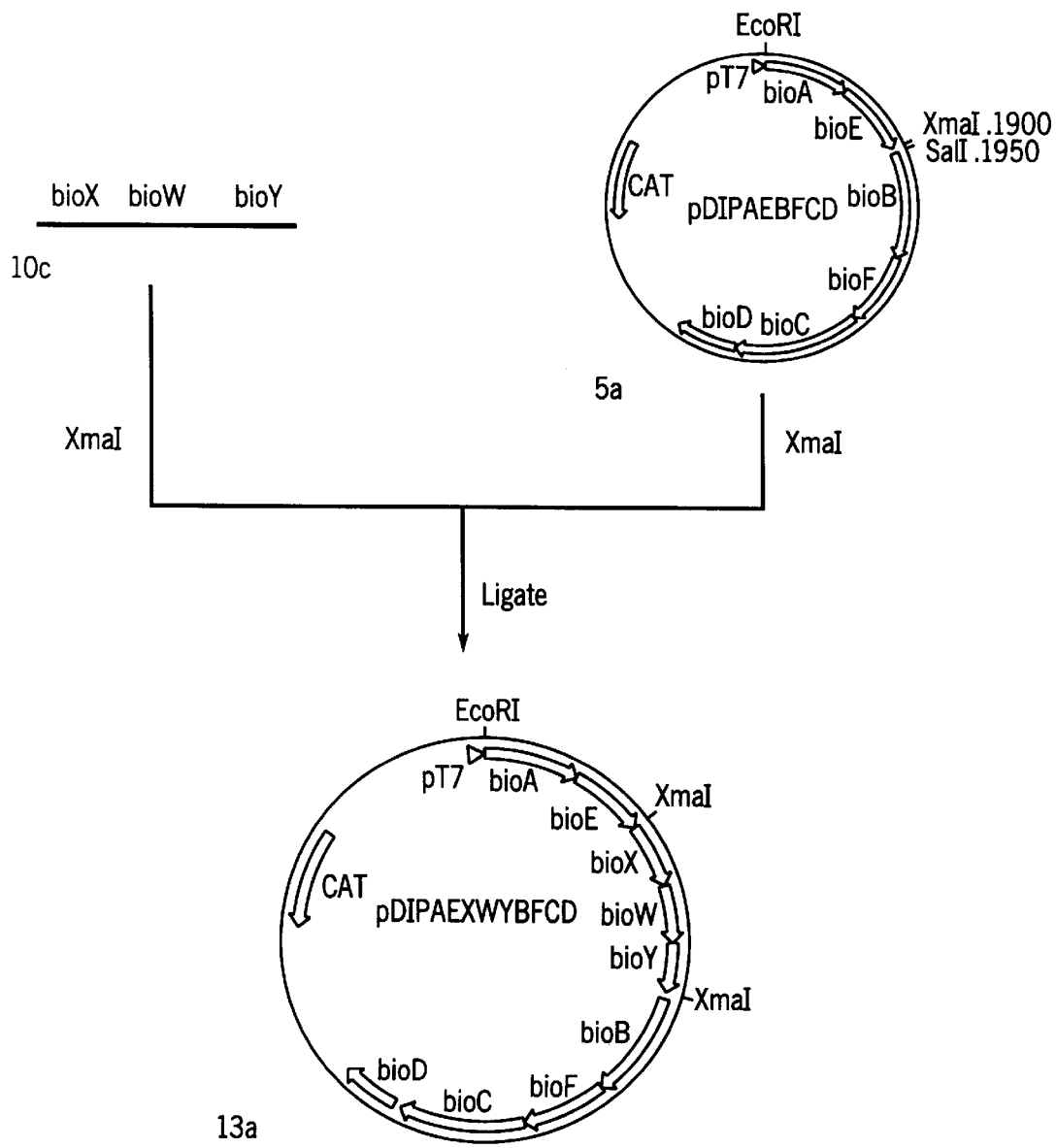

Referring to FIG. 13, PCR fragment $X^{sph}W^{sph}Y^{sph}$ (produced as described in Example 2A and depicted in FIG. 10*c* as bioXbioWbioY) was digested with XmaI and ligated to recombinant molecule $pDIPA^{col}E^{col}B^{col}F^{col}$ $C^{col}D^{col}$ (produced as described in Example 1D and shown in FIG. 5*a*) that had been digested with XmaI. The resulting recombinant molecule is referred to as $pDIPA^{col}E^{col}X^{sph}W^{sph}Y^{sph}B^{col}F^{col}C^{col}D^{col}$, or pDIPAEX-WYBFCD (see FIG. 13*a*).

C. $pDIPX^{sph}W^{sph}F^{sph}$

This example describes the production of a recombinant molecule containing the *Bacillus sphaericus* gene cluster bioXWF operatively linked to a T7 transcription control sequence.

Figure 14:
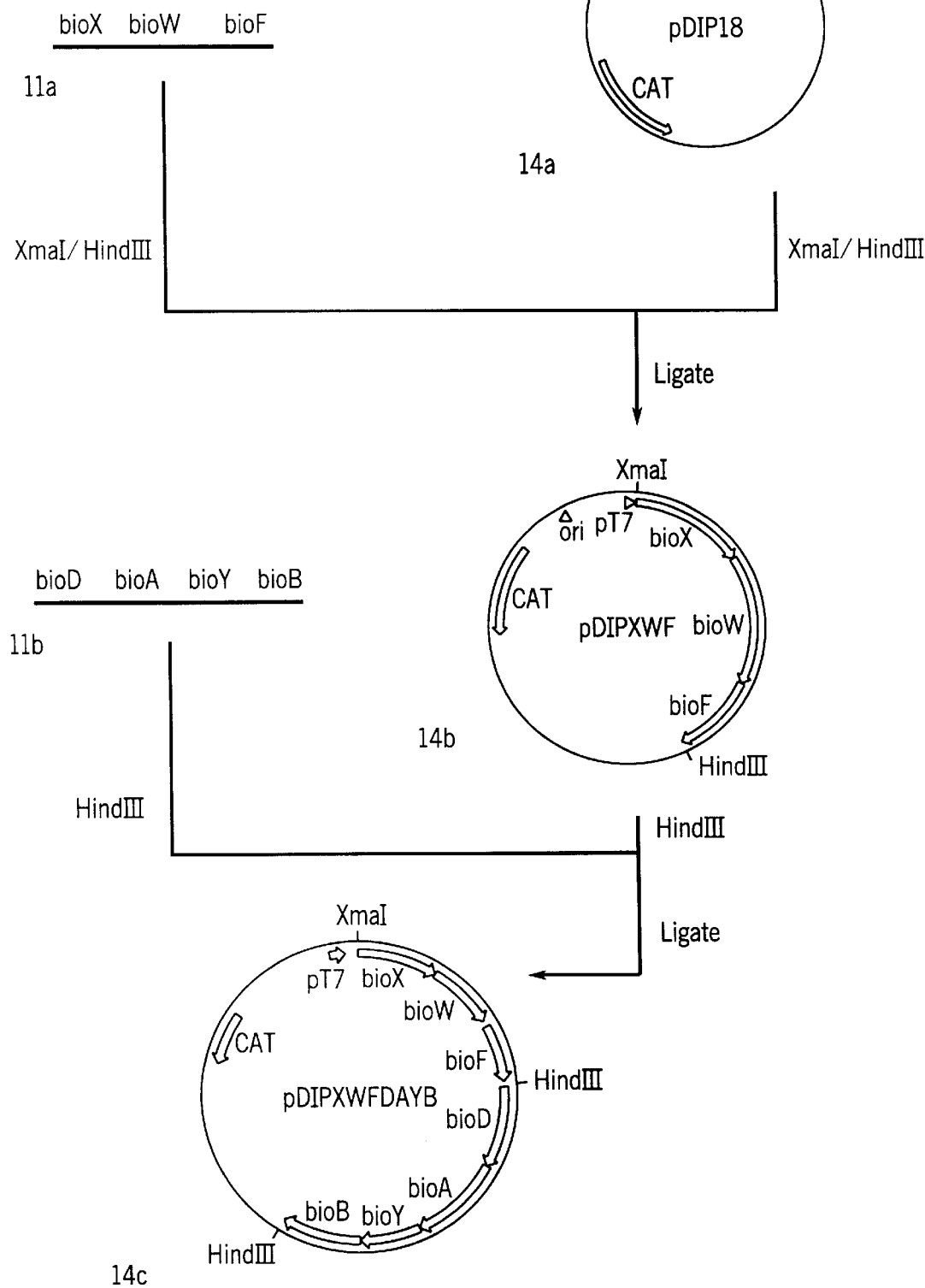
Figure 15:
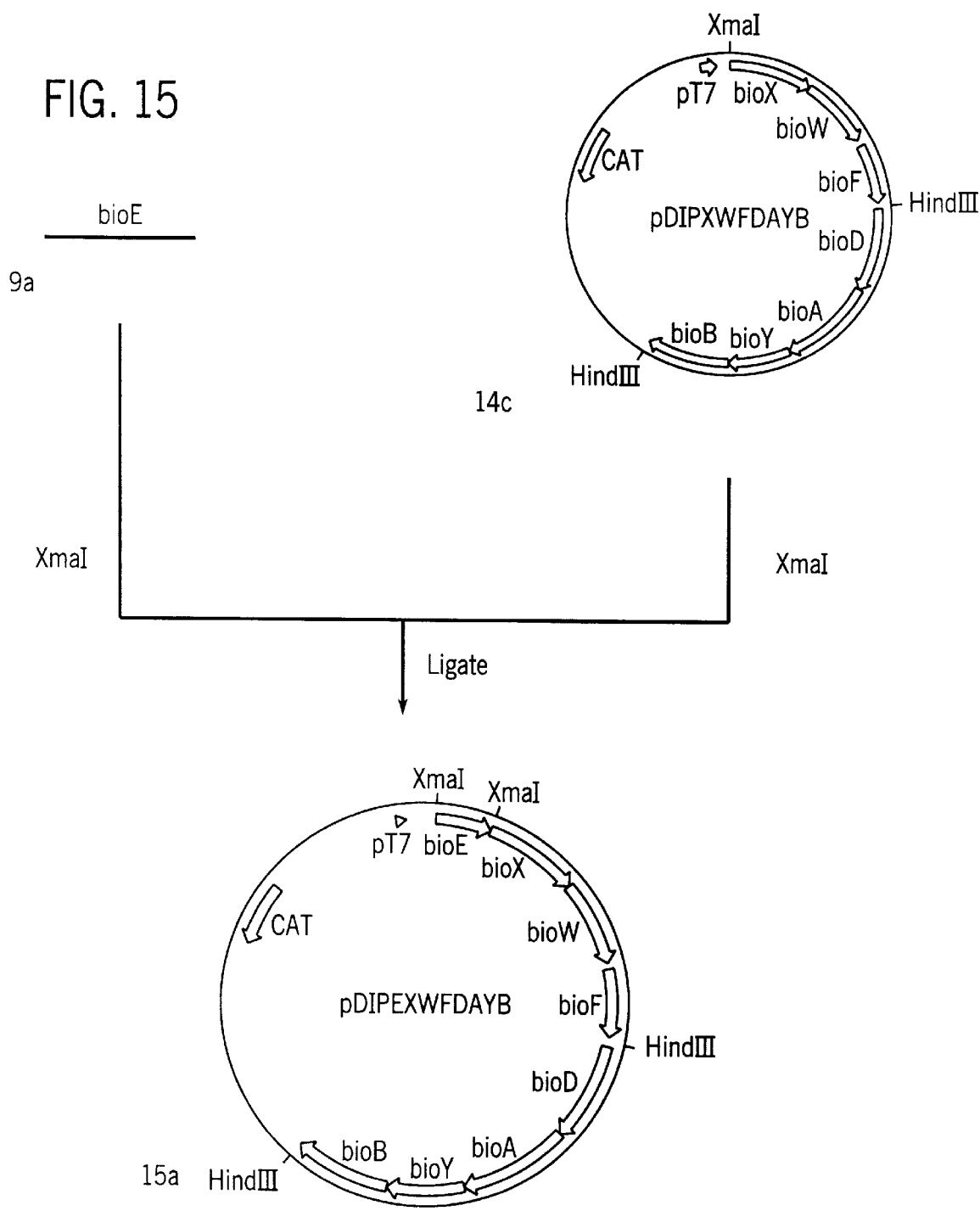

Following PCR amplification, the PCR fragment $X^{sph}$-$W^{sph}F^{sph}$ (produced as described in Example 2B and depicted in FIG. 11*a* as bioXbioWbioF) is digested with XmaI and HindIII and ligated, as shown in FIG. 14, to the expression vector pDIP18 (see FIG. 14*a*) that is digested with XmaI and HindIII. As such, the *Bacillus sphaericus* bioXWF genes are operatively linked to a T7 transcription control sequence to form the recombinant molecule $pDIPX^{sph}W^{sph}F^{sph}$, denoted pDIPXWF in FIG. 14*b*.

D. $pDIPX^{sph}W^{sph}F^{sph}D^{sph}A^{sph}Y^{sph}B^{sph}$

This example describes the production of a recombinant molecule containing the *Bacillus sphaericus* gene clusters bioXWF and bioDAYB, operatively linked to a T7 transcription control sequence.

The 3.7 kb fragment containing *Bacillus sphaericus* gene cluster bioDAYB (produced as described in Example 2C and depicted in FIG. 11*b* as bioDbioAbioYbioB) is digested with HindIII and ligated into $pDIPX^{sph}W^{sph}F^{sph}$ (produced as described in Example 3C and depicted in FIG. 14*b*) that is digested with HindIII. The correct orientation produces the recombinant molecule $pDIPX^{sph}W^{sph}F^{sph}D^{sph}A^{sph}Y^{sph}B^{sph}$, denoted pDIPXWF-DAYB as shown in FIG. 14*c*.

E. $pDIPE^{col}X^{sph}W^{sph}F^{sph}D^{sph}A^{sph}Y^{sph}B^{sph}$

This example describes the production of a recombinant molecule containing the *Escherichia coli* bioE gene associated with the *Bacillus sphaericus* gene cluster bioXWF, and the *Bacillus sphaericus* bioDAYB gene cluster. Each gene in the recombinant molecule is operatively linked to a common T7 transcription control sequence.

The $E^{col}$ fragment (described in Example 1H and depicted in FIG. 9*a* as bioE), containing the *Escherichia coli* bioE gene, is digested with XmaI and ligated into pDIPX$^{sph}$-W$^{sph}$F$^{sph}$D$^{sph}$A$^{sph}$Y$^{sph}$B$^{sph}$ (produced as described in Example 3D and depicted in FIG. 14*c*) that is digested with XmaI. The resulting plasmid is called pDIPE$^{col}$X$^{sph}$W$^{sph}$F$^{sph}$D$^{sph}$A$^{sph}$Y$^{sph}$B$^{sph}$, denoted pDIPEX-WFDAYB in FIG. 15*a*.

Example 4

Production of recombinant cells

This example describes the production of recombinant cells transformed with recombinant molecules pUCA$^{col}$B$^{col}$F$^{col}$C$^{col}$D$^{col}$, pUCA$^{col}$E$^{col}$B$^{col}$F$^{col}$C$^{col}$D$^{col}$, pDIPA$^{col}$E$^{col}$, pDIPB$^{col}$F$^{col}$C$^{col}$D$^{col}$, pDIPA$^{col}$B$^{col}$F$^{col}$C$^{col}$D$^{col}$, and pDIPA$^{col}$E$^{col}$B$^{col}$F$^{col}$C$^{col}$D$^{col}$.

A. Production of recombinant cells using *Escherichia coli* SA291 cells

Recombinant molecules pUCA$^{col}$E$^{col}$B$^{col}$F$^{col}$C$^{col}$D$^{col}$ and pUCA$^{col}$B$^{col}$F$^{col}$C$^{col}$D$^{col}$, produced as described in Examples 1F and 1G, respectively, as well as the pUC18 vector alone, were transformed into *Escherichia coli* SA291 cells (Cleary et al., pp. 2219–2223, 1972, *Proc. Natl. Acad. Sci.* 69) using techniques similar to those described in Sambrook et al., ibid. Note that in *Escherichia coli* SA291 cells, the bacterial chromosome has a deletion spanning chlA to uvrB, which includes the biotin operon; thus SA291 cells lack the entire biotin operon. Transformed cells were identified by their ability to grow on medium containing about 75 μg per ml of ampicillin. A recombinant cell transformed with pUCA$^{col}$B$^{col}$F$^{col}$C$^{col}$D$^{col}$ was denoted SA291-pUCA$^{col}$B$^{col}$F$^{col}$C$^{col}$D$^{col}$. A recombinant cell transformed with pUCA$^{col}$E$^{col}$B$^{col}$F$^{col}$C$^{col}$D$^{col}$ was denoted SA291-pUCA$^{col}$E$^{col}$B$^{col}$F$^{col}$C$^{col}$D$^{col}$. A cell transformed with pUC18 was denoted SA291-pUC18.

B. Production of recombinant cells using *Escherichia coli* BL21/DE3 cells

Recombinant molecules pDIPA$^{col}$E$^{col}$, pDIPB$^{col}$F$^{col}$C$^{col}$D$^{col}$, pDIPA$^{col}$B$^{col}$F$^{col}$C$^{col}$D$^{col}$, and pDIPA$^{col}$E$^{col}$B$^{col}$F$^{col}$C$^{col}$D$^{col}$ (produced as described in Examples 1C, 1B, 1E, and 1D, respectively), as well as expression vector pDIP18, were each transformed into *Escherichia coli* BL21/DE3 cells (Studier et al., pp.113–130, 1986, *J. Mol. Biol.,* Vol. 189) using techniques similar to those described in Sambrook et al., ibid. *Escherichia coli* BL21/DE3 cells have a T7 RNA polymerase gene 1 integrated into the genome under the control of lacUV5 promoter and operator sequences. Recombinant cells were selected for their ability to grow in the presence of about 34 μg per ml of chloramphenicol. The resulting recombinant cells were denoted BL21/DE3-pDIPA$^{col}$E$^{col}$, BL21/DE3-pDIPB$^{col}$F$^{col}$C$^{col}$D$^{col}$, BL21/DE3-pDIPA$^{col}$B$^{col}$F$^{col}$C$^{col}$D$^{col}$, and BL21/DE3-pDIPA$^{col}$E$^{col}$B$^{col}$F$^{col}$C$^{col}$D$^{col}$, respectively. Cells transformed with pDIP18 were denoted BL21/DE3-pDIP18.

Example 5

Cross-feeding studies

This example describes the use of several biotin auxotrophs as well as recombinant cells SA291-pUCA$^{col}$B$^{col}$F$^{col}$C$^{col}$D$^{col}$ and SA291-pUCA$^{col}$E$^{col}$B$^{col}$F$^{col}$C$^{col}$D$^{col}$ to determine which reaction in the biotin biosynthetic pathway is conducted by the protein encoded by the *Escherichia coli* bioE gene.

*Escherichia coli* bioD$^-$ strain R877 and bioB$^-$ strain R875 were streaked onto plates containing biotin-free nutrient agar (4 g glucose, 2 mM [millimolar] $MgSO_4$, 0.1 mM $CaCl_2$, 12.8 g $Na_2HPO_4$, 3 g of $KH_2PO_4$, 0.5 g Nacl, 1.0 g $NH_4Cl$, 0.1% vitamin free Casamino acids, 0.1% tryptophan, 0.01% thiamine, and 15 g agar per liter of medium). The plates were incubated for six hours at 30° C. Aliquots of *Escherichia coli* bioD$^-$ strain R877, bioB$^-$ strain R875, bioC$^-$ strain R876, bioF$^-$ strain R874, and bioA$^-$ strain R879, (all available from *Escherichia coli* Genetic Stock Center, New Haven, Conn.) as well as SA291-pUCA$^{col}$B$^{col}$F$^{col}$C$^{col}$D$^{col}$ and SA291-pUCA$^{col}$E$^{col}$B$^{col}$F$^{col}$C$^{col}$D$^{col}$ cells (produced as described in Example 4A) were cross-streaked onto the plates streaked with either bioD$^-$ strain R877 or bioB$^-$ strain R875. The cross-streaked plates were grown for forty-eight hours at 30° C.

Growth patterns visible on the plates indicated that the bioD$^-$ cells were able to cross-feed the bioC$^-$, bioF$^-$, and bioA$^-$ cells. The bioD$^-$ cells, however, could not cross-feed the bioB$^-$ cells or the SA291-pUCA$^{col}$B$^{col}$F$^{col}$C$^{col}$D$^{col}$ cells. The bioB$^-$ cells, however, could cross-feed the SA29l-pUCA$^{col}$B$^{col}$F$^{col}$C$^{col}$D$^{col}$ cells as well as the bioD$^-$, bioC$^-$, bioF$^-$, and bioA$^-$ cells. Referring to FIG. 1, the results indicate that the bioE gene encodes an enzyme active in the biotin biosynthesis pathway following the activity encoded by the bioD gene and before the activity encoded by the bioB gene. Since the product of the reaction catalyzed by the enzyme encoded by the bioE gene has properties characteristic of desthiobiotin (e.g., stability and ability to bind to avidin) whereas the product of the reaction catalyzed by the enzyme encode by the bioD gene is labile and unable to bind to avidin, it is believed that the enzyme encoded by the *Escherichia coli* bioE gene is desthiobiotin synthetase.

Example 6

Growth studies using recombinant cells SA291-pUCA$^{col}$E$^{col}$B$^{col}$F$^{col}$C$^{col}$D$^{col}$ or SA291-pUCA$^{col}$B$^{col}$F$^{col}$C$^{col}$D$^{col}$ The requirement of the bioE gene for biotin biosynthesis was confirmed by comparing the growth of SA291-pUCA$^{col}$E$^{col}$B$^{col}$F$^{col}$C$^{col}$D$^{col}$ and SA291-pUCA$^{col}$B$^{col}$F$^{col}$C$^{col}$D$^{col}$ cells in the presence or absence of biotin.

Growth studies were performed by culturing SA291 cells and recombinant cells SA291-pUCA$^{col}$E$^{col}$B$^{col}$F$^{col}$C$^{col}$D$^{col}$ and SA291-pUCA$^{col}$B$^{col}$F$^{col}$C$^{col}$D$^{col}$ (produced as described in Example 4A) in M9CAT, a biotin-free nutrient broth containing 4 g glucose, 2 mM $MgSO_4$, 0.1 mM $CaCl_2$, 12.8 g $Na_2HPO_4$, 3 g of $KH_2PO_4$, 0.5 g NaCl, 1.0 g $NH_4Cl$, 0.1% vitamin free Casamino acids, 0.1% tryptophan, 0.01% thiamine, and 25 mg ampicillin per liter of medium, in the presence or absence of 1.4 nM (nanomolar) biotin or 5 nM desthiobiotin (DTB). The results shown in Table 2 indicate that SA291-pUC18 cells and SA291-pUCA$^{col}$B$^{col}$F$^{col}$C$^{col}$D$^{col}$ (denoted SA291-ABFCD) cells required biotin for growth whereas SA291-pUCA$^{col}$E$^{col}$B$^{col}$F$^{col}$C$^{col}$D$^{col}$ (denoted SA291-pUCAEBFCD) cells were able to grow in the absence of biotin. SA291-pUCA$^{col}$B$^{col}$F$^{col}$C$^{col}$D$^{col}$ and SA291-pUCA$^{col}$E$^{col}$B$^{col}$F$^{col}$C$^{col}$D$^{col}$ cells were each able to grow in minimal medium supplemented with desthiobiotin, which supports identification of the enzyme encoded by the *Escherichia coli* bioE gene as being a desthiobiotin synthetase.

TABLE 2

Comparison of the ability of SA291 cells and recombinant cells to grow in the presence and absence of biotin

| Growth Media × Strain/plasmid | M9CAT | M9CAT + biotin | M9CAT + DTB |
|---|---|---|---|
| SA291-pUC18 | ---[1] | +++[2] | --- |
| SA291-pUCAEBFCD | +++ | +++ | +++ |
| SA291-pUCABFCD | --- | +++ | +++ |

[1]"---" indicates lack of growth
[2]"+" indicates growth

These results indicate that the *Escherichia coli* bioE gene, as well as the other genes encoding enzymes active in biotin biosynthesis contained on the pUCA$^{col}$E$^{col}$B$^{col}$F$^{col}$C$^{col}$D$^{col}$ recombinant molecule, are required to rescue the ability of cells lacking the biotin operon to grow in the absence of biotin.

Example 7

Biotin production by BL21/DE3-pDIPA$^{col}$ E$^{col}$B$^{col}$F$^{col}$C$^{col}$D$^{col}$, BL21/DE3-pDIPB$^{col}$F$^{col}$C$^{col}$D$^{col}$, BL21/DE3-pDIPA$^{col}$E$^{col}$, and BL21/DE3-pDIP18

This example describes studies demonstrating the importance of a DNA fragment including the *Escherichia coli* bioA and bioE genes in production of true biotin.

Figure 16:
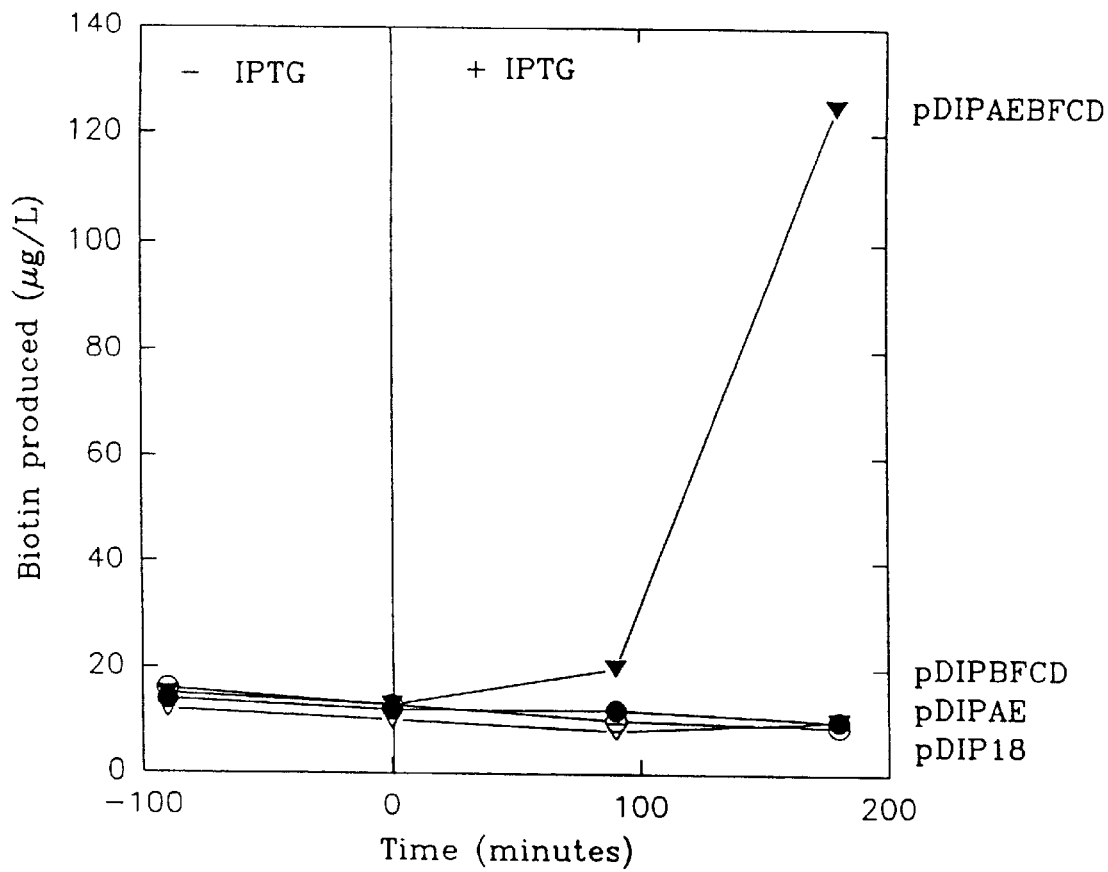
FIGS. 16 and 17 illustrate a time course of biotin production by certain recombinant cells of the present invention.

Recombinant cells BL21/DE3-pDIPA$^{col}$E$^{col}$B$^{col}$F$^{col}$C$^{col}$D$^{col}$, BL21/DE3-pDIPB$^{col}$F$^{col}$C$^{col}$D$^{col}$, BL21/DE3-pDIPA$^{col}$E$^{col}$, and BL21/DE3-pDIP18 (produced as described in Example 4B) were cultured in shake flasks containing LB broth (10 g of bacto-tryptone, 5 g of bacto-yeast, and 10 g NaCl per liter of medium) plus 34 μg/ml chloramphenicol. When the cells reached an OD$_{600}$ of about 0.7 units in LB broth, IPTG was added to a final concentration of 0.5 mM IPTG to induce expression of T7 RNA polymerase and, hence, expression of genes on the recombinant molecules. Supernatant samples were collected 90 minutes before IPTG induction as well as at 0, 90, and 180 minutes after IPTG induction and measured for true biotin content using a standard microbiological assay (Ogata et al., pp. 889–894, 1965, Agr. Biol. Chem., Vol. 29). The results are shown in FIG. 16. The amount of true biotin produced by the BL21/DE3-pDIPA$^{col}$E$^{col}$B$^{col}$F$^{col}$C$^{col}$D$^{col}$ cells (denoted pDIPAEBFCD in the Figure) was at least about 13-fold higher than that produced by recombinant cells BL21/DE3-pDIPA$^{col}$E$^{col}$ (denoted pDIPAE), or BL21/DE3-pDIPB$^{col}$F$^{col}$C$^{col}$D$^{col}$ (denoted pDIPBFCD), or by BL21/DE3-pDIP18 cells (denoted pDIP18). Thus, cells transformed with *Escherichia coli* bioA and bioE genes, in addition to *Escherichia coli* bioB, bioF, bioC, and bioD genes, are capable of producing significantly increased amounts of true biotin.

Example 8

Biotin production by recombinant cells BL21/DE3-pDIPA$^{col}$E$^{col}$B$^{col}$F$^{col}$C$^{col}$D$^{col}$, BL21/DE3-pDIPA$^{col}$B$^{col}$F$^{col}$C$^{col}$D$^{col}$, BL21/DE3-pDIPB$^{col}$F$^{col}$C$^{col}$D$^{col}$, and BL21/DE3-pDIPA$^{col}$E$^{col}$ This example describes studies demonstrating the importance of the *Escherichia coli* bioE gene in increasing the production of true biotin.

Figure 17:
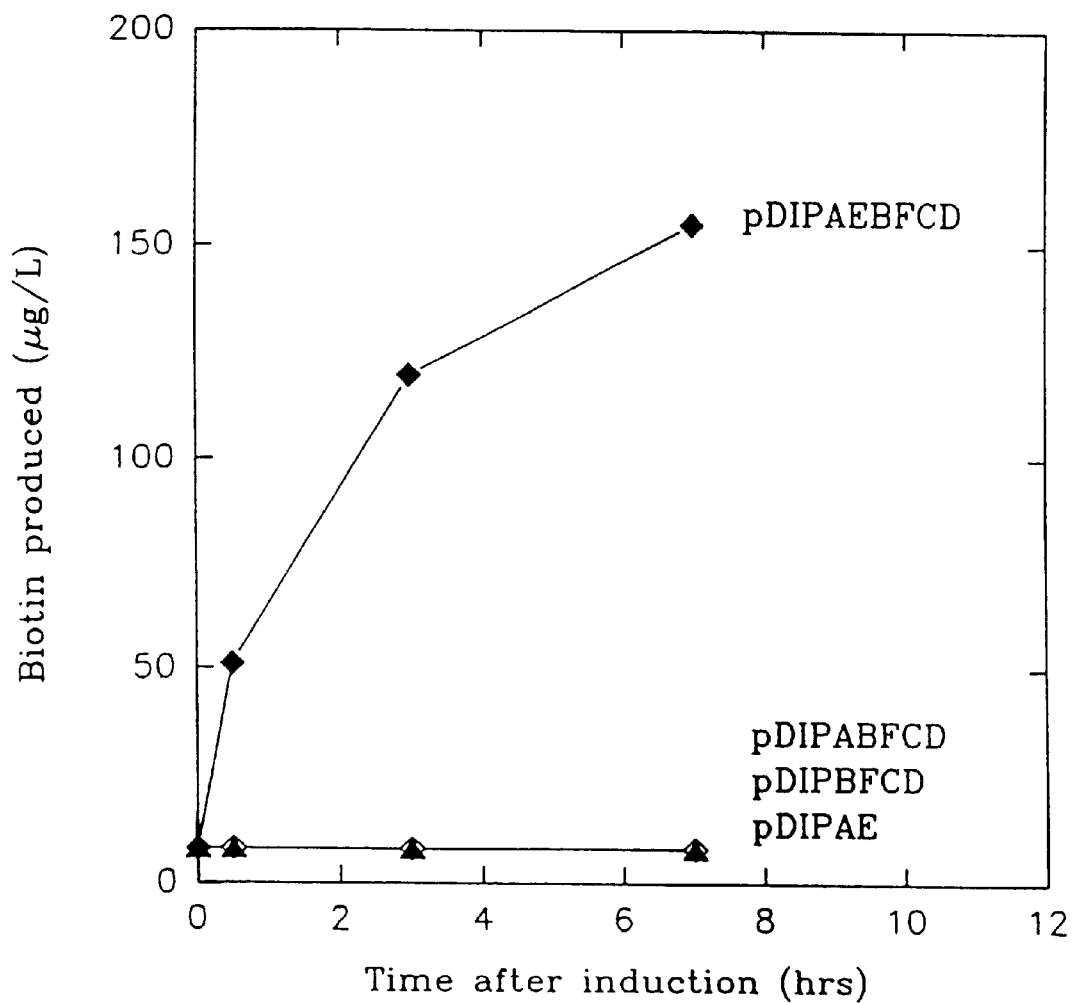
Figure 18:
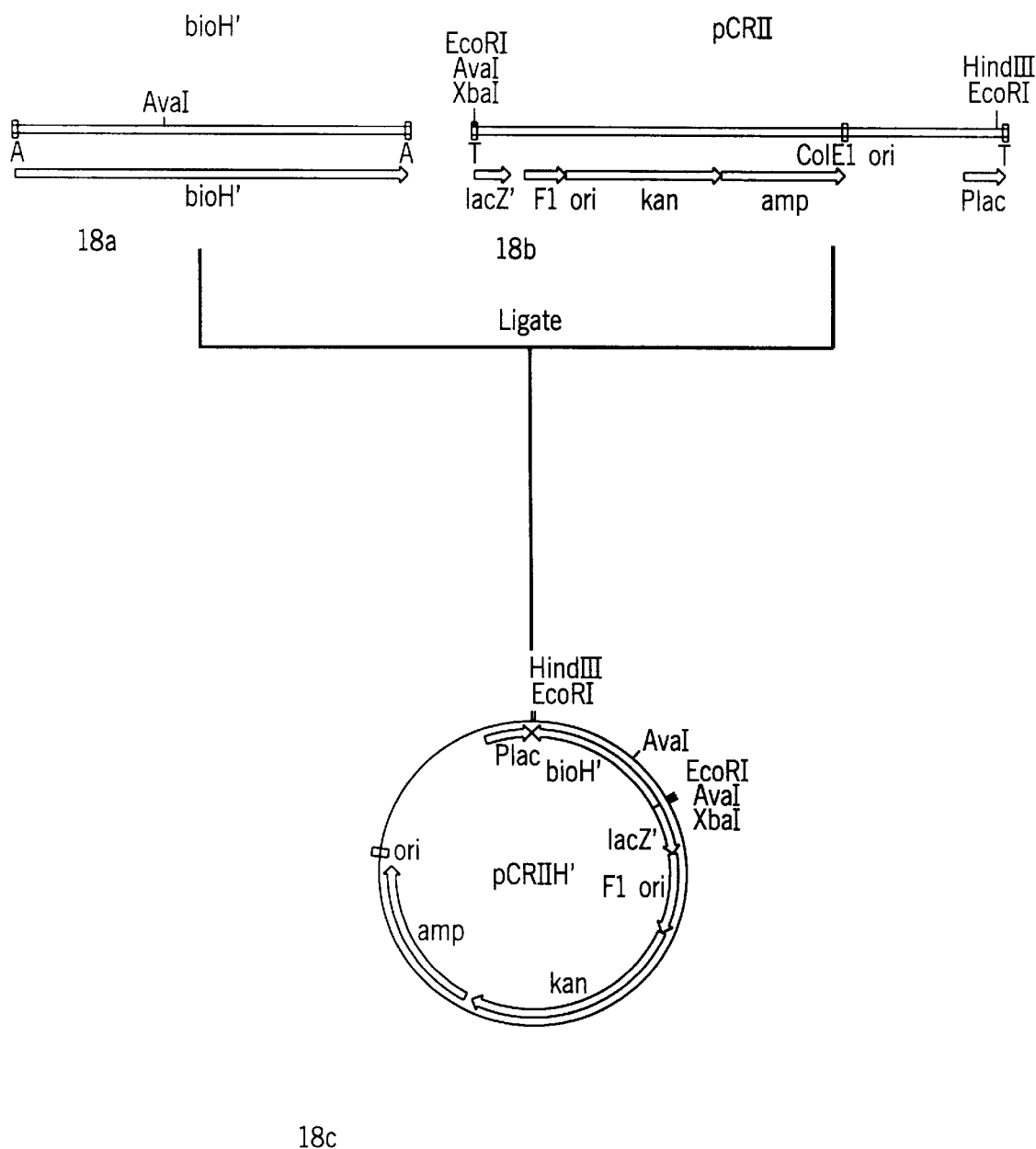
FIGS. 18 through 22 contain schematic drawings of methods to produce additional nucleic acid sequences and recombinant molecules containing *Escherichia coli* genes encoding enzymes involved in biotin production.

Recombinant cells BL21/DE3-pDIPA$^{col}$E$^{col}$B$^{col}$F$^{col}$C$^{col}$D$^{col}$, BL21/DE3-pDIPA$^{col}$B$^{col}$F$^{col}$C$^{col}$D$^{col}$, BL21/DE3-pDIPB$^{col}$F$^{col}$C$^{col}$D$^{col}$, and BL21/DE3-pDIPA$^{col}$E$^{col}$ (produced as described in Example 4B) were cultured in shake flasks as described in Example 7. Supernatant samples were collected at 0, 0.5, 3, and 7 hours after IPTG induction and measured for true biotin content using the microbiological assay cited in Example 7. The results are shown in FIG. 17. The results indicate that the amount of true biotin produced by the BL21/DE3-pDIPA$^{col}$E$^{col}$B$^{col}$F$^{col}$C$^{col}$D$^{col}$ cells (denoted in the Figure as pDIPAEBFCD) was about 16-fold higher than the amount produced by recombinant cells BL21/DE3-pDIPA$^{col}$E$^{col}$ (denoted pDIPAE), BL21/DE3-pDIPB$^{col}$F$^{col}$C$^{col}$D$^{col}$ (denoted pDIPBFCD), or BL21/DE3-pDIPA$^{col}$B$^{col}$F$^{col}$C$^{col}$D$^{col}$ (denoted pDIPABFCD). Thus, expression of the bioE gene in combination with bioA, bioB, bioF, bioC, and bioD genes, significantly increases true biotin production.

Example 9

Biotin production by recombinant cells transformed with recombinant molecules pDIPA$^{col}$B$^{col}$F$^{col}$C$^{col}$D$^{col}$, A$^{col}$E$^{col}$B$^{col}$F$^{col}$C$^{col}$D$^{col}$, pDIPA$^{col}$X$^{sph}$W$^{sph}$Y$^{sph}$B$^{col}$F$^{col}$C$^{col}$D$^{col}$, or pDIPA$^{col}$E$^{co}$X$^{sph}$W$^{sph}$Y$^{sph}$B$^{col}$F$^{col}$C$^{col}$D$^{col}$ This example describes studies that compare the production of total biotin, true biotin and biotin vitamers by cells transformed with recombinant molecules containing or lacking the *Escherichia coli* bioE gene.

Recombinant molecules pDIPA$^{col}$B$^{col}$F$^{col}$C$^{col}$D$^{col}$, A$^{col}$E$^{col}$B$^{col}$F$^{col}$C$^{col}$D$^{col}$, pDIPA$^{col}$X$^{sph}$W$^{sph}$Y$^{sph}$B$^{col}$F$^{col}$C$^{col}$D$^{col}$, and pDIPA$^{col}$E$^{col}$X$^{sph}$W$^{sph}$Y$^{sph}$B$^{col}$F$^{col}$C$^{col}$D$^{col}$ (produced as described in Examples 1E, 1D, 3A, and 3B, respectively) are transformed into *Escherichia coli* BL21/DE3 cells using techniques described in Example 4. The resulting recombinant cells are referred to as BL21/DE3-pDIPA$^{col}$B$^{col}$F$^{col}$C$^{col}$D$^{col}$ (denoted pDIPABFCD), BL21/DE3-pDIPA$^{col}$E$^{col}$B$^{col}$F$^{col}$C$^{col}$D$^{col}$ (denoted pDIPAEBFCD), BL21/DE3-pDIPA$^{col}$X$^{sph}$W$^{sph}$Y$^{sph}$B$^{col}$F$^{col}$C$^{col}$D$^{col}$ (denoted pDIPAXWYBFCD), and BL21/DE3-pDIPA$^{col}$E$^{col}$X$^{sph}$W$^{sph}$Y$^{sph}$B$^{col}$F$^{col}$C$^{col}$D$^{col}$ (denoted pDIPAEXWYBFCD). The recombinant cells are cultured in shake flasks as described in Example 7 with pimelic acid added to the media to a final concentration of 0.5 g/L in cultures of BL21/DE3-pDIPA$^{col}$X$^{sph}$W$^{sph}$Y$^{sph}$B$^{col}$F$^{col}$C$^{col}$D$^{col}$ and BL21/DE3-pDIPA$^{col}$E$^{col}$X$^{sph}$W$^{sph}$Y$^{sph}$B$^{col}$F$^{col}$C$^{col}$D$^{col}$. Supernatant samples are collected at 3 hours after IPTG induction and measured for total biotin, true biotin, and biotin vitamer content using the microbiological assays described in Ogata et al., pp. 889–894, 1965, Agr. Biol. Chem., Vol. 29. The results demonstrate that the bioE gene product is required for the efficient production of true biotin from either endogenous (compare pDIPABFCD to pDIPAEBFCD) or exogenous (compare pDIPAXWYBFCD to pDIPAEXWYBFCD) sources of pimelic acid.

Example 10

Biotin production by recombinant cells BL21/DE3-pDIPE$^{col}$X$^{sph}$W$^{sph}$F$^{sph}$D$^{sph}$A$^{sph}$Y$^{sph}$B$^{sph}$ and BL21/DE3-pDIPX$^{sph}$W$^{sph}$F$^{sph}$D$^{sph}$A$^{sph}$Y$^{sph}$B$^{sph}$ This example describes studies that compare the production of total biotin, true biotin and biotin vitamers by cells transformed with recombinant molecules containing the *Bacillus sphaericus* genes bioXWFDAYB, with or without the *Escherichia coli* bioE gene.

Recombinant molecules pDIPE$^{col}$X$^{sph}$W$^{sph}$F$^{sph}$D$^{sph}$A$^{s-}$$_{ph}$Y$^{sph}$B$^{sph}$ and pDIPX$^{sph}$W$^{sph}$F$^{sph}$D$^{sph}$A$^{sph}$Y$^{sph}$B$^{sph}$, (produced as described in Examples 3E and 3D) as well as the plasmid pDIP18, are transformed into *Escherichia coli* BL21/DE3 cells using techniques described in Example 4 to produce, respectively, recombinant cells BL21/DE3-pDIPE$^{col}$X$^{sph}$W$^{sph}$F$^{sph}$D$^{sph}$A$^{sph}$Y$^{sph}$B$^{sph}$ and BL21/DE3-pDIPX$^{sph}$W$^{sph}$F$^{sph}$D$^{sph}$A$^{sph}$Y$^{sph}$B$^{sph}$, as well as BL21/DE3-pDIP18.

The recombinant cells are cultured in shake flasks containing LB broth (10 g of bacto-tryptone, 5 g of bacto-yeast, and 10 g NaCl per liter of medium) plus about 75 μg/ml ampicillin and 0.5 g/L pimelic acid. When the cells reach an OD$_{600}$ of about 0.7 units in LB broth, IPTG is added to a final concentration of 0.5 mM IPTG to induce expression of genes on the recombinant molecules. Supernatant samples are collected about 3 hours after IPTG induction and measured for total biotin, true biotin, and biotin vitamer content as described in Example 9.

Figure 22:
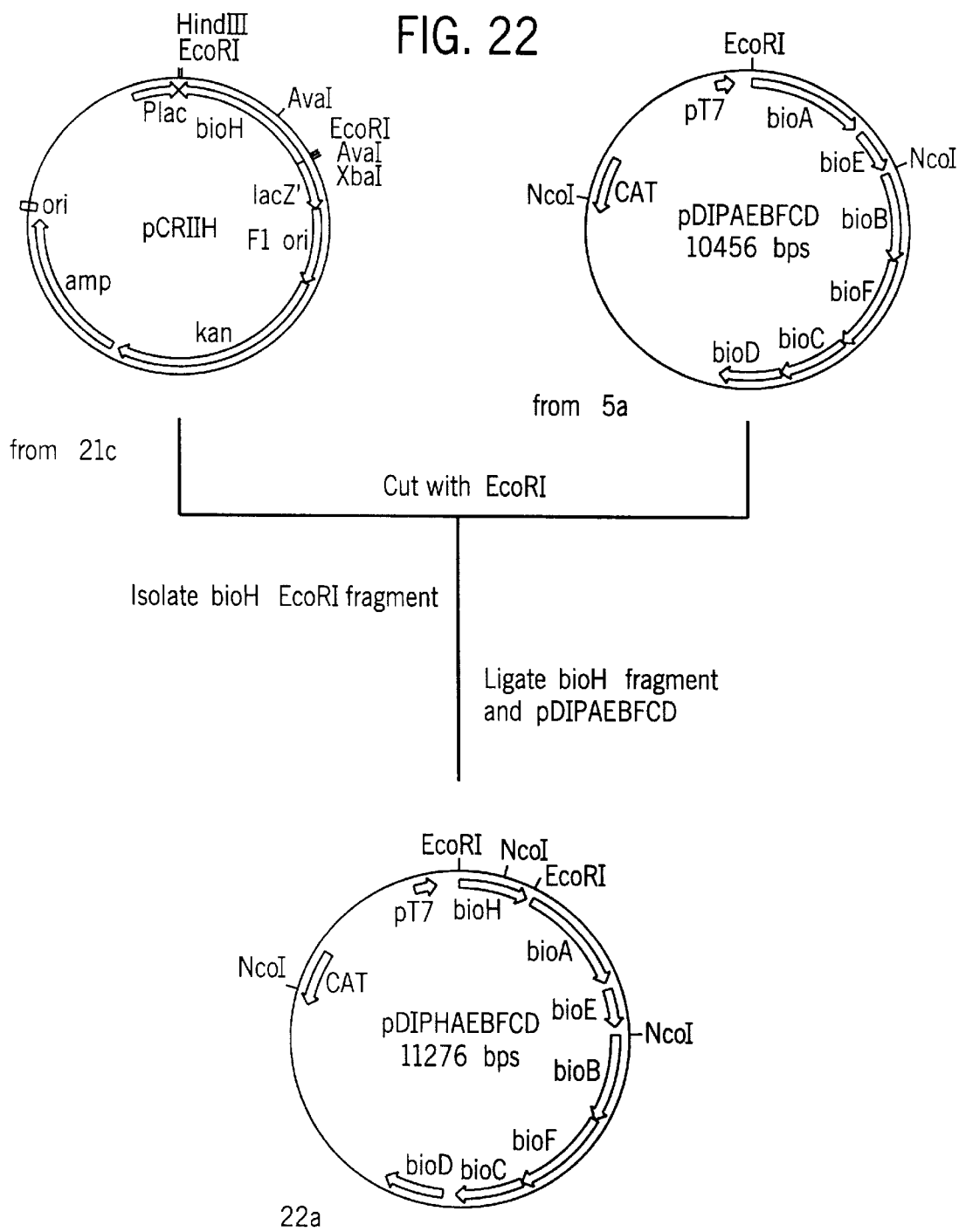

The amount of true biotin that is produced by the BL21/DE3-pDIPE$^{col}$X$^{sph}$W$^{sph}$F$^{sph}$D$^{sph}$A$^{sph}$Y$^{sph}$B$^{sph}$ cultures is significantly higher than that produced by either BL21/DE3-pDIPX$^{sph}$W$^{sph}$F$^{sph}$D$^{sph}$A$^{sph}$Y$^{sph}$B$^{sph}$ (which produces primarily biotin vitamers) or BL21/DE3-pDIP18 cultures. The results indicate that recombinant cells transformed with the *Escherichia coli* bioE gene as well as the *Bacillus sphaericus* bioXWFDAYB genes are capable of converting increased amounts of biotin vitamers to true biotin, unlike recombinant cells transformed with recombinant molecules containing the *Bacillus sphaericus* bioXWFDAYB genes but lacking the *Escherichia coli* bioE gene.

Example 11

Production of recombinant molecules containing the *Escherichia coli* bioH nucleic acid sequence A. pCKRH$^{\prime col}$ This example describes the production of a recombinant molecule containing the coding region of the *Escherichia coli* bioH gene operatively linked to a tac transcription control sequence.

An 820 bp DNA fragment containing the coding region, but lacking indigenous transcription control sequences, of the *Escherichia coli* bioH gene, and denoted H$^{\prime col}$, or bioH', was produced by PCR amplification of a portion of W3110 *Escherichia coli* genomic DNA using primers #14 and #15. (SEQ ID NO:14 and SEQ ID NO:15, respectively) See FIG. 18*a*. Primers #14 and #15 (SEQ ID NO:14 and SEQ ID NO:15, respectively) are shown below.

```
Primer #14 (SEQ ID NO:14)
5' GCTCTAGAGC AAGGAGGACA ATA ATG AAT AAC ATC TGG
TGG Ribosome       Translation
             Binding Site   Initiation Site Primer #15 (SEQ ID NO:15)
5' CCGGGTTCGA AACAT CTG CTT CAA CGC CAC CAG CAG 3'
```

Primer #14 (SEQ ID NO:14) is complementary to a nucleic acid sequence containing the translation initiation site of the *Escherichia coli* bioH gene. Primer #14 (SEQ ID NO:14) also contains an *Escherichia coli* consensus ribosome binding site, as shown. Primer #15 (SEQ ID NO:15) is complementary to a nucleic acid sequence including the 3' end of the coding region of the *Escherichia coli* bioH gene. Note that Primer #15 (SEQ ID NO:15) does not contain a stop codon in the appropriate reading frame. As such, expression of the *Escherichia coli* bioH gene from the pCKRH$^{\prime col}$ recombinant molecule described hereinafter results in the production of a protein containing amino acids at its carboxyl terminus encoded by the sequences in pCKR101 immediately adjacent to the site at which H$^{\prime col}$ was inserted.

The H$^{\prime col}$ PCR product was purified from an 0.7% agarose gel and ligated as shown in FIG. 18 to PCRII (see FIG. 18*b;* vector provided with the TA cloning kit from Invitrogen, San Diego, Calif.) to form plasmid pCRIIH$^{\prime col}$, denoted pCRIIH' in FIG. 18*c*.

Referring to FIG. 19, plasmid pCRIIH$^{\prime col}$ (depicted in FIG. 18*c*) was restricted with XbaI and HindIII to produce an 820 bp fragment containing the *Escherichia coli* bioH gene. The 820-bp fragment was ligated to vector pCKR101 (see FIG. 19*a* and Magnuson et al., ibid.) that had been restricted with XbaI and HindIII. The resulting recombinant molecule, pCKRH$^{\prime col}$, denoted pCKRH' in FIG. 19*b,* contains the *Escherichia coli* bioH gene operatively linked to a tac transcription control sequence.

B. pDIPH$^{\prime col}$A$^{col}$E$^{col}$B$^{col}$F$^{col}$C$^{col}$D$^{col}$

This example describes the production of a recombinant molecule containing the coding region of the *Escherichia coli* bioH gene and the coding regions of each of the genes of the *Escherichia coli* biotin operon all operatively linked to a bacteriophage T7 transcription control sequence.

An 820-bp EcoRI fragment containing H$^{\prime col}$ was produced by restricting recombinant molecule pCKRH$^{\prime col}$ (produced as described in Example 11A and depicted in FIG. 19*b*) with EcoRI and isolating the 820 bp fragment (see FIG. 20). The EcoRI fragment was ligated to recombinant molecule pDIPA$^{col}$E$^{col}$B$^{col}$F$^{col}$C$^{col}$D$^{col}$ (produced as described in Example 1D and shown in FIG. 5*a*) that had been digested with EcoRI. The resulting recombinant molecule, referred to as pDIPH$^{\prime col}$A$^{col}$E$^{col}$B$^{col}$F$^{col}$C$^{col}$D$^{col}$ or pDIPH'AEBFCD, is shown in FIG. 20*a*.

C. pDIPH$^{col}$A$^{col}$E$^{col}$B$^{col}$F$^{col}$C$^{col}$D$^{col}$

This example describes the production of another recombinant molecule containing the coding region of the *Escherichia coli* bioH gene and the coding regions of each of the genes of the *Escherichia coli* biotin operon all operatively linked to a bacteriophage T7 transcription control sequence.

An 820 bp DNA fragment containing the coding region, but lacking indigenous transcription control sequences, of the *Escherichia coli* bioB gene, and denoted H$^{col}$, or bioH, is produced by PCR amplification of a portion of W3110 *Escherichia coli* genomic DNA using primers #16 and #17 (SEQ ID NO:16 and SEQ ID NO:17, respectively). See FIG. 21*a*. Primers #16 and #17 (SEQ ID NO:16 and SEQ ID NO:17, respectively) are shown below.

```
Primer #16 (SEQ ID NO:16)
5' GAAGGAGGAA AAAA ATGAAT AAC ATC TGG TG 3'
     Ribosome      Translation
     Binding Site  Initiation Site Primer #17 (SEQ ID NO:17)
5' GCCAC CTA CAC CTG CTT CAA C 3'
         Translation
         Stop Codon
```

Primer #16 (SEQ ID NO:16) is complementary to a nucleic acid sequence containing the translation initiation site of the *Escherichia coli* bioH gene. Primer #16 (SEQ ID NO:16) also contains an *Escherichia coli* consensus ribosome binding site, as shown. Primer #17 (SEQ ID NO:17) is complementary to a nucleic acid sequence immediately adjacent to and including a translation stop codon of the *Escherichia coli* bioH gene.

The H$^{col}$ PCR product is purified from an 0.7% agarose gel and ligated as shown in FIG. 21 to PCRII (see FIG. 21*b*) to form plasmid pCRIIH$^{col}$, denoted PCRIIH in FIG. 21*c*.

Referring to FIG. 22, plasmid pCRIIH$^{col}$ (depicted in FIG. 21*c*) is restricted with EcoRI to produce an 820-bp EcoRI fragment denoted H$^{col}$ or bioH. The EcoRI fragment is ligated to recombinant molecule pDIPA$^{col}$E$^{col}$B$^{col}$F$^{col}$C$^{co}$-$_lD^{col}$ (produced as described in Example 1D and shown in FIG. 5a) that is digested with EcoRI. The resulting recombinant molecule, referred to as pDIPH$^{col}$A$^{col}$E$^{col}$B$^{col}$F$^{col}$C$^{co}$-$_lD^{col}$ or pDIPHAEBFCD, is shown in FIG. 22a.

Example 12

Ability of pCKRH$^{1col}$ to rescue an *Escherichia coli* bioH⁻ strain

This example describes the ability of a recombinant molecule containing the coding region of the *Escherichia coli* bioH gene operatively linked to a tac transcription control sequence to complement an *Escherichia coli* bioH⁻ strain, thereby enabling the transformed strain to grow in the absence of biotin.

Figure 19:
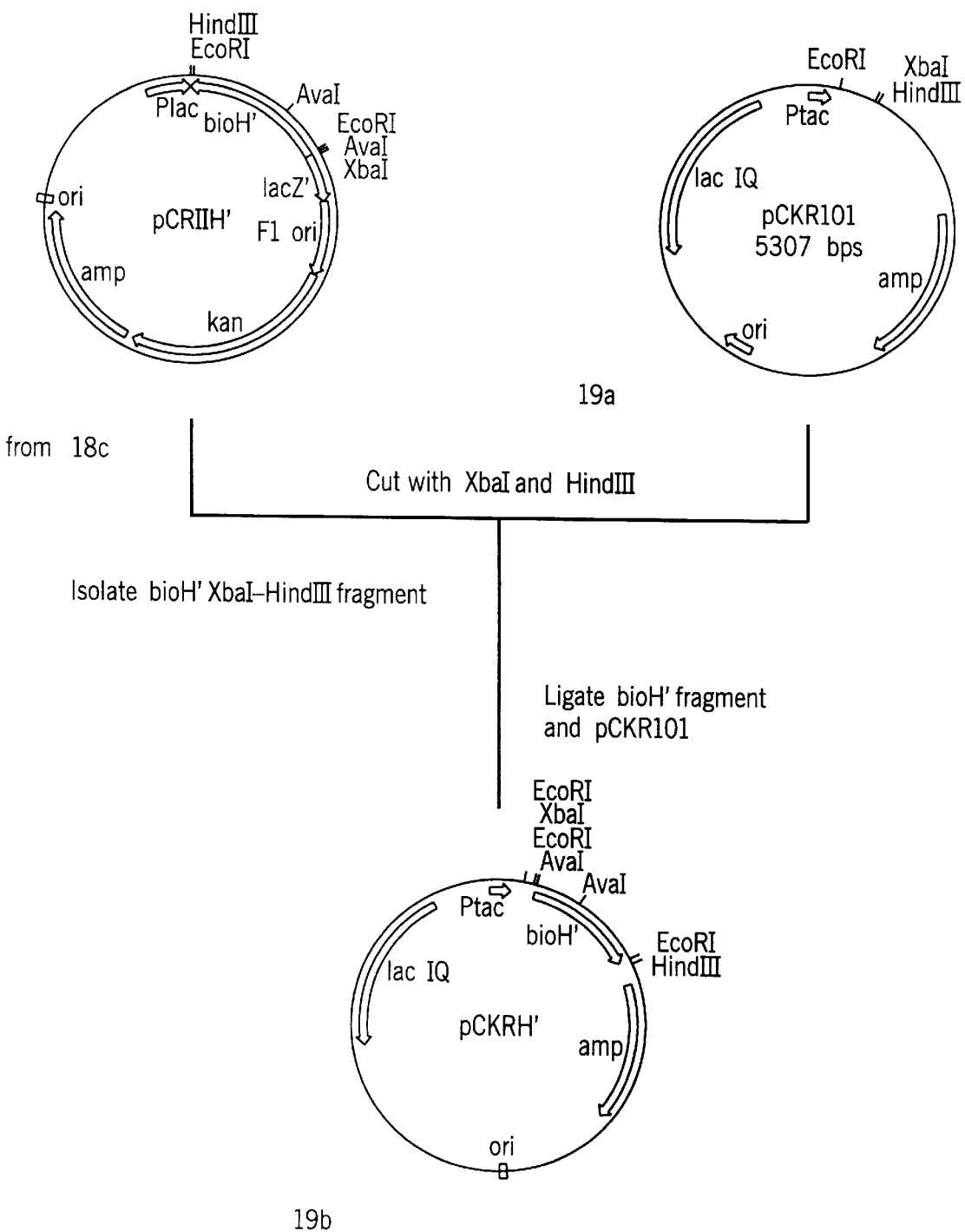

Recombinant molecule pCKRH$^{1col}$ (produced as described in Example 11A and depicted in FIG. 19b) was transformed into *Escherichia coli* bioH⁻ strain BM360 (obtained from Dr. A. Campbell, Stanford University, Stanford, Calif.) using conditions similar to those described in Example 4. An ampicillin resistant recombinant cell, denoted BM360-pCKRH$^{1col}$, was selected and cultured in M9CAT medium. Recombinant cell BM360-pCKRH$^{1col}$ grew well in M9CAT medium, which lacks biotin, indicating that the *Escherichia coli* bioH gene present on pCKRH$^{1col}$ is operatively linked to the tac transcription control sequences. That is, H$^{1col}$ is expressed as a protein that has the activity of an *Escherichia coli* bioH gene product.

Example 13

Biotin production using recombinant cells transformed with both pCKRH$^{1col}$ and pDIPA$^{col}$E$^{col}$B$^{col}$F$^{col}$C$^{col}$D$^{col}$ This example demonstrates that recombinant cells transformed with both an *Escherichia coli* bioH gene and the *Escherichia coli* biotin operon produce more biotin than do cells transformed with just the *Escherichia coli* biotin operon.

Recombinant cell BL21/DE3-pCKRH$^{1col}$+pDIPA$^{col}$E$^{col}$B$^{col}$F$^{col}$C$^{col}$D$^{col}$ was produced by transforming BL21/DE3-pDIPA$^{col}$E$^{col}$B$^{col}$F$^{col}$C$^{col}$D$^{col}$ cells (produced as described in Example 4B) with recombinant molecule pCKRH$^{1col}$ (produced as described in Example 11A and depicted in FIG. 19b) using techniques similar to those described in Example 4 and selecting for recombinant cells resistant to both ampicillin and chloramphenicol. Recombinant cell BL21/DE3-pCKR101+pDIPA$^{col}$E$^{col}$B$^{col}$F$^{col}$C$^{col}$D$^{col}$ was produced by transforming *Escherichia coli* BL21/DE3 cells with pCKR101 (see FIG. 19a) and recombinant molecule pDIPA$^{col}$E$^{col}$B$^{col}$F$^{col}$C$^{col}$D$^{col}$ (produced as described in Example 1D and shown in FIG. 5a) and selecting for recombinant cells in a similar manner.

Figure 23:
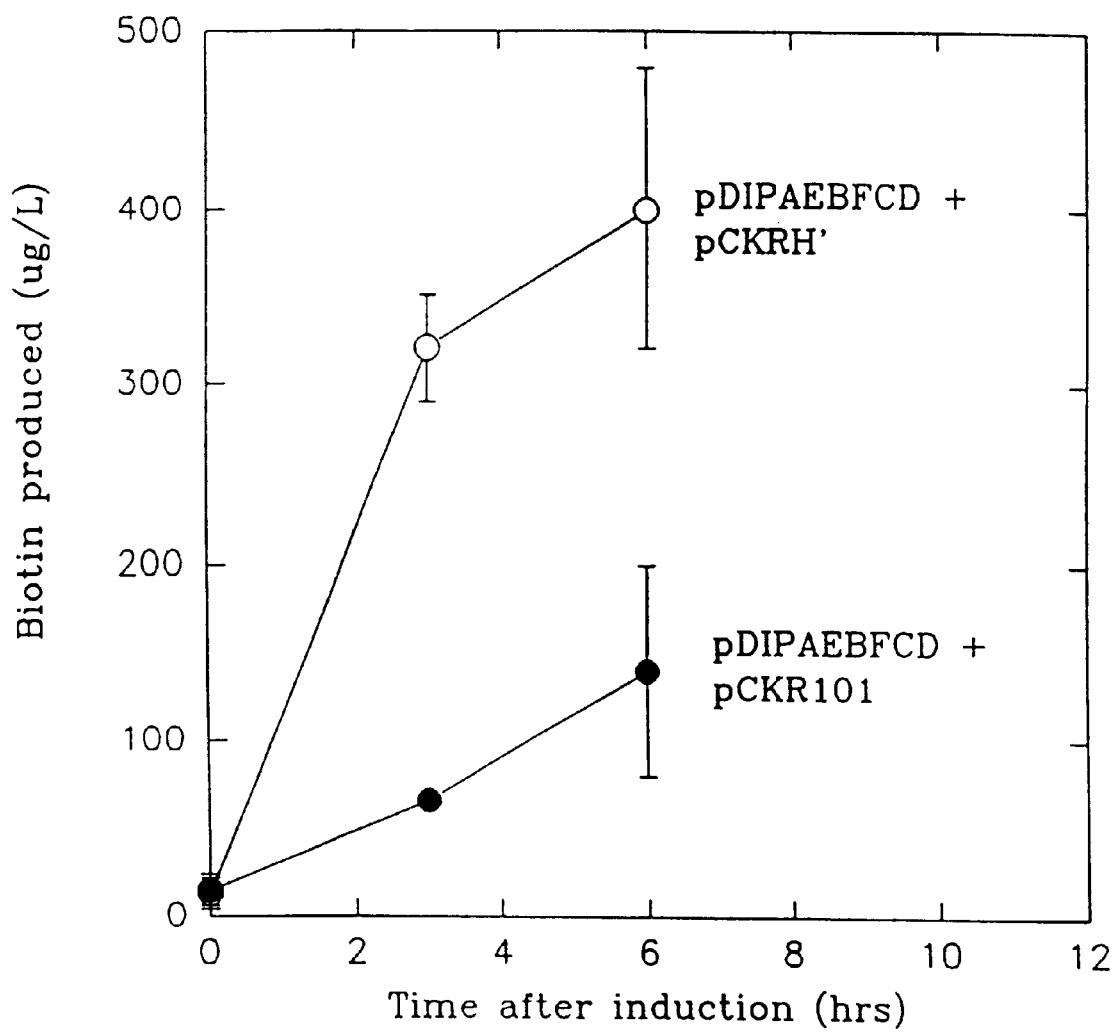
FIG. 23 illustrates a time course of biotin production by additional recombinant cells of the present invention.

BL21/DE3-pCKRH$^{1col}$+pDIPA$^{col}$E$^{col}$B$^{col}$F$^{col}$C$^{col}$D$^{col}$ and BL21/DE3-pCKR101+pDIPA$^{col}$E$^{col}$B$^{col}$F$^{col}$C$^{col}$D$^{col}$ were cultured in shake flasks as described in Example 7. Supernatant samples were collected at 0, 3, and 6 hours after IPTG induction and measured for true biotin content using the microbiological assay cited in Example 7. The results, as shown in FIG. 23, demonstrate that recombinant cells transformed with both an *Escherichia coli* bioH gene and the *Escherichia coli* biotin operon (recombinant cell denoted as pDIPAEBFCD+pCKRH') produced at least about 4 to about 5 times more true biotin than did cells transformed with just the *Escherichia coli* biotin operon and a control vector (denoted pDIPAEBFCD+pCKR101).

Example 14

Biotin production using recombinant cells transformed with pDIPH$^{1col}$A$^{col}$E$^{col}$B$^{col}$F$^{col}$C$^{col}$D$^{col}$ This example also demonstrates that recombinant cells transformed with both an *Escherichia coli* bioH gene and the *Escherichia coli* biotin operon produce more biotin than do cells transformed with just the *Escherichia coli* biotin operon.

Figure 20:
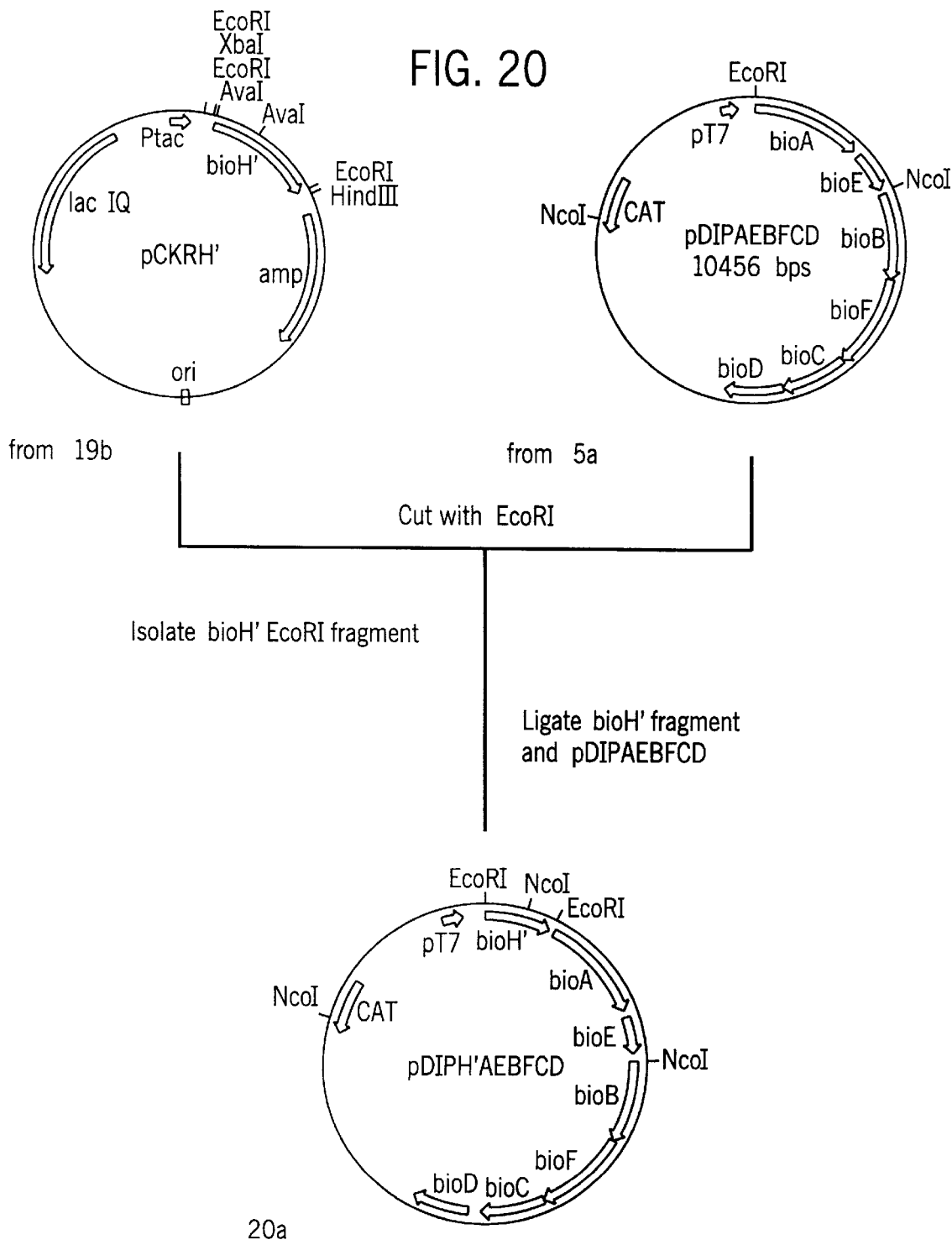
Figure 21:
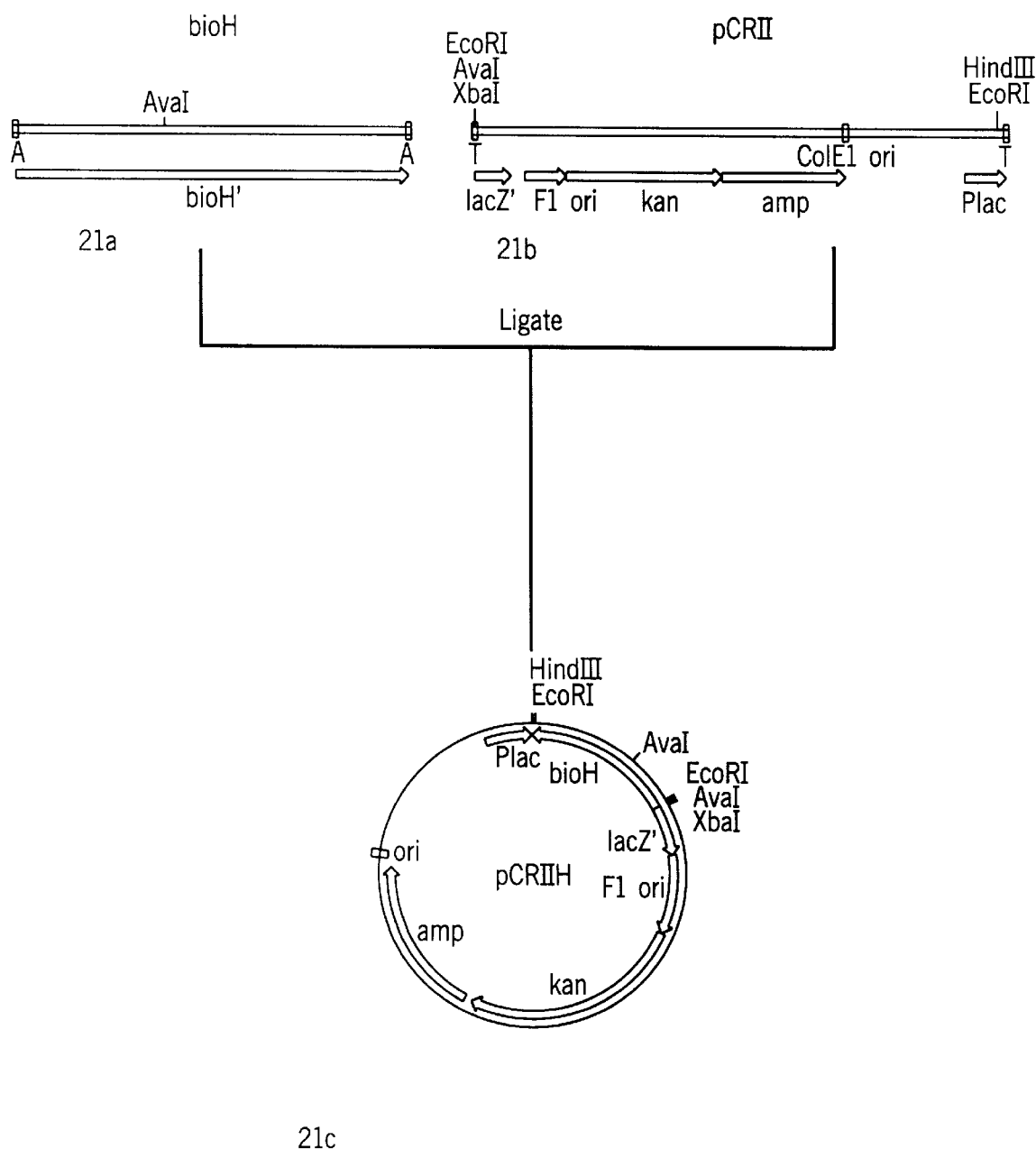

Recombinant cell BL21/DE3-pDIPH$^{1col}$A$^{col}$E$^{col}$B$^{col}$F$^{col}$C$^{col}$D$^{col}$ is produced by transforming *Escherichia coli* BL21/DE3 cells with recombinant molecule pDIPH$^{1col}$A$^{col}$E$^{col}$B$^{col}$F$^{col}$C$^{col}$D$^{col}$ (produced as described in Example 11B and depicted in FIG. 20a) as described in Example 4 and selecting for recombinant cells resistant to chloramphenicol.

Recombinant cells BL21/DE3-pDIPH$^{1col}$A$^{col}$E$^{col}$B$^{col}$F$^{col}$C$^{col}$D$^{col}$ and BL21/DE3-pDIPA$^{col}$E$^{col}$B$^{col}$F$^{col}$C$^{col}$D$^{col}$ (produced as described in Example 4B) are cultured in shake flasks as described in Example 7. Supernatant samples are collected at 0, 3, and 6 hours after IPTG induction and measured for true biotin content using the microbiological assay cited in Example 7. The results indicate that recombinant cells transformed with both an *Escherichia coli* bioH gene and the *Escherichia coli* biotin operon produce significantly more true biotin than do cells transformed with just the *Escherichia coli* biotin operon.

*Escherichia coli* BL21/DE-pCKRH$^{1col}$'pDIPA$^{col}$E$^{col}$B$^{col}$F$^{col}$C$^{col}$D$^{col}$, as a derivative of the pD1P18 plasmid, was deposited with DSMZ-Deutsche Sammlung von Mikroorganismen und Zellkulturen GmbH, Mascheroder Weg 1b, D-38124 Braunschweig, Germany, an International Depository Authority under provisions of the Budapest Treaty, on Feb. 15, 1995. The deposited material was assigned accession number DSM 9733.

Example 15

Biotin production using recombinant cells transformed with pDIPH$^{col}$A$^{col}$E$^{col}$B$^{col}$F$^{col}$C$^{col}$D$^{col}$ This example also demonstrates that recombinant cells transformed with both an *Escherichia coli* bioH gene and the *Escherichia coli* biotin operon produce more biotin than do cells transformed with just the *Escherichia coli* biotin operon.

Recombinant cell BL21/DE3-pDIPH$^{col}$A$^{col}$E$^{col}$B$^{col}$F$^{col}$C$^{col}$D$^{col}$ is produced by transforming *Escherichia coli* BL21/DE3 cells with recombinant molecule pDIPH$^{col}$A$^{col}$E$^{col}$B$^{col}$F$^{col}$C$^{col}$D$^{col}$ (produced as described in Example 11C and depicted in FIG. 22a) as described in Example 4 and selecting for recombinant cells resistant to chloramphenicol.

Recombinant cells BL21/DE3-pDIPH$^{col}$A$^{col}$E$^{col}$B$^{col}$F$^{col}$C$^{col}$D$^{col}$ and BL21/DE3-pDIPA$^{col}$E$^{col}$B$^{col}$F$^{col}$C$^{col}$D$^{col}$ (produced as described in Example 4B) are cultured in shake flasks as described in Example 7. Supernatant samples are collected at 0, 3, and 6 hours after IPTG induction and measured for true biotin content using the microbiological assay cited in Example 7. The results indicate that recombinant cells transformed with both an *Escherichia coli* bioH gene and the *Escherichia coli* biotin operon produce significantly more true biotin than do cells transformed with just the *Escherichia coli* biotin operon.

*Escherichia coli* BL</DE3-pCKRH$^{1col}$ +pDIPA$^{col}$E$^{col}$B$^{col}$F$^{col}$C$^{col}$D$^{col}$, as a derivative of the pD1P18 plasmid, was deposited with DSMZ-Deutsche Sammlung von Mikroorganismen und Zellkultren GmbH, Mascheroder Weg 1b, D-38124 Braunschweig, Germany, an International Depository Authority under provisions of the Budapest Treaty, on Feb. 15, 1995. The deposited material was assigned accession number DSM 9733.

Escherichia coli BL21/DE3-pCKRH$^{1col}$+pDIPA$^{col}$E$^{col}$B$^{col}$F$^{col}$C$^{col}$D$^{col}$, a derivative of the pD1P18 plasmid, was deposited with DSMZ-Deutsche Sammlung von Mikroorganismen und Zellkulturen GmbH, Mascheroder Weg 1b, D-38124 Braunschweig, Germany, an International Depository Authority under provisions of the Budapest Treaty, on Feb. 15, 1995. The deposited nmaterial was assigned accession number DSM 9733.

While various embodiments of the present invention have been described in detail, it is apparent that modifications and adaptations of those embodiments will occur to those skilled in the art. However, it is to be expressly understood that such modifications and adaptations are within the scope of the present invention, as set forth in the following claims.

What is claimed is:

1. A biotin overproducing recombinant cell transformed with an *Escherichia coli* bioH gene, said recombinant cell being capable of producing more biotin than a cell not transformed with an *Escherichia coli* bioH gene.

2. The recombinant cell of claim 1 selected from the group consisting of bacteria and yeast.

3. The recombinant cell of claim 1, wherein said recombinant cell is of the species *Escherichia coli*.

4. The recombinant cell of claim 1, wherein said *Escherichia coli* bioH gene is operatively linked to a transcription control sequence to form a recombinant molecule.

5. The recombinant cell of claim 4, wherein said transcription control sequence comprises a bacteriophage T7 or a tac transcription control sequence.

6. The recombinant cell of claim 1, wherein said recombinant cell is also transformed with at least one nucleic acid sequence selected from the group consisting of *Escherichia coli* bioA, bioB, bioC, bioD, bioE, and bioF genes.

7. The recombinant cell of claim 6, wherein said *Escherichia coli* bioH gene and said nucleic acid sequence are operatively linked to at least one transcription control sequence to form at least one recombinant molecule.

8. The recombinant cell of claim 1 transformed with (a) an *Escherichia coli* bioA gene; (b) an *Escherichia coli* bioB gene; (c) an *Escherichia coli* bioC gene; (d) an *Escherichia coli* bioD gene; (e) an *Escherichia coli* bioE gene; (f) an *Escherichia coli* bioF gene; and (g) an *Escherichia coli* bioH gene.

9. The recombinant cell of claim 1, wherein said recombinant cell is capable of producing at least about fifty percent more biotin than a cell not transformed with an *Escherichia coli* bioH gene.

10. The recombinant cell of claim 1 comprising an *Escherichia coli* transformed with recombinant molecule pCRH$^{col}$.

11. The recombinant cell of claim 1, wherein the said recombinant cell is *Escherichia coli* BL21/DE3-pCKRH$^{col}$+pDIPA$^{col}$E$^{col}$B$^{col}$F$^{col}$C$^{col}$D$^{col}$.

12. The recombinant cell of claim 1 produced by a method comprising:

(a) operatively linking said *Escherichia coli* bioH gene to a transcription control sequence to form a recombinant molecule; and (b) transforming said recombinant molecule into a host cell to form said recombinant cell.

13. The recombinant cell of claim 12, wherein indigenous production of biotin by said host cell is deregulated.

14. The recombinant cell of claim 6 produced by a method comprising:

(a) operatively linking said *Escherichia coli* bioH gene and at least one nucleic acid sequence selected from said group to at least one transcription control sequence to form at least one recombinant molecule; and (b) transforming said recombinant molecule(s) into a host cell to form said recombinant cell.

15. A recombinant molecule comprising an *Escherichia coli* bioH gene, operatively linked to a transcription control sequence selected from the group consisting of bacterial and yeast transcription control sequences.

16. The recombinant molecule of claim 15 further comprising at least one nucleic acid selected from the group consisting of *Escherichia coli* bioA, bioB, bioC, bioD, bioE, and bioF genes operatively linked to at least one transcription control sequence selected from the group consisting of bacterial and yeast transcription control sequences.

17. The recombinant molecule of claim 15, wherein said transcription control sequence is selected from the group consisting of Escherichia, Bacillus, Pseudomonas, Salmonella, Corynebacterium, and Saccharomyces transcription control sequences.

18. The recombinant molecule of claim 15, wherein said transcription control sequence comprises a bacteriophage T7 or tac transcription control sequence.

19. The recombinant molecule of claim 15, wherein said recombinant molecule comprises a nucleic acid sequence selected from the group consisting of H$^{col}$, B$^{col}$H$^{col}$, E$^{col}$H$^{col}$, E$^{col}$B$^{col}$H$^{col}$, E$^{col}$B$^{col}$D$^{col}$H$^{col}$, E$^{col}$B$^{col}$D$^{col}$A$^{col}$H$^{col}$, E$^{col}$B$^{col}$D$^{col}$A$^{col}$F$^{col}$H$^{col}$, E$^{col}$B$^{col}$D$^{col}$-iA$^{col}$F$^{col}$C$^{col}$H$^{col}$.

20. The recombinant molecule of claim 15, wherein said recombinant molecule is pCKRH$^{col}$.

21. A method to produce a recombinant cell comprising transforming a host cell with an *Escherichia coli* bioH gene, said recombinant cell being capable of producing more biotin than a cell not transformed with an *Escherichia coli* bioH gene.

22. The method of claim 21 further comprising transforming said host cell with at least one nucleic acid selected from the group consisting of *Escherichia coli* bioA, bioB, bioC, bioD, bioE, and bioF genes.

23. A method to produce biotin comprising:

(a) culturing in a medium effective to produce biotin a biotin overproducing recombinant cell transformed with an *Escherichia coli* bioH gene, said recombinant cell being capable of producing more biotin than a cell not transformed with an *Escherichia coli* bioH gene; and (b) recovering biotin produced thereby.

24. The method of claim 23, wherein said recombinant cell is also transformed with at least one nucleic acid selected from the group consisting of *Escherichia coli* bioA, bioB, bioC, bioD, bioE, and bioF genes.

* * * * *

UNITED STATES PATENT AND TRADEMARK OFFICE
CERTIFICATE OF CORRECTION

PATENT NO. : 6,277,609 B1
DATED : August 21, 2001
INVENTOR(S) : Christina K. Eddy It is certified that error appears in the above-identified patent and that said Letters Patent is hereby corrected as shown below:

Column 30,
Line 19, replace "pDIPA$^{col}$E$^{co}$X-" with -- pDIPA$^{col}$E$^{col}$X- --.

Column 32,
Line 38, replace "bioB" with -- bioH --.

Column 34,
Delete lines 28-35.
Line 38, replace "pDIPH$^{col}$ A$^{col}$ E$^{col}$B$^{col}$ F$^{col}$ F$^{col}$ D$^{col}$" with -- pDIPH$^{\cdot col}$ A$^{col}$E$^{col}$B$^{col}$F$^{col}$C$^{col}$D$^{col}$ --.
Line 45, replace "pDIPH$^{col}$ A$^{col}$E$^{col}$B$^{col}$F$^{col}$ F$^{col}$ D$^{col}$" with -- pDIPH$^{\cdot col}$ A$^{col}$E$^{col}$B$^{col}$F$^{col}$C$^{col}$D$^{col}$ --.
Line 47, replace "pDIPH$^{col}$ A$^{col}$E$^{col}$B$^{col}$F$^{col}$ C$^{col}$ D$^{col}$" with -- pDIPH$^{\cdot col}$ A$^{col}$E$^{col}$B$^{col}$F$^{col}$C$^{col}$D$^{col}$ --.
Line 48, replace "11C" with -- 11B -- and "FIG. 22a" with -- FIG.20a --.
Line 52, replace "pDIPH$^{col}$ A$^{col}$E$^{col}$B$^{col}$F$^{col}$ C$^{col}$ D$^{col}$" with -- pDIPH$^{\cdot col}$ A$^{col}$E$^{col}$B$^{col}$F$^{col}$C$^{col}$D$^{col}$ --.
Line 63, replace "<" with -- 21 --.

Column 35,
Delete lines 4-9.

Column 36,
Delete lines 1-2.

Signed and Sealed this

Twenty-sixth Day of February, 2002

Attest:

*Attesting Officer*

JAMES E. ROGAN
*Director of the United States Patent and Trademark Office*